United States Patent
D'Alessio et al.

(10) Patent No.: US 10,905,706 B2
(45) Date of Patent: Feb. 2, 2021

(54) COMPOSITIONS AND METHODS TO ACCELERATE RESOLUTION OF ACUTE LUNG INFLAMMATION

(71) Applicant: The Johns Hopkins University, Baltimore, MD (US)

(72) Inventors: Franco D'Alessio, Baltimore, MD (US); Benjamin David Singer, Baltimore, MD (US); Landon King, Lutherville, MD (US); Neil Raj Aggarwal, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 61 days.

(21) Appl. No.: 15/542,380

(22) PCT Filed: Jan. 8, 2016

(86) PCT No.: PCT/US2016/012621
§ 371 (c)(1),
(2) Date: Jan. 3, 2018

(87) PCT Pub. No.: WO2016/112271
PCT Pub. Date: Jul. 14, 2016

(65) Prior Publication Data
US 2018/0125874 A1    May 10, 2018

Related U.S. Application Data

(60) Provisional application No. 62/136,199, filed on Mar. 20, 2015, provisional application No. 62/101,319, filed on Jan. 8, 2015.

(51) Int. Cl.
| | | |
|---|---|---|
| *A61K 31/7068* | (2006.01) | |
| *A61P 11/00* | (2006.01) | |
| *A61K 31/502* | (2006.01) | |
| *A61K 31/245* | (2006.01) | |
| *A61K 31/353* | (2006.01) | |
| *A61K 31/706* | (2006.01) | |
| *A61P 29/00* | (2006.01) | |
| *A61P 31/16* | (2006.01) | |
| *A61K 31/166* | (2006.01) | |

(52) U.S. Cl.
CPC ........ *A61K 31/7068* (2013.01); *A61K 31/166* (2013.01); *A61K 31/245* (2013.01); *A61K 31/353* (2013.01); *A61K 31/502* (2013.01); *A61K 31/706* (2013.01); *A61P 11/00* (2018.01); *A61P 29/00* (2018.01); *A61P 31/16* (2018.01)

(58) Field of Classification Search
CPC ................................................ A61K 31/7068
See application file for complete search history.

(56) References Cited

U.S. PATENT DOCUMENTS

| | | | |
|---|---|---|---|
| 4,522,810 A | 6/1985 | Pedersen | |
| 4,588,580 A | 5/1986 | Gale et al. | |

FOREIGN PATENT DOCUMENTS

| | | |
|---|---|---|
| WO | WO-2009126877 A2 | 10/2009 |
| WO | WO-2010054126 A2 | 5/2010 |
| WO | WO-2013050596 A1 | 4/2013 |

OTHER PUBLICATIONS

Hueser, C. et al., Pharmacotherapy, "Azacitidine-Associated Hyperthermia and Interstitial Pneumonitis in a Patient with Myelodysplastic Syndrome", 2007, vol. 27, No. 12, pp. 1759-1762 (Year: 2007).*
Reagan-Shaw, S. et al., The FASEB Journal, "Dose translation from animal to human studies revisted", 2007, vol. 22, pp. 659-661 (Year: 2007).*
Chan, M.W.Y., et al., "Low-dose 5-aza 2'—deoxycytidine pretreatment inhibits experimental autoimmune encephalomyelitis by induction of regulatory T cells", Molecular Medicine, 2014, vol. 20, pp. 248-256.
Lee, S.W., et al., "Anti-inflammatory effects of IL-4 and IL-10 on human polymorphonuclear leukocytes", Journal of Korean Medical Science, 2002, vol. 17, pp. 7-14.
Meduri, G.U. et al., "Persistent elevation of inflammatory cytokines predicts a poor outcome in ARDS: plasma IL-1β and IL-6 levels are consistent and efficient predictors of outcome over time". CHEST Journal, 1995, vol. 107, No. 4, pp. 1062-1073.
Quddus, J., et al., "Treating activated CD4+ T cells with either of two distinct DNA methyltransferase inhibitors, 5-azacytidine or procainamide, is sufficient: to cause a lupus-like disease in syngeneic mice". Journal of Clinical Investigation, 1993, vol. 92, pp. 38-53.
Singer, B.D., et al., "Regulatory T cell DNA methyltransferase inhibition accelerates resolution of lung inflammation", American Journal of Respiratory Cell and Molecular Biology, Originally Published in Press as DOI: 10.1165/rcmb.2014-0327OC on Oct. 8, 2014, vol. 52, No. 5, pp. 641-647.
Written Opinion of the International Searching Authority issued in corresponding International Application Ser. No. PCT/US2016/012621, dated Jun. 23, 2016, 8 pages.
International Search Report issued in corresponding International Application Ser. No. PCT/US2016/012621, dated Jun. 23, 2016, 4 pages.

(Continued)

*Primary Examiner* — Bahar Craigo
(74) *Attorney, Agent, or Firm* — Mintz Levin Cohn Ferris Glovsky and Popeo, P.C.; Peter F. Corless

(57) ABSTRACT

The present invention provides methods and compositions for treatment of acute inflammatory diseases or disorders and/or for treatment of lung injury. Certain exemplary methods involve administering an IL-4 polypeptide or fragment thereof possessing cytokine activity or an IL-4 agonist systemically to a subject having an inflammatory disease or disorder and/or a lung injury. Other exemplary methods involve administering an inhibitor of DNA methylation systemically to a subject and/or administering an inhibitor of DNA methylation to a cell population comprising T cells (e.g., Treg cells) for introduction/re-introduction to a subject having an inflammatory disease or disorder and/or a lung injury. Compositions and cells for use in such methods are also provided.

6 Claims, 38 Drawing Sheets

Specification includes a Sequence Listing.

(56) References Cited

OTHER PUBLICATIONS

Obata, et al., The epigenetic regulator Uhrf1 facilitates the proliferation and maturation of colonic regulatory T cells. Nat Immunol 2014;15:571-579.

Wang, et al., Foxp3+ T-regulatory cells require DNA methyltransferase 1 expression to prevent development of lethal autoimmunity. Blood 2013;121:3631-3639.

Thangavel, et al., Combinatorial therapy witb acetylation and methylation modifiers attenuates lung vascular hyperpermeability in endotoxemia-induced mouse inflammatory lung injury. Am J Pathol 2014;184:2237-2249.

The Acute Respiratory Distress Syndrome Network. Ventilation with lower tidal volumes as compared with traditional tidal volumes for acute lung injury and the acute respiratory distress syndrome. New England.Journal of medicine 2000; 342: 1301-1308.

Aggarwal, et al., Moderate oxygen augments lipopolysaccharide-induced lung injury in mice. Am J Physiol Lung Cell Mol Physiol 2010; 298: L371-38L.

Aggarwal, et al., Diverse macrophage populations mediate acute lung inflammation and resolution. Am J Physiol Lung Cell Mol Physiol 2014; 306: L709-725.

Aggarwal, et al., Immunological priming requires regulatory T cells and IL-10-producing macrophages to accelerate resolution from severe lung inflammation. J Immunol 2014; 192: 4453-4464.

Bouros, et al., The clinical significance of serum 3nd bronchoalveolar lavage inflammatory cytokines in patients at risk for Acute Respiratory Distress Syndrome. BMC pulmonary medicine 2004; 4: 6.

El Kasmi, et al., Toll-like receptor-induced arginase 1 in macrophages thwarts effective immunity against intracellular pathogens. Nat Immunol 9: 1399-1406, 2008.

Fadok, et al., Macrophages that have ingested apoptotic cells in vitro inhibit proinflarnmatory cytokine production through autocrine/paracrine mechanisms involving TGF-beta, PGE2, and PAF. J Clin Invest 101: 890-898, 1998.

Fallica, et al., Application of carbon monoxide diffusing capacity in the mouse Jung. J Appl Physiol (1985) 110: 1455-1459, 2011.

Fan, et al., Physical complications in acute lung injury survivors: a two-year longitudinal prospective study. Crit Care Med 42: 849-859, 2014.

Fernandez-Boyanapalli, et al., Impaired apoptotic cell clearance in CGD due to altered macrophage programming is reversed by phosphatidylserine-dependent production of TL-4. Blood 113: 2047-2055, 2009.

Finkelman, et al., Anti-cytokine antibodies as carrier proteins. Prolongation of in vivo effects of exogenous cytokines by injection of cytokine-anti-cytokine antibody complexes. J Immunol 151: 1235-1244, 1993.

Fleming, et al., The generation of macrophages with anti-inflammatory activity in the absence of STAT6 signaling. Journal of leukocyte biology 2015; 98: 395-407.

Gordon, et al., Alternative activation of macrophages: mechanism and functions. Immunity 32: 593-604, 2010.

Gordon, et al., Monocyte and macrophage heterogeneity. Nat Rev Immunol 5: 953•-964, 2005.

Guerin, et al., Prone positioning in severe acute respiratory distress syndrome. N Engl J Med 368: 2159-2168, 2013.

Halbower, et al., Agarose infiltration improves morphology of cryostat sections of lung. Lab Invest 71: 149-153, 1994.

Heller, et al., Type I IL-4Rs selectively activate IRS-2 to induce target gene expression in macrophages. Sci Signal 1: ral7, 2008.

Herold, et al., Acute lung injury: how macrophages orchestrate resolution of inflammation and tissue repair. Front Immunol 2: 65, 2011.

Huanx, et al., Dual roles of TL-4 in lung injury and fibrosis. J immunol 170: 2083-2092, 2003.

Lawrence, et al., Transcriptional regulation of macrophage polarization: enabling diversity with identity. Nat Rev Immunol 11: 750-761, 2011.

Lazarski, et al., IL-4 attenuates Th1-associated chemokine expression and Th 1 trafficking to inflamed tissues and limits pathogen clearance. PLoS One 8: e71949, 2013.

Lee, et al., Steady-state production of IL-4 modulates immunity in mouse strains and is determined by lineage diversity of iNKT cells. Nat Immunol 14: 1146-1154, 2013.

Levitt, et al., Identification of early acute lung injury at initial evaluation in an acute care setting prior to the onset of respiratory failure. Chest 135: 936-943, 2009.

Levy, et al., Resolution of acute inflammation in the lung. Annual review of physiology 76: 467-492, 2014.

Li, et al., Eight-year trend of acute respiratory distress syndrome: a population-based study in Olmsted County, Minnesota. Am J Respir Crit Care Med 183: 59-66, 2011.

Mantovani, et al., Macrophage plasticity and polarization in tissue repair and remodelling. J Pathol. Jan;229(2):176-85, 2013.

Matthay, et al., The acute respiratory distress syndrome. J Clin Invest 122: 2731-2740. 2012.

Meduri, et al., Persistent elevation of inflammatory cytokines predicts a poor outcome in ARDS. Plasma IL-1 beta and IL-6 levels are consistent and efficient predictors of outcome over lime. Chest 107:1062-1073, 1995.

Melgert, et al., More alternative activation of macrophages in lungs of asthmatic patients. J Allergy Clin Immunol 127: 831-833, 2011.

Nair, et al., Alternatively activated rnacrophage-derived RELM-{alpha} is a negative regulator of type 2 inflammation in the lung. The Journal of experimental medicine 206: 937-952, 2009.

Pace, et al., Cutting edge: IL-4-induced protection of CD4+CD25-Th cells from CD4+CD25+ regulatory T cell-mediated suppression. J Immunol 176: 3900-3904, 2006.

Papazian, et al., Neuromuscular blockers in early acute respiratory distress syndrome. N Engl J Med 363: 1107-1116, 2010.

Pechkovsky, et al., Alternatively activated alveolar macrophages in pulmonary fibrosis-mediator production and intracellular signal transduction. Clinical Immunology 137: 89-101, 2010.

Pesce, et al., Arginase-1-expressing macrophages suppress Th2 cytokine-driven inflammation and fibrosis. PLoS Pathog 5: e1000371, 2009.

Qualls, et al., Arginine usage in mycobacteria-infected macrophages depends on autocrine-paracrine cytokine signaling. Science signaling 3: ra62, 2010.

Pesce, et al., Retnla (relmalpha/fizz1) suppresses helminth-induced Th2-type immunity. PLoS Pathog 5: e1000393, 2009.

Rosseau, et al., Phenotypic characterization of alveolar monocyte recruitment in acute respiratory distress syndrome. Am J Physiol Lung Cell Mol Physiol 279: L25-35, 2000.

Sica, et al., Macrophage plasticity and polarization: in vivo veritas. J Clin Invest 122: 787-795, 2012.

Sindrilaru, et al., An unrestrained proinflammatory MI macrophage population induced by iron impairs wound healing in humans and mice. J Clin Invest 121: 985-997, 2011.

Singer, et al., Regulatory T cell DNA methyltransferase inhibition accelerates resolution of lung inflammation. Am J Respir Cell Mol Biol 52: 641-652, 2015.

Steinberg, et al., Evolution of bronchoalveolar cell populations in the adult respiratory distress syndrome. Am J Respir Crit Care Med 150: 113-122, 1994.

Taams, et al., Modulation of monocyte/macrophage function by human CD4+CD25+ regulatory T cells. Human immunology 66: 222-230, 2005.

Thepen, et al., Alveolar macrophage elimination in vivo is associated with an increase in pulmonary immune response in mice. J Exp Med 170: 499-509, 1989.

Tiemessen, et al., CD4+CD25+Foxp3+ regulatory T cells induce alternative activation of human monocytes/macrophages. Proc Natl Acad Sci USA 104: 19446-19451, 2007.

Wynn. IL-13 effector functions. Annual review immunology 21: 425-456, 2003.

Wynn, et al., Cytokine regulation of granuloma formation in schistosomiasis. Curr Opin Immunol 7: 505-511, 1995.

Zaynagetdinov, et al., Identification of Myeloid Cell Subsets in Murine Lungs Using Flow Cytometry. Am J Respir Cell Mol Biol 2013; 49: 180-189.

(56) References Cited

OTHER PUBLICATIONS

Karlin, et al., Methods for assessing the statistical significance of molecular sequence features by using general scoring schemes. Proc. Natl. Acad. Sci. USA 1990; 87: 2264-2268.
Karlin, et al., Applications and statistics for multiple high-scoring segments in molecular sequences. Proc. Natl. Acad. Schi. USA 1993; 90: 5873-5877.
Altschul, et al., Gapped BLAST and PSI-BLAST: a new generation of protein database search programs. Nucleic Acids Res 1997; 25: 3389-3402.
Altschul, et al., [27] Local alignment statistics. Methods in Enzymology 1996; 266: 460-480.
Smith, et al., Comparison of Biosequences. Advances in Applied Mathematics 1981; 2: 482-489.
Brummel, et al., Probing the combining site of an anti-carbohydrate antibody by saturation-mutagenesis: Role of the heavy-chain CDR3 residues. Biochemistry 1993; 32: 1180-1187.
Kobayashi, et al., Tryptophan H33 plays an important role in pyrimidine (6-4) pyrimidone photoproduct binding by a high-affinity antibody. Protein Engineering 1999: 12: 879-884.
Burks, et al., In vitro scanning saturation mutagenesis of an antibody binding.pocket. Proc. Natl. Acad. Sci. USA 1997; 94: 412-417.
D'Alessio, et al., Resolution of experimental lung injury by monocyte-derived inducible nitric oxide synthase. Immunol. 2012; I 89(5):2234-45.
Aggarwal, et al., Macrophage adenosine receptor 2a (A2aR) protects against oxygen-induced augmentation of experimental lung injury. Am J Respir Cell Mol Biol 2013; 48: 635-646.
Ghoreschi, et al., Interleukin-4 therapy of psoriasis induced Th2 responses and improves human autoimmune disease. Nat Med 2003;9:40-46.
Wong, et al., Administration of recombinant IL-4 to humans regulates gene expression, phenotype, and function in circulating monocytes. J Immunol 1992; 148:2118-2125.
Shanafelt, et al., An immune cell-selective interleukin 4 agonist. Proc. Natl. Acad. Sci. USA 1995; 95: 9454-9458.
Wu, et al., The DNA methylation inhibitor 5-azacytidine increases regulatory T cells and alleviates airway inflammation in ovalbumin-sensitized mice. Int Arch Allergy Immunol 2013; 160: 356-364.
Velthuis, et al., CD4+CD25bright+ regulatory T cells can mediate donor nonreactivity in long-term immunosuppressed kidney allograft patients. Am J Transplant 2006; 6: 2955-2964.
Zheng, et al., Induction of Foxp3 demethylation increases regulatory CD4+CD25+ T cells and prevents the occurrence of diabetes in mice. J Mol Med (Berl) 2009; 87: 1191-1205.
Adamzik, et al., An increased alveolar CD4 + CD25 + Foxp3 + T-regulatory cell ratio in acute respiratory distress syndrome is associated with increased 30-day mortality. Intensive Care Med 2013; 39: 1743-1751.
Wang, et al., BLT1-dependent alveolar recruitment of CD4(+)CD25(+) Foxp3(+) regulatory T cells is important for resolution of acute lung injury. Am J Respir Crit Care Med 2012; 186: 989-998.
Bailey-Bucktrout, et al., Self-antigen-driven activation induces instability of regulatory T cells during an inflammatory autoimmune response. Immunity 2013;39:949-962.
Bettini, et al., Loss of epigenetic modification driven by the Foxp3 transcription factor leads to regulatory T cell insufficiency. Immunity 2012;36:717-730.
Bollyky, et al., CD44 costimulation promotes FoxP3+ regulatory T cell persistence and function via production of IL-2, IL-10, and TGF-beta. J Immunol 2009; 183:2232-2241.
Borsellino, et al., Expression of ectonucleotidase CD39 by Foxp3+ Treg cells: hydrolysis of extracellular ATP and immune suppression. Blood 2007; 110: 1225-1232.
Brunstein, et al., linfusion of ex vivo expanded T regulatory cells in adults transplanted with umbilical cord blood: safety profile and detection kinetics. Blood 2011; 117: 1061-1070.
Buckley, et al., Resolution of Inflammation. Nat Rev Immunol 2013;13:59-66.

D'Alessio, et al., CD4+CD25+Foxp3+ Tregs resolve experimental lung injury in mice and are present in humans with acute lung injury. J Clin Invest 2009; 119:2898-2913.
Burzyn, et al., A special population of regulatory T cells potentiates muscle repair. Cell 2013;155:1282-1295.
Chauhan, et al., Levels of Foxp3 in regulatory T cells reflect their functional status in transplantation. J Immunol 2009; 182: 148-153.
Collison, et al., In vitro Treg suppression assays. Methods Mol Biol 2011;707:21-37.
Fontenot, et al., Regulatory T cell lineage specification by the forkhead transcription factor foxp3. Immunity 2005:22:329-341.
Di Ianni, et al., Tregs prevent GVHD and promote immune reconstitution in HLA-haploidentical transplantation. Blood 2011;117:3921-3928.
Festing, et al., Guidelines for the design and statistical analysis of experiments using laboratory animals. ILAR J 2002;43:244-258.
Floess, et al., Epigenetic control of the foxp3 locus in regulatory T cells. PLoS Biol 2007;5:e38.
Fontenot, et al., Foxp3 programs the development and function of CD4+CD25+ regulatory T cells. Nat Immunol 2003;4:330-336.
Garibaldi, et al., Regulatory T cells reduce acute lung injury fibroproliferation by decreasing fibrocyte recruitment. Am J Respir Cell Mol Biol 2013;48:35-43.
Hippen, et al., Massive ex vivo expansion of human natural regulatory T cells (T(regs)) with minimal loss of in vivo functional activity. Sci Transl Med 2011;3:83ra41.
Hoffmann, et al., Large-scale in vitro expansion of polyclonal human CD4(+)CD25high regulatory T cells. Blood 2004; 104:895-903.
Hori, et al., Control of regulatory T cell development by the transcription factor Foxp3. Science 2003;299:1057-I 06 L.
Ishii, et al., Epigenetic regulation of the alternatively activated rnacrophage phenotype. Blood 2009;114:3244-3254.
Janson, et al., FOXP3 promoter demethylation reveals the committed Treg population in humans. PLoS One 2008;3:e1612.
Josefowicz, et al., Control of regulatory T cell lineage commitment and maintenance. Immunity 2009; 30:616-625.
Kehrmann, et al., Impact of 5-aza-2'-deoxycytidine and epigallocatechin-3-gallate for induction of human regulatory T cells. Immunology 2014;142:384-395.
Kim, et al., CREB/ATF-dependent T cell receptor-induced FoxP3 gene expression: a role for DNA methylation. J Exp Med 2007;204: 1543-1551.
Kobayashi, et al., Tryptophan H33 plays an important role in pyrimidine (6-4) pyrimidone photoproduct binding by a high-affinity antibody. Protein Engineering 1999; vol. 12 No. 10 pp. 879-884.
Kochanek, et al., Histone deaccetylase inhibitor treatment attenuates MAP kinase pathway activation and pulmonary inflammation following hemorrhagic shock in a rodent model. J Surg Res 2012;176:185-194.
Komatsu, et al., Pathogenic conversion of Foxp3+ T cells into TH17 cells in autoimmune arthritis. Nat Med 2013;20:62-68.
Lal, et al., Epigenetic mechanisms of regulation of Foxp3 expression. Blood 2009; I 14:3727-3735.
Lal, et al., Epigenetic regulation of Foxp3 expression in regulatory T cells by DNA methylation. J Immunol 2009; 182:259-273.
Leonhardt, et al., A targeting sequence directs DNA methyltransferase to sites of DNA replication in rnarnrnalian nuclei. Cell 1992;71:865-873.
Li, et al., Protective effect of suberoylanilide hydroxamic acid against LPS-induced septic shock in rodents. Shock 2009;32:517-523.
Mantel, et al., Molecular mechanisms underlying FOXP3 induction in human T cells. J Immunol 2006; 176:3593-3602.
Matute-Bello, et al., Animal models of acute lung injury. Am J Respir Cell Mol Biol 2008;295:L379-L399.
Miyao, et al., Plasticity of Foxp3(+) T cells reflects promiscuous Foxp3 expression in conventional T cells but not reprogramming of regulatory T cells. Immunity 2012;36:262-275.
Mock, et al., Foxp3(+) regulatory T cells promote lung epithelial proliferation. Mucosal Immunol 2014; 7:1440-1451.

(56) References Cited

OTHER PUBLICATIONS

Moon, et al., Use of epigenetic modification to induce FOXP3 expression in naive T cells. Transpl Proc 2009;41:1848-1854.
Ni, et al., Histone deacetylase inhibitor, butyrate, attenuates lipopolysaccharide-induced acute lung injury in mice. Respir Res 2010;11:33.
Ohkura, et al., T cell receptor stimulaion-induced epigenetic changes and Foxp3 expression are independent and complementary events required for Treg cell development. Immunity 2012;37:785-799.
Polanksy, et al., DNA methylation controls Foxp3 gene expression. Eur J Immunol 2008;38: 1654-1663.
Rubenfeld, et al., Incidence and outcomes of acute hrng injury. N Engl J Med 2005;353: 1685-1693.
Sakaguchi, et al., Immunologic self-tolerance maintained by activated T cells expressing IL-2 receptor alpha—chains (CD25). Breakdown of a single mechanism of self-tolerance causes various autoimmune diseases. J Jmmunol 1995;155: 1151-1164.
Serhan, et al., Resolution of inflammation: state of the art, definitions and terms. FASEB J 2007;21:325-332.
Singer, et al., Pharmacologic epigenetic manipulation rescues experimental lung injury and promotes lung regulatory T cell number and suppressive phenotype [abstract]. Am J Respir Crit Care Med 2013; 187:A1213.
Singer, et al., DNA demethylation promotes regulatory T cell-mediated resolution of acute lung injury [abstract]. Am J Respir Crit Care Med 2014; 189:A5575.
Singer, et al., Regulatory T cells as immunotherapy. Front Immunol 2014;5:46.
Ware, et al., The acute respiratory distress syndrome. N Engl J Med 2000;342:1301-1308.
Toker, et al., Active demethylation of the Foxp3 locus leads to the generation of stable regulatory T cells within the thymus. J Immunol 2013: 190:3180-3188.
Trzonkowski, et al., First-in-man clinical results of the treatment of patients with graft versus host disease with human ex vivo expanded CD4+CD25+CD127-T regulatory cells. Clin Immunol 2009;133:22-26.
Van Loosdregt, et al., Stabilization of the transcription factor Foxp3 by the deubiquitinase USP7 increases Treg-cell-suppressive capacity. Immunity 2013;39:259-•27 I.
Wilson, et al., Epigenetic control of T-helper-celJ differentiation. Nat Rev Immunol 2009;9:91-105.
Wing, et al., CTLA-4 control over Foxp3+ regulatory T cell function. Science 2008; 22:271-275.

* cited by examiner

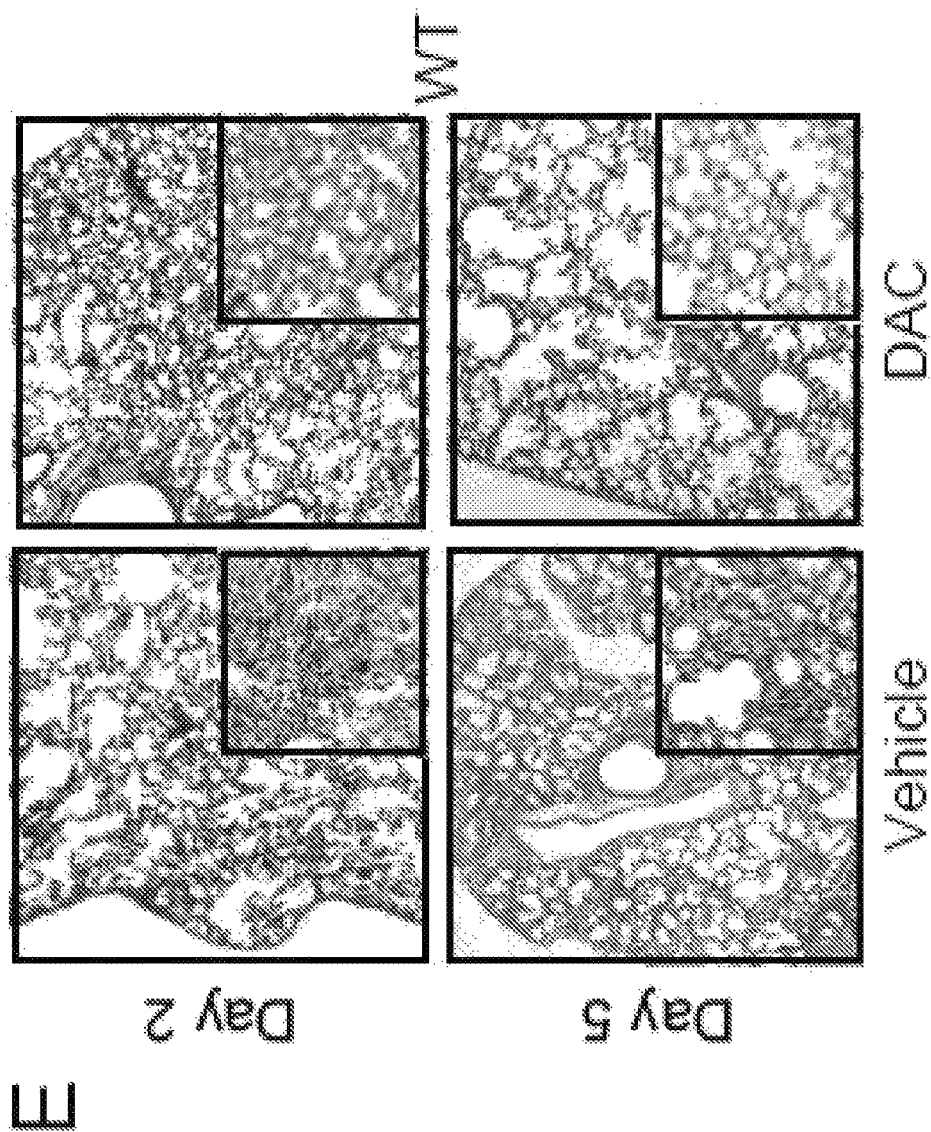

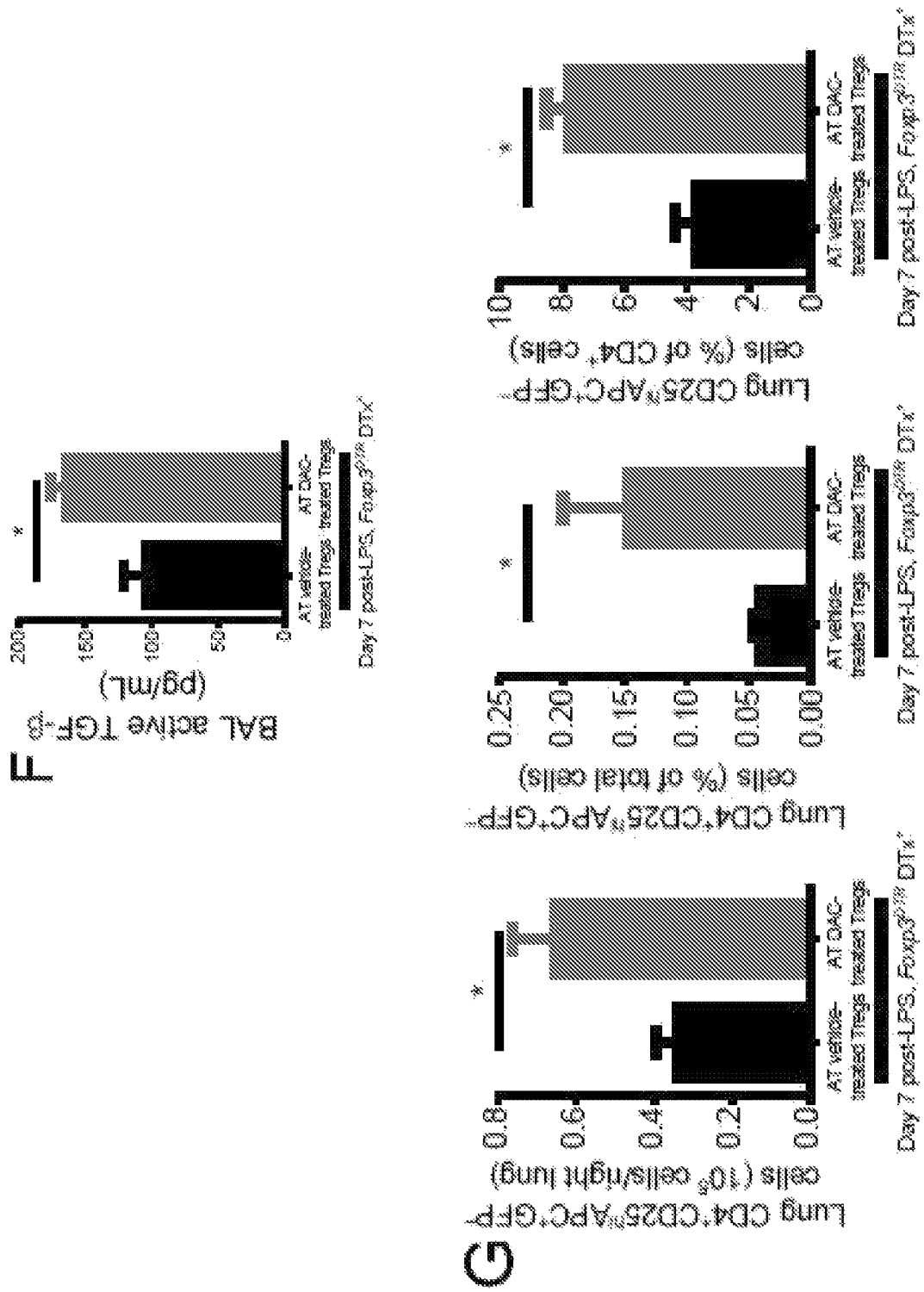

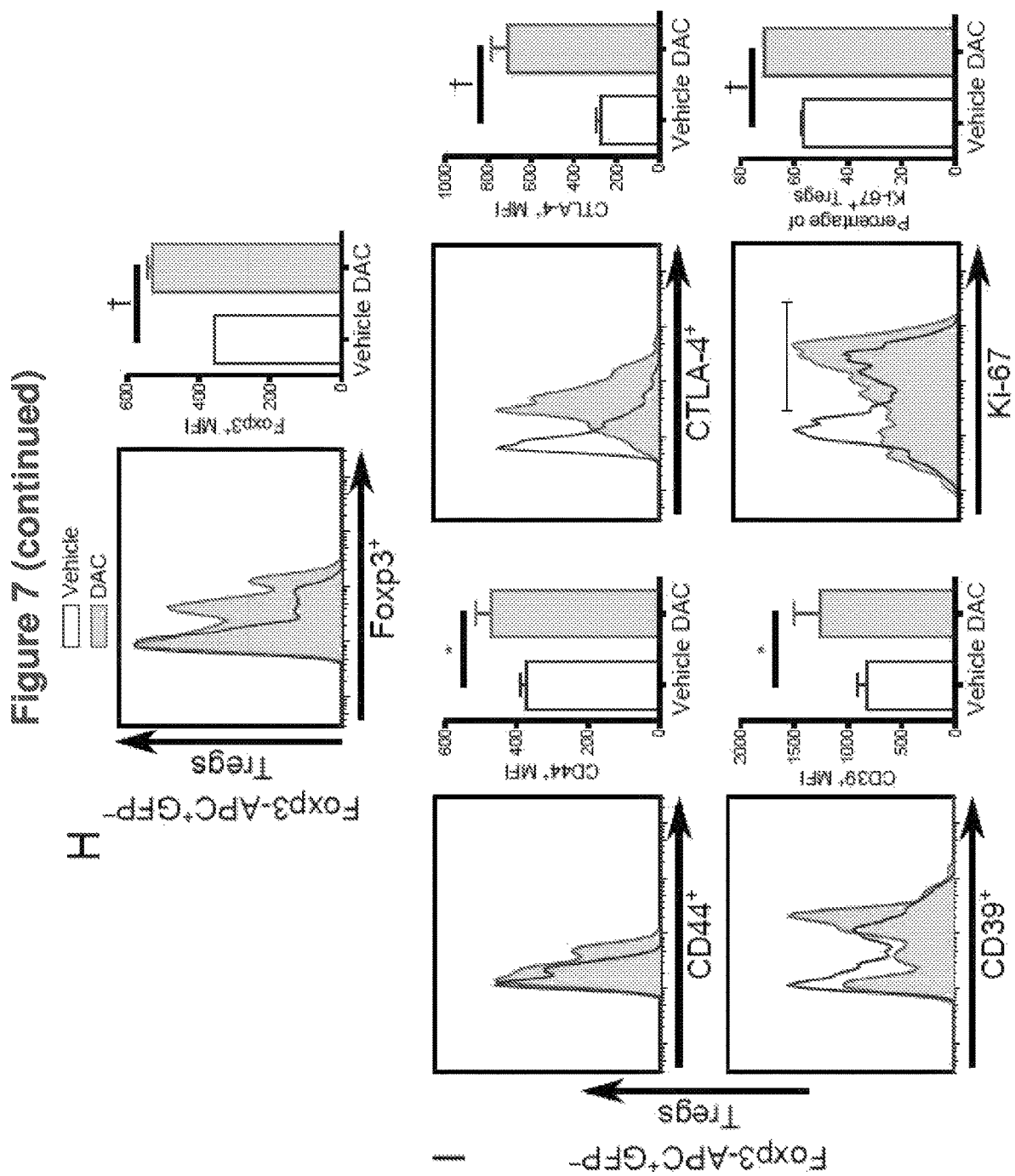

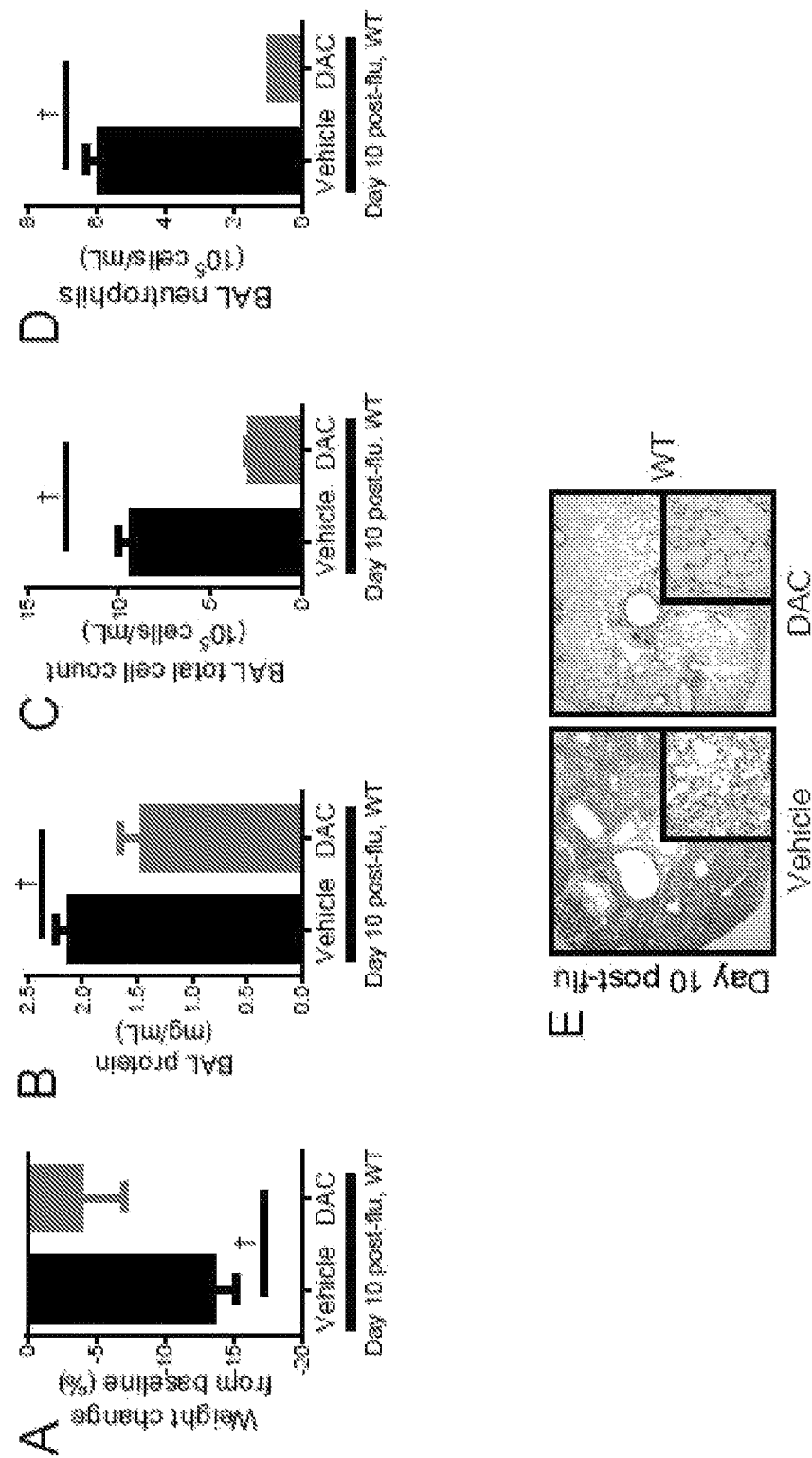

F.

G.

COMPOSITIONS AND METHODS TO ACCELERATE RESOLUTION OF ACUTE LUNG INFLAMMATION

CROSS-REFERENCE TO RELATED APPLICATIONS

This application is the U.S. national stage pursuant to 35 U.S.C. § 371, of International Application Ser. No. PCT/US2016/012621, filed Jan. 8, 2016 and published in English on Jul. 14, 2016 as publication WO 2016/112271 A1, which claims the benefit of priority under 35 U.S.C. § 119(e) to U.S. Provisional Application No. 62/101,319, filed Jan. 8, 2015 and entitled, "Inhibition of DNA Methyltransferase to Accelerate Resolution of Acute Lung Inflammation", and U.S. Provisional Application No. 62/136,199, filed Mar. 20, 2015 and entitled, "IL-4 Therapy to Accelerate Resolution and Repair of Acute Lung Inflammation", both of which are incorporated by reference herein in their entirety.

STATEMENT OF RIGHTS TO INVENTIONS MADE UNDER FEDERALLY SPONSORED RESEARCH

This work was supported by grant numbers R00 HL103973 and F32 HL120400, awarded by the National Heart, Lung, and Blood Institute of the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 3, 2020, is named 048317-462N01US_SL.txt and is 4,260 bytes in size.

FIELD OF THE INVENTION

This invention relates generally to mechanisms that accelerate resolution and repair of lung damage. The invention relates generally to epigenetic mechanisms that enhance regulatory T cell (Tregs) to promote resolution of lung injury/inflammatory lung damage. The invention also relates to the uses of IL-4 (optionally, recombinant IL-4 ("rIL-4")) as an appropriate immunotherapy for lung injury resolution.

INTRODUCTION

Acute respiratory distress syndrome (ARDS), an inflammatory condition caused by direct or indirect lung injury, is a common and life-threatening disease without effective pharmacotherapy (1). Mechanisms leading to resolution and repair from acute lung injury (ALI) and acute respiratory distress syndrome (ARDS) remain incompletely understood. To initiate lung inflammation, alveolar macrophages acquire a M1 phenotype and secrete classical M1 predominant cytokines. Less is known about the alveolar macrophage phenotype during resolution of lung inflammation, and whether and/or how this might impact lung repair. Resolution of inflammation following acute lung injury is an active process (2) that requires Foxp3+ regulatory T cells (Tregs) in a direct lung injury mouse model (intratracheal lipopolysaccharide (LPS) administration (3)). In that model, wild type mice spontaneously resolved their injury 7-10 days after receiving LPS. Lymphocytes did not determine initial injury; however, injury resolution required lymphocytes, as evidenced by unremitting LPS-induced lung inflammation in lymphocyte-deficient recombinase activating gene-1-null (Rag-1$^{-/-}$) mice. Despite extensive investigation into initial events that cause ARDS pathology, no effective therapies (e.g., cellular or pharmacotherapies) are known that promote repair in the damaged lung, at least in part because epigenetic mechanisms that enhance Treg-mediated repair of established lung damage remain unknown.

SUMMARY OF THE INVENTION

The invention is based, at least in part, upon the discovery that administration of a DNA methyltransferase inhibitor, either systemically to a subject or to T cells (Treg cells) in culture for transfer to the subject, exerted a remarkable effect in promoting/enhancing recovery of the subject from lung injury.

The invention is also based, at least in part, upon the discovery that administration of IL-4 to a subject having a lung injury exerted a remarkable effect in promoting/enhancing recovery of the subject from lung injury.

In one aspect, the invention provides a method for treating an acute inflammatory disease or disorder in a subject that involves identifying a subject having an acute inflammatory disease or disorder, and administering a DNA methyltransferase inhibitor to the subject, thereby treating the acute inflammatory disease or disorder in the subject.

In another aspect, the invention provides a method for treating lung injury in a subject that involves identifying a subject having a lung injury, and administering a DNA methyltransferase inhibitor to the subject, thereby treating the lung injury in the subject.

In an additional aspect, the invention provides a method for treating influenza in a subject that involves identifying a subject having influenza, and administering a DNA methyltransferase inhibitor to the subject, thereby treating influenza in the subject.

In one embodiment, the DNA methyltransferase inhibitor is administered in an amount sufficient to increase Treg frequency in the subject. Optionally, the DNA methyltransferase inhibitor is administered in an amount sufficient to increase Foxp3 expression in the Treg cells of the subject.

In another embodiment, the DNA methyltransferase inhibitor is 5-Azacytidine; 5-Aza-2'-deoxycytidine; zebularine; 5-Fluoro-2'-deoxycytidine; 5, 6-Dihydro-5-azacytidine; Hydralazine; Procainamide; Procaine; EGCG ((−)-epigallocatechin-3-gallate); Psammaplin A; MG98; RG108; a DNA methyltransferase-targeting antisense oligonucleotide; or a DNA methyltransferase-targeting RNAi agent. Optionally, the DNA methyltransferase inhibitor is 5-Aza-2'-deoxycytidine (decitabine; DAC).

In one embodiment, the acute inflammatory disease or disorder or lung injury is an acute lung injury, optionally, acute respiratory distress syndrome (ARDS).

In certain embodiments, the subject is a human.

Optionally, the DNA methyltransferase inhibitor is administered to the subject at least 2-3 hours after a lung injury event in the subject, at least 6 hours after a lung injury event in the subject, at least 12 hours after a lung injury event in the subject, at least 24 hours after a lung injury event in the subject, at least 36 hours after a lung injury event in the subject, at least 48 hours after a lung injury event in the subject, at least 72 hours after a lung injury event in the subject, at least four days after a lung injury event in the subject, at least five days after a lung injury event in the subject, at least six days after a lung injury event in the subject, at least seven days after a lung injury event in the subject, at least eight days after a lung injury event in the subject, at least nine days after a lung injury event in the subject, or at least ten days after a lung injury event in the subject.

In one embodiment, the DNA methyltransferase inhibitor is administered to the subject within 1-2 or 1-3 hours after diagnosis of an acute inflammatory disease or disorder, a lung injury event or influenza in the subject, within 6 hours after diagnosis of an acute inflammatory disease or disorder, a lung injury event or influenza in the subject, within 12 hours after diagnosis of an acute inflammatory disease or disorder, a lung injury event or influenza in the subject, within 24 hours after diagnosis of an acute inflammatory disease or disorder, a lung injury event or influenza in the subject, within 36 hours after diagnosis of an acute inflammatory disease or disorder, a lung injury event or influenza in the subject, within 48 hours after diagnosis of an acute inflammatory disease or disorder, a lung injury event or influenza in the subject, within 72 hours after diagnosis of an acute inflammatory disease or disorder, a lung injury event or influenza in the subject, within four days after diagnosis of an acute inflammatory disease or disorder, a lung injury event or influenza in the subject, within five days after diagnosis of an acute inflammatory disease or disorder, a lung injury event or influenza in the subject, within six days after diagnosis of an acute inflammatory disease or disorder, a lung injury event or influenza in the subject, or within seven days after diagnosis of an acute inflammatory disease or disorder, a lung injury event or influenza in the subject.

An additional aspect of the invention provides a method for treating an acute inflammatory disease or disorder in a subject that involves identifying a subject having an acute inflammatory disease or disorder; obtaining a population of cells that includes T cells; administering a DNA methyltransferase inhibitor to the population of cells in vitro, thereby generating a treated population of cells; and administering the treated population of cells to the subject, thereby treating the acute inflammatory disease or disorder in the subject.

Another aspect of the invention provides a method for treating influenza in a subject that involves identifying a subject having influenza; obtaining a population of cells that includes T cells; administering a DNA methyltransferase inhibitor to the population of cells in vitro, thereby generating a treated population of cells; and administering the treated population of cells to the subject, thereby treating influenza in the subject.

In one embodiment, the cells are autologous cells. In another embodiment, the cells are allogeneic cells. Optionally, the cells are isolated from the blood, spleen, thymus and/or lymph of a subject (optionally, the subject being administered the DNA methyltransferase inhibitor-treated cells, though in certain embodiments, a distinct subject than the one to which the DNA methyltransferase inhibitor-treated cells are administered).

In some embodiments, the DNA methyltransferase inhibitor is administered for at least 24 hours to the population of cells in vitro.

Another aspect provides a DNA methyltransferase inhibitor-treated population of cells obtained by a method of the invention.

A further aspect of the invention provides a pharmaceutical composition for the treatment of an acute inflammatory disease or disorder or influenza that includes a DNA methyltransferase inhibitor and a pharmaceutically acceptable carrier.

In one aspect, the invention provides a method for treating an acute inflammatory disease or disorder in a subject, the method involving identifying a subject having an acute inflammatory disease or disorder, and administering an IL-4 polypeptide or fragment thereof possessing cytokine activity, or an IL-4 agonist to the subject, thereby treating the acute inflammatory disease or disorder in the subject.

Another aspect of the invention provides a method for treating a lung injury in a subject, the method involving identifying a subject having a lung injury, and administering an IL-4 polypeptide or fragment thereof possessing cytokine activity, or an IL-4 agonist to the subject, thereby treating the lung injury in the subject.

In an additional aspect, the invention provides a method for treating influenza in a subject that involves identifying a subject having influenza, and administering an IL-4 polypeptide or fragment thereof possessing cytokine activity, or an IL-4 agonist to the subject, thereby treating influenza in the subject.

In a further aspect, the invention provides a method for treating a live bacterial infection in a subject that involves identifying a subject having a live bacterial infection, and administering an IL-4 polypeptide or fragment thereof possessing cytokine activity, or an IL-4 agonist to the subject, thereby treating the live bacterial infection in the subject.

In certain embodiments, the live bacterial infection is *Staphylococcus, Pseudomonas, Streptococcus,* or a combination thereof. Optionally, the live bacterial infection is *Staphylococcus aureus, Pseudomonas aeruginosa, Escherichia coli, Streptococcus pneumoniae, Haemophilus influenzae* or a combination thereof.

In one embodiment, the IL-4 polypeptide or fragment thereof possessing cytokine activity or IL-4 agonist is a recombinant polypeptide.

In another embodiment, the IL-4 polypeptide or fragment thereof possessing cytokine activity or IL-4 agonist is a recombinant IL-4 polypeptide.

In an additional embodiment, the recombinant IL-4 polypeptide is selected from the group consisting of a recombinant murine IL-4 of SEQ ID NO: 1 or a fragment thereof possessing cytokine activity and a recombinant human IL-4 of SEQ ID NO: 3 or a fragment thereof possessing cytokine activity.

In an additional embodiment, the acute inflammatory disease or disorder or lung injury is an acute lung injury. Optionally, the acute inflammatory disease or disorder or lung injury is acute respiratory distress syndrome (ARDS).

In one embodiment, the subject is human.

In certain embodiments, the IL-4 polypeptide or fragment thereof possessing cytokine activity or IL-4 agonist in an amount sufficient to promote transition of lung (e.g., alveolar) macrophages from an M1 phenotype to M2 phenotype.

Optionally, the IL-4 polypeptide or fragment thereof possessing cytokine activity or IL-4 agonist is administered to the subject at least 2-3 hours after a lung injury event in the subject, at least 6 hours after a lung injury event in the subject, at least 12 hours after a lung injury event in the subject, at least 24 hours after a lung injury event in the subject, at least 36 hours after a lung injury event in the subject, at least 48 hours after a lung injury event in the subject, at least 72 hours after a lung injury event in the subject, at least four days after a lung injury event in the subject, at least five days after a lung injury event in the subject, at least six days after a lung injury event in the subject, at least seven days after a lung injury event in the subject, at least eight days after a lung injury event in the subject, at least nine days after a lung injury event in the subject, or at least ten days after a lung injury event in the subject.

In one embodiment, the IL-4 polypeptide or fragment thereof possessing cytokine activity or IL-4 agonist is administered to the subject within 1-2 or 1-3 hours after diagnosis of an acute inflammatory disease or disorder, a lung injury event or influenza in the subject, within 6 hours after diagnosis of an acute inflammatory disease or disorder, a lung injury event or influenza in the subject, within 12 hours after diagnosis of an acute inflammatory disease or disorder, a lung injury event or influenza in the subject, within 24 hours after diagnosis of an acute inflammatory disease or disorder, a lung injury event or influenza in the subject, within 36 hours after diagnosis of an acute inflammatory disease or disorder, a lung injury event or influenza in the subject, within 48 hours after diagnosis of an acute inflammatory disease or disorder, a lung injury event or influenza in the subject, within 72 hours after diagnosis of an acute inflammatory disease or disorder, a lung injury event or influenza in the subject, within four days after diagnosis of an acute inflammatory disease or disorder, a lung injury event or influenza in the subject, within five days after diagnosis of an acute inflammatory disease or disorder, a lung injury event or influenza in the subject, within six days after diagnosis of an acute inflammatory disease or disorder, a lung injury event or influenza in the subject, or within seven days after diagnosis of an acute inflammatory disease or disorder, a lung injury event or influenza in the subject.

An additional aspect of the invention provides a pharmaceutical composition for the treatment of an acute inflammatory disease or disorder that includes an IL-4 polypeptide or fragment thereof possessing cytokine activity or IL-4 agonist and a pharmaceutically acceptable carrier.

Other aspects of the invention are described in, or are obvious from, the following disclosure, and are within the ambit of the invention.

BRIEF DESCRIPTION OF THE DRAWINGS

In FIG. 1A, Lung CD4+ CD25+ Foxp3+ cells are shown in wild type (WT) mice as a frequency of total lung cells five days after receiving intratracheal (i.t.) water. Lung CD4+CD25$^{hi}$Foxp3+ cells are shown in wild type (WT) mice as number in the right lung, frequency of lung cells, and frequency of CD4+ cells five days after receiving intratracheal (i.t.) water. In FIG. 1B, Foxp3 expression was determined by fluorescence in lung Tregs five days after i.t. water; values reported are mean fluorescence intensities±SEM. The accompanying bar graph shows summary mean fluorescence intensities. In FIGS. 1C and 1D, BAL total protein (FIG. 1C) and lung histology in H&E (FIG. 1D) are shown five days post-i.t. water. Original magnification: ×20; ×200 (insets). n=5 per group; *P<0.05, †P<0.001, Mann-Whitney U test. Values reported are mean±SEM.

In FIG. 2A, body weight relative to baseline was plotted after injury. In FIGS. 2B to 2D, BAL total protein (B), total cell counts (C), and neutrophil counts (D) were determined in WT mice two and five days after injury with intratracheal (i.t.) LPS. In FIG. 2E, lung sections two and five days after injury were stained with H&E. Original magnification: ×20; ×200 (insets). n=8 per group; *P<0.05, †P<0.001, Mann-Whitney U test. Values reported are mean±SEM.

In FIG. 3A, left panel, lung CD4+ CD25$^{hi}$Foxp3+ cells are shown within a fixed sample of cells from the right lung (10$^5$ cells) two and five days post-injury in WT mice; in FIG. 3A, middle panel, lung CD4+ CD25$^{hi}$Foxp3+ cells are shown as a frequency of total lung cells two and five days post-injury in WT mice; and in FIG. 3A, right panel, lung CD4+ CD25$^{hi}$Foxp3+ cells are shown as a percentage of total CD4+ cells two and five days post-injury in WT mice. In FIGS. 3B to 3D, Foxp3 (B), CD44, CD39 and CTLA-4 (C) expression, and the percentage of Ki-67+ Tregs (D) were determined by fluorescence in lung Tregs five days after injury. Accompanying bar graphs show summary mean fluorescence intensities (B and C) and the percentage of of Ki-67+ Tregs (D). n=8 per group; *P<0.05, **P<0.01, †P<0.001, Mann-Whitney U test for cell numbers/frequencies (A and D); or t-test with Holm-Sidak correction for multiple comparisons (mean fluorescence intensities, B and C). Values reported are mean±SEM.

In FIG. 4A, body weight relative to baseline was plotted after injury. In FIGS. 4B to 4D, BAL total protein (B), total cell counts (C), and neutrophil counts (D) were determined in Rag-1−/− mice five days after injury with LPS. In FIG. 4E, lung sections were stained with H&E. Original magnification: ×20; ×200 (insets). n=5 per group; P>0.05, Mann-Whitney U test. Values reported are mean±SEM.

In FIG. 5A, body weight relative to baseline was plotted beginning with the first diphtheria toxin dose (two days before injury). Arrowheads represent diphtheria toxin (DTx) doses. In FIGS. 5B to 5D, BAL total protein (B), total cell counts (C), and neutrophil counts (D) were determined in diphtheria toxin-treated Foxp3DTR mice (Foxp3DTR DTx+) five days after injury with LPS. In FIG. 5E, lung sections were stained with H&E. Original magnification: ×20; ×200 (insets). n=7 per group; P>0.05, Mann-Whitney U test. Values reported are mean±SEM.

In FIG. 6A, splenic WT CD4+ CD25− conventional T cells (Tconv) or Tregs were cultured with indicated amounts of DAC for 48 hours. Foxp3 fluorescence was plotted for indicated DAC concentrations (vehicle/0, 10, and 100 nM). In FIGS. 6B and 6C, CD4+CD25$^{hi}$Foxp3+ Treg expression of CD44, CD39, and CTLA-4 (B) and the percentage of total Ki-67+ Tregs (C) were determined by fluorescence in cultured Tregs treated with 100 nM DAC or vehicle. Accompanying bar graphs show summary mean fluorescence intensities (FIGS. 6A and 6B) and the percentage of Ki-67+ Tregs (FIG. 6C). In FIG. 6D, T effector cells (Teff) were sorted from WT spleens, labeled with CellTrace Violet, and cultured in the presence of anti-CD3/CD28 and varying Treg ratios. Tregs were previously cultured in the presence of 100 nM DAC or vehicle. In FIG. 6E, the global DNA methylation was measured in Tregs cultured with vehicle or 100 nM DAC and compared with methylated control. The significant decrease in the proportion of methylated DNA (relative to methylated control DNA) is shown for 100 nM treatment with DAC, as compared to treatment with vehicle control.

Figure 6:
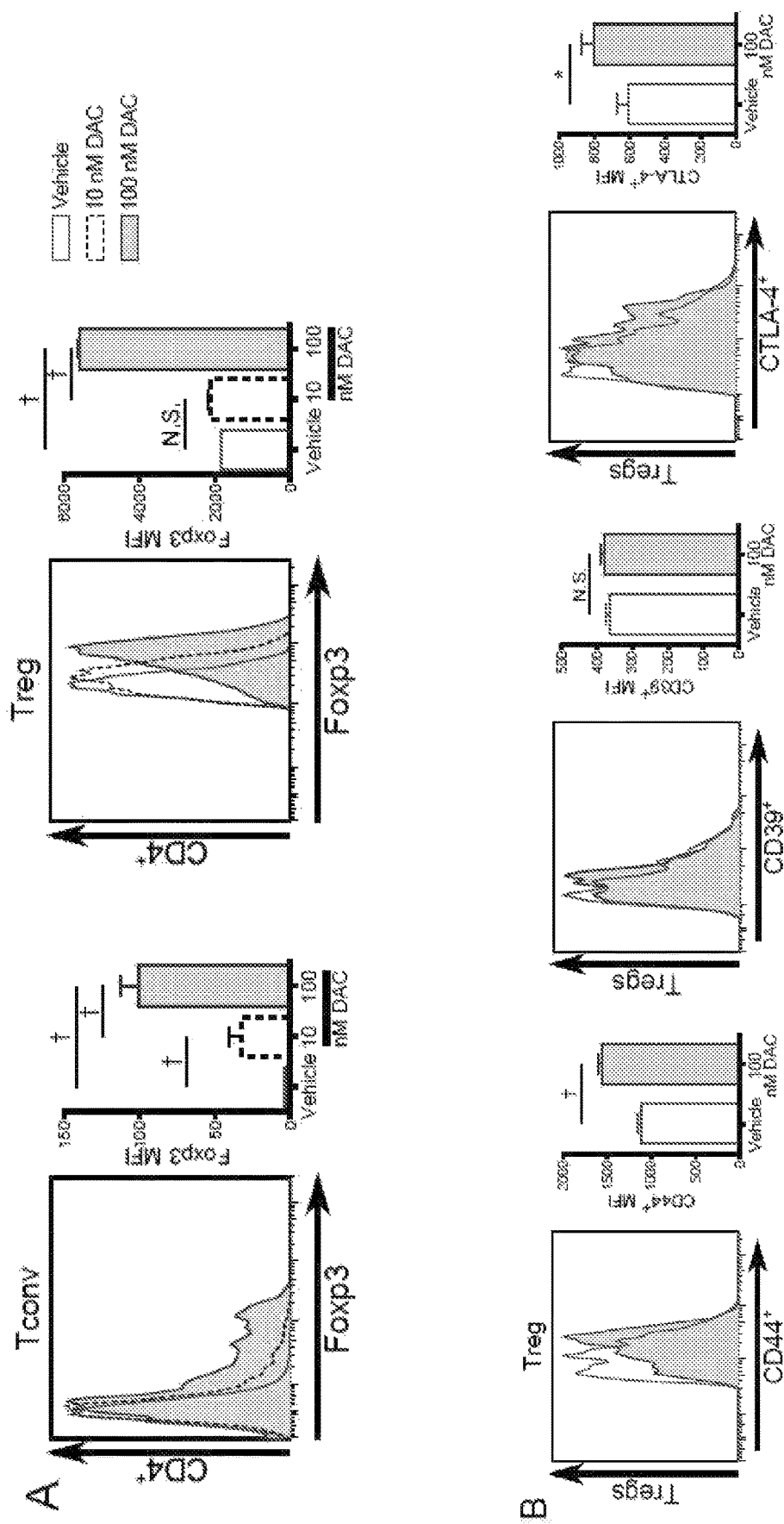
FIGS. 6A to 6E demonstrate that DAC altered CD4+ T cell phenotype and function in vitro.
Figure 6:
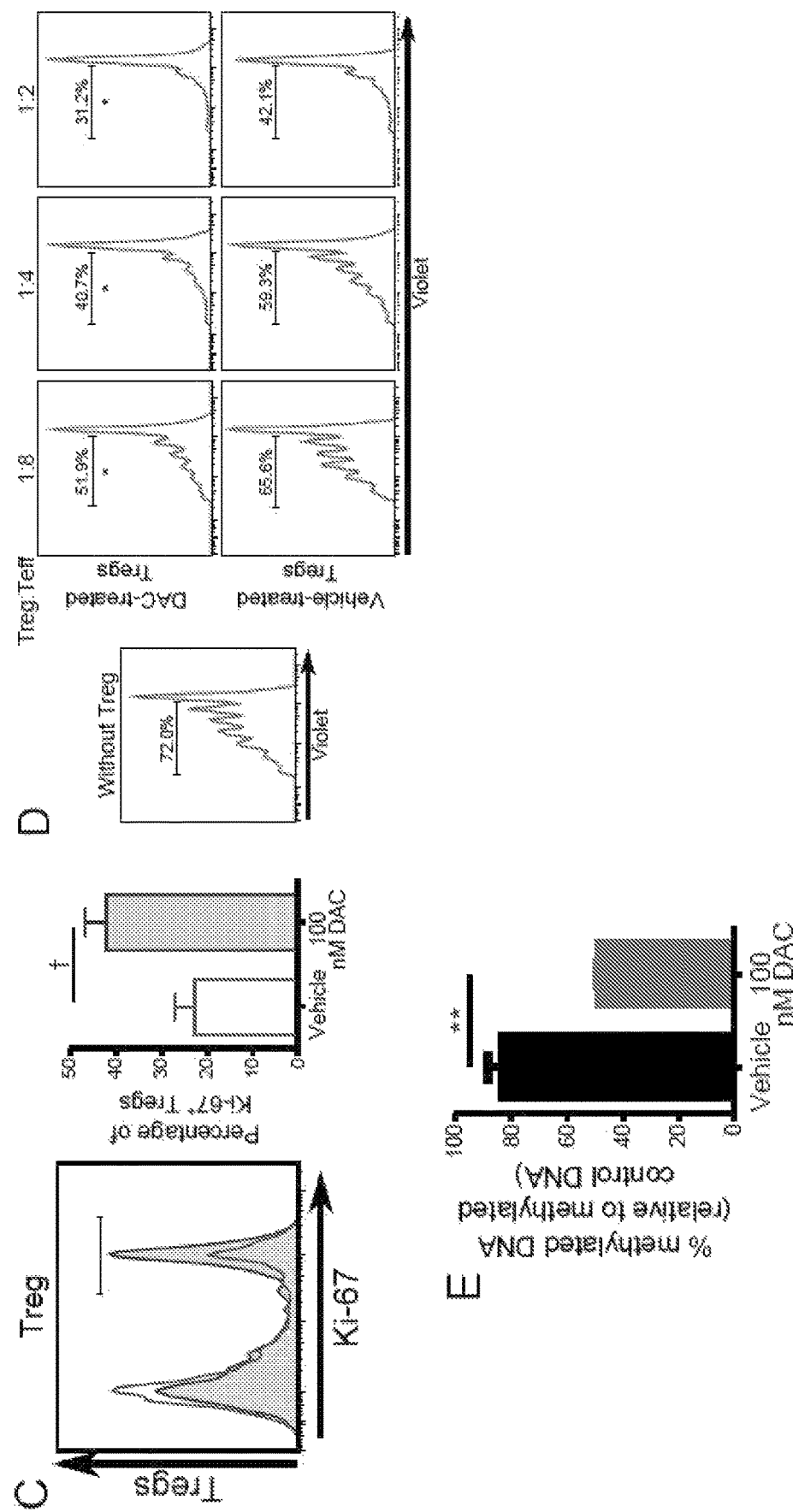

Experiments were conducted in triplicate and repeated three times. Proliferation data are representative of three independent experiments. *P<0.05, **P<0.01, †P<0.001, t-test with Holm-Sidak correction for multiple comparisons (mean fluorescence intensity, FIGS. 6A and 6B) or Mann-Whitney U test (Ki-67 percent positivity, FIGS. 6C to 6E). Values reported are mean±SEM.

Figure 7:
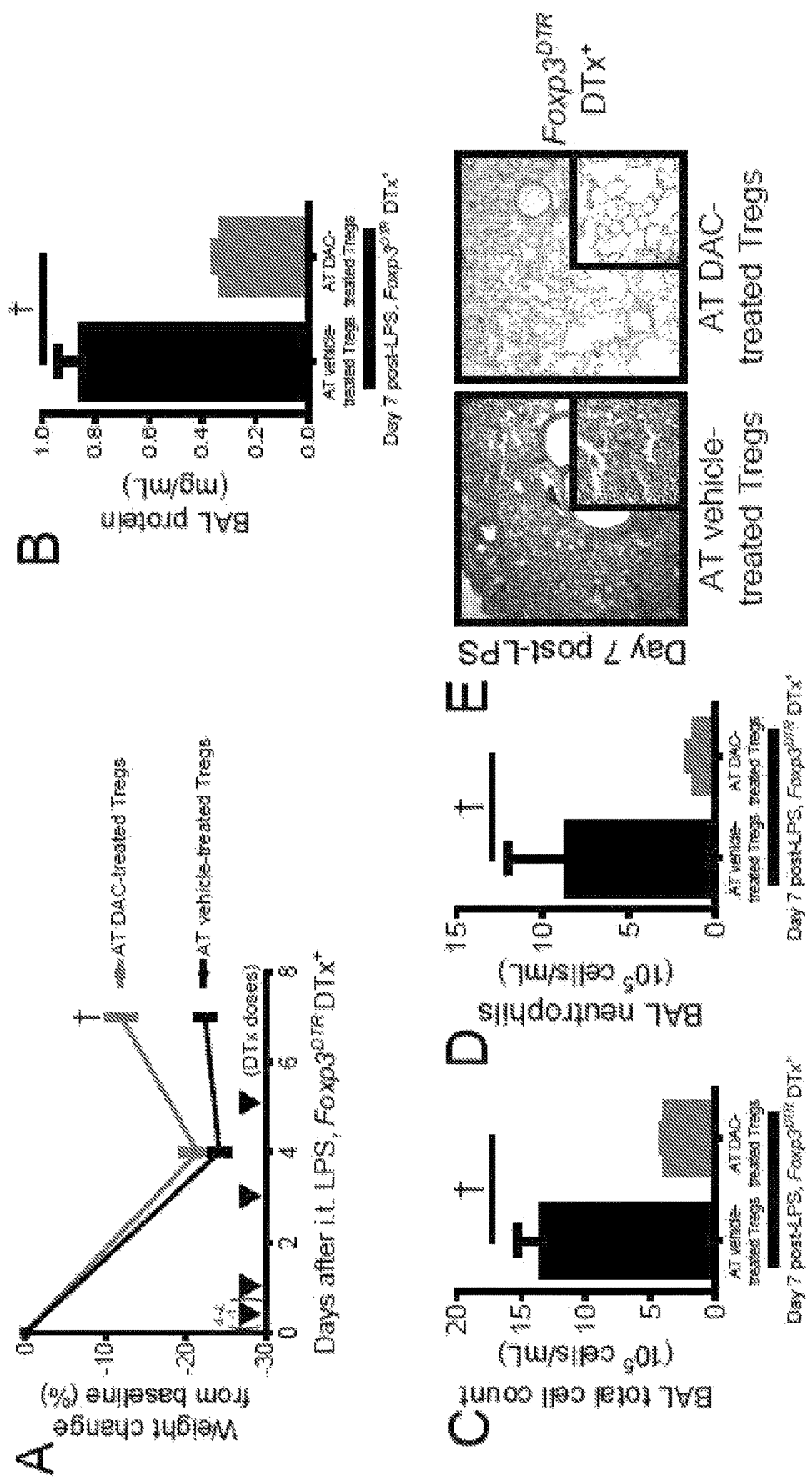

FIGS. 7A to 7I demonstrate that adoptive transfer (AT) of DAC-treated Tregs rescued the injury phenotype in Treg-depleted mice (Foxp3DTR DTx+). In FIG. 7A, body weight relative to baseline was plotted after injury. Arrowheads represent diphtheria toxin (DTx) doses. In FIGS. 7B to 7D, BAL total protein (B), total cell counts (C), and neutrophil counts (D) were determined in Treg-depleted mice seven days after injury with LPS. In FIG. 7E, lung sections seven days after injury were stained with H&E. Original magnification: ×20; ×200 (insets). In FIG. 7F, BAL active TGF-β was assessed in vehicle- and DAC-treated Tregs at seven days post-injury. TGF-β concentrations were measured in BAL fluid. FIG. 7G shows that exogenous lung Tregs (Foxp3-APC+ GFP−; i.e. CD4+CD25$^{hi}$APC+GFP−) are shown as number in the right lung, frequency of lung cells, and frequency of CD4+ cells seven days post-injury. Exogenous lung Tregs were significantly elevated in DAC-treated Treg populations, when assessed in a fixed number of cells (left panel), as a percentage of total cell count (middle panel), or as a percentage of CD4$^+$ cells (right panel). In FIGS. 7H and 7I, Foxp3 (H) and CD44, CD39, CTLA-4 expression, and the percentage of Ki-67+ Tregs (I) were determined by fluorescence in exogenous (APC+ GFP−) lung Tregs seven days after injury. Accompanying bar graphs show summary mean fluorescence intensities (FIGS. 7H and 7I) and the percentage of Ki-67+ Tregs (FIG. 7I, last panel). n=6 per group; *P<0.05, †P<0.001, Mann-Whitney U test (lung injury parameters, TGF-β levels, and cell numbers/frequencies, FIGS. 7A-7D and FIGS. 7F, 7G and I [last panel]) or t-test with Holm-Sidak correction for multiple comparisons (mean fluorescence intensity, FIGS. 7H and 7I [first three panels]). Values reported are mean±SEM.

Figure 8:
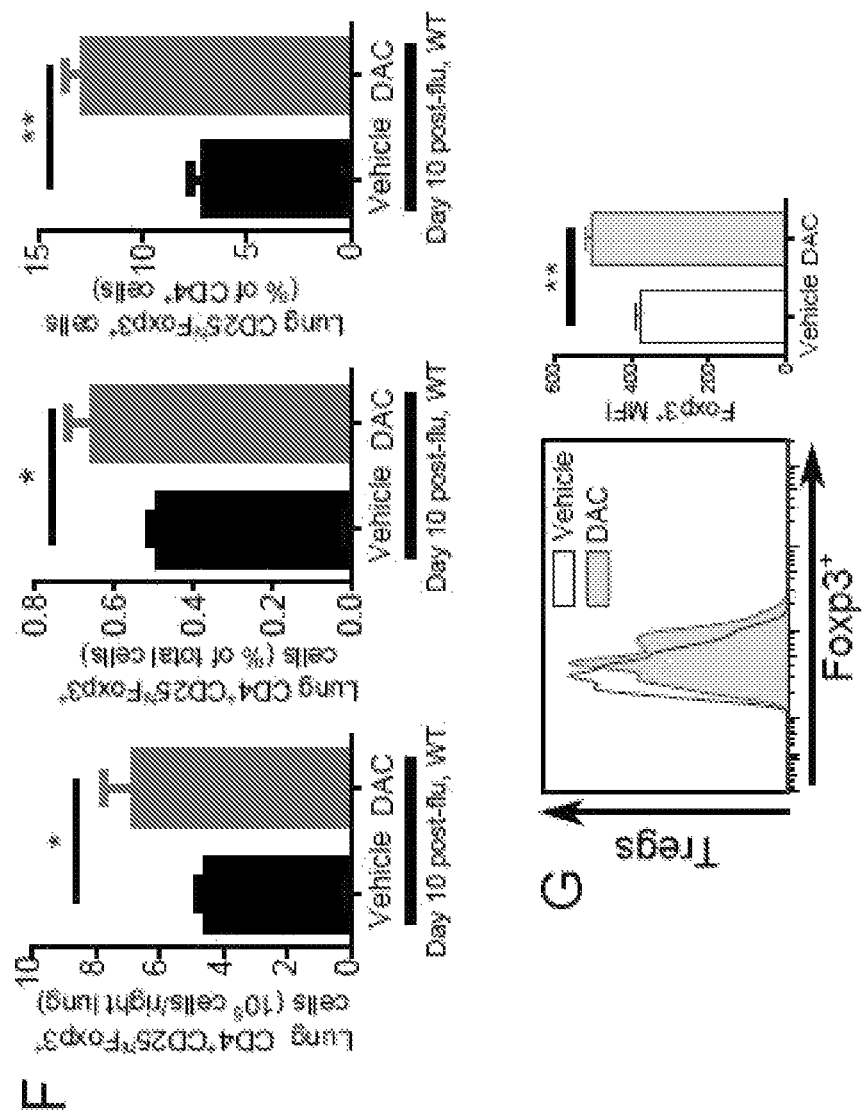

FIGS. 8A to 8G show that DAC rescue treatment had favorable effects in an influenza (flu) model. FIGS. 8A to 8G demonstrate the significant, beneficial impact of DAC treatment upon weight (FIG. 8A), BAL levels (FIGS. 8B to 8D) histological recovery from influenza (FIG. 8E), and Treg levels (FIGS. 8F and 8G) in a mouse model of influenza challenge. In FIG. 8A, body weight relative to baseline is shown 10 days after inoculation with influenza. In FIGS. 8B to 8D, BAL total protein (FIG. 8B), total cell counts (FIG. 8C) and neutrophil counts (FIG. 8D) were determined in WT mice 10 days after inoculation with i.t. influenza. In FIG. 8E, lung sections 10 days after inoculation were stained with H&E. Original magnification, ×20; ×200 (insets). In FIG. 8F, lung CD4+CD25$^{hi}$Foxp3+ cells are shown as number in the right lung, frequency of lung cells, and frequency of CD4+ cells 10 days post-inoculation. In FIG. 8G, Foxp3 expression was determined by fluorescence in lung Tregs. The accompanying bar graph shows summary mean fluorescence intensities. N=9 per group; *P<0.05, **P<0.01, †P<0.001, Mann-Whitney U test. Values reported are mean±SEM.

Figure 9:
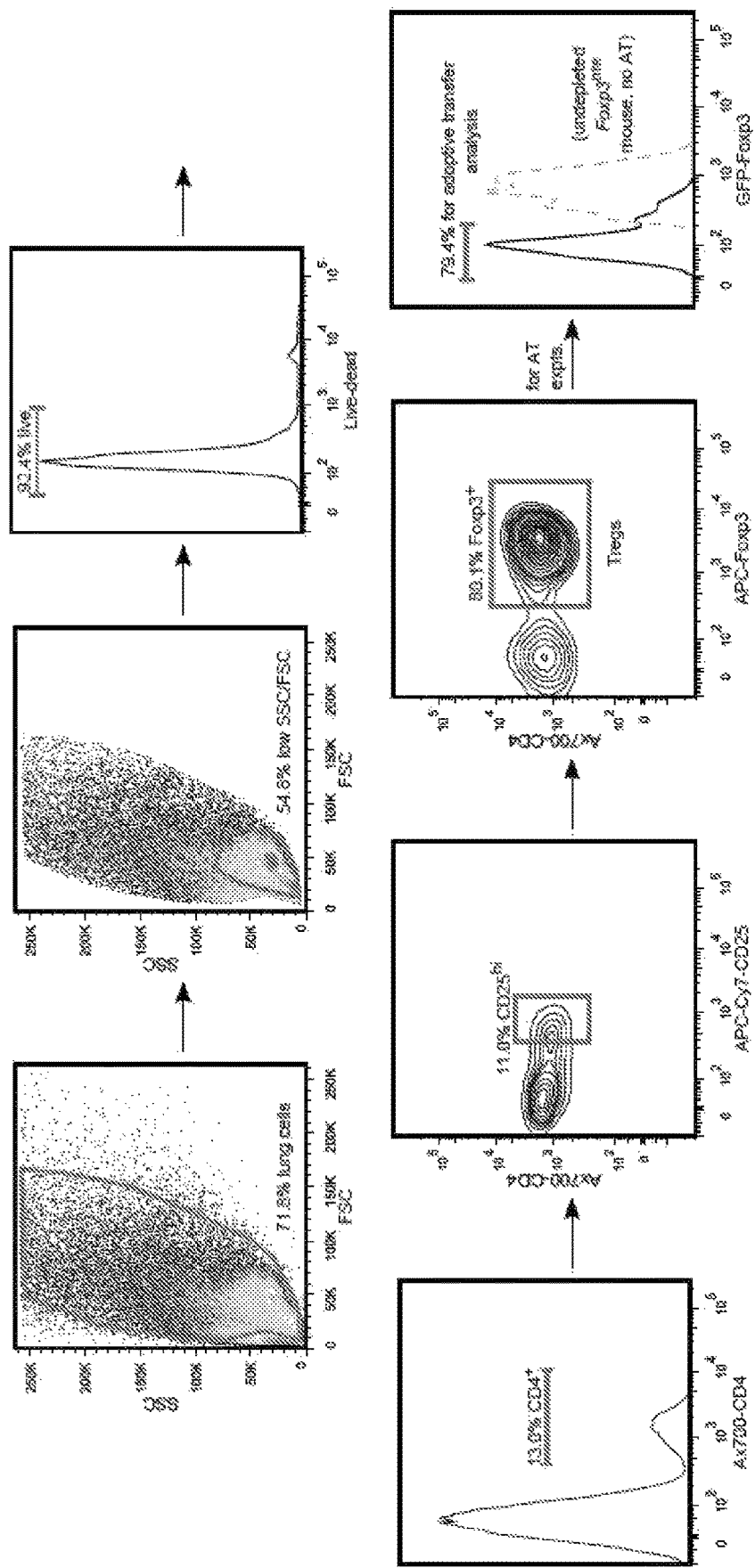

FIG. 9 shows that flow cytometry confirmed successful adoptive transfer and homing to the lung. FIG. 9 is an example analysis of lung single cell suspension. Cells were first gated based on SSC/FSC (side scatter/forward scatter, the distribution of cells based on intracellular composition and size, respectively) to remove debris and gate on the characteristic low SSC/FSC of lymphocytes. Live cells were identified using a UV-excitable dead cell dye. CD4+, CD4+ CD25$^{hi}$, and CD4+CD25$^{hi}$Foxp3+ cells (Tregs) were gated as shown. The GFP− (exogenous) cell fraction was identified following adoptive transfer (AT); for comparison, the dashed histogram shows an undepleted Foxp3DTR mouse that did not receive adoptive transfer. Biexponential scaling was used when more than 5% of events fell on the axis. Histograms were generated as percent of maximum.

Figure 10:
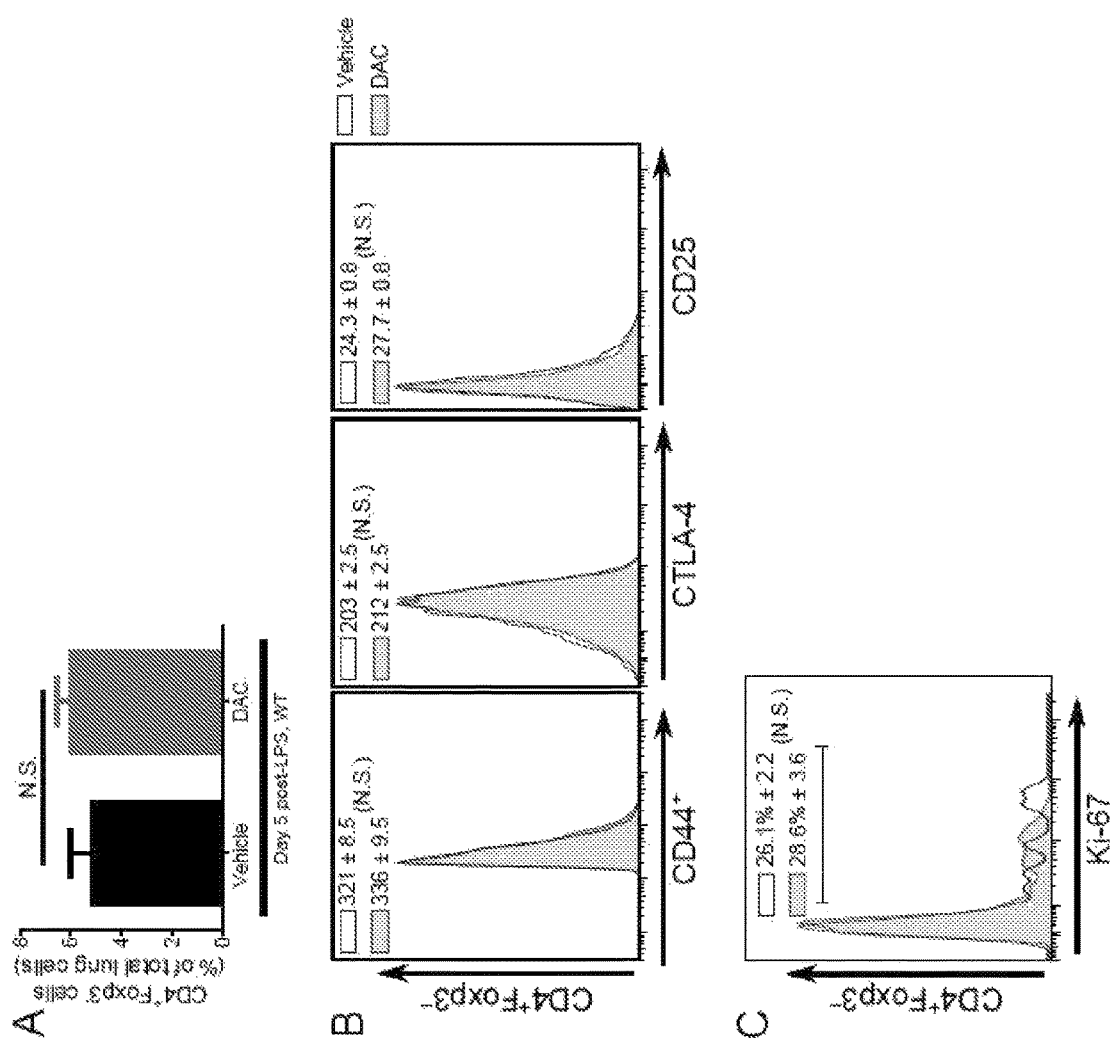

FIGS. 10A to 10C show that DAC treatment did not affect lung CD4+Foxp3− cell frequency or phenotype. Systemic DAC treatment does not affect lung CD4+Foxp3− cells after injury. In FIG. 10A, lung CD4$^+$Foxp3$^−$ cells are shown as a frequency of lung cells five days post-injury in WT mice. In FIG. 10B, CD44, CTLA-4, and CD25 expression were determined by fluorescence in lung CD4$^+$Foxp3$^−$ cells five days after injury. In FIG. 10C, the percentage of Ki-67+ cells is shown for the same cell population. n=8 per group; P>0.05, Mann-Whitney U test (cell numbers/frequencies, FIGS. 10A and 10C) or t-test with Holm-Sidak correction for multiple comparisons (mean fluorescence intensities, FIG. 10B). Values reported are mean±SEM.

Figure 11:
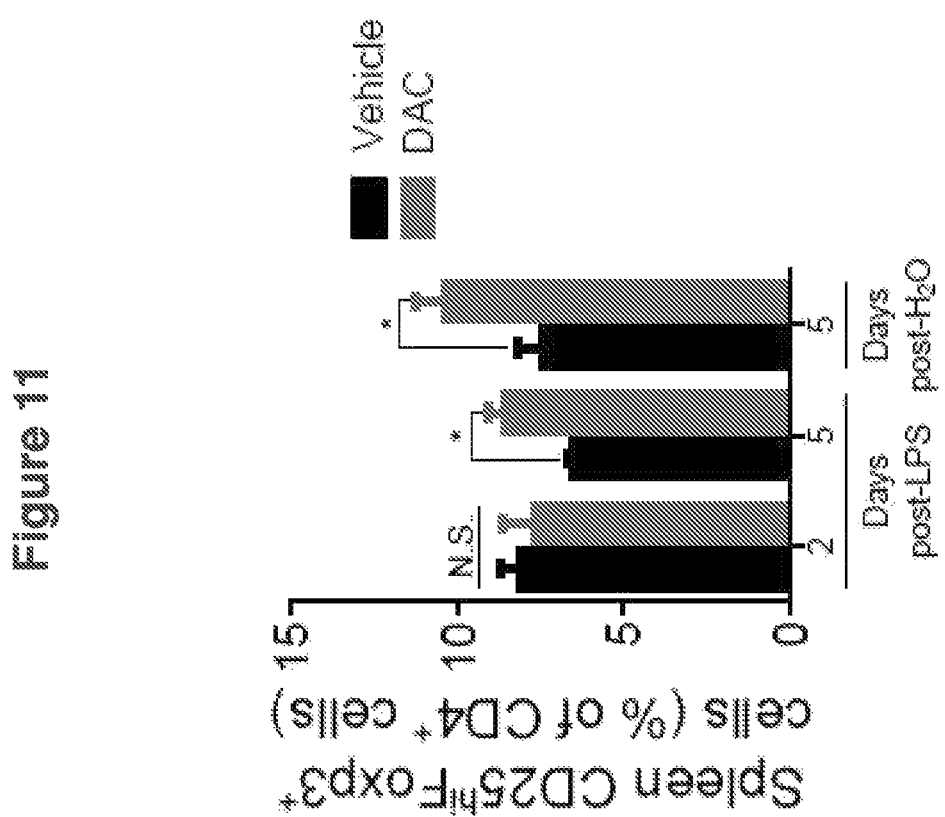

FIG. 11 shows that DAC treatment significantly elevated spleen Treg levels, at either five days post-LPS challenge or at five days post-water treatment. Systemic DAC treatment affected splenic Treg frequency. CD25$^{hi}$Foxp3+ cells are shown as a frequency of splenic CD4+ cells two and five days after i.t. LPS and five days post i.t. water. n=8 per group for LPS and 5 per group for water; *P<0.05, Mann-Whitney U test. Values reported are mean±SEM.

Figure 12:
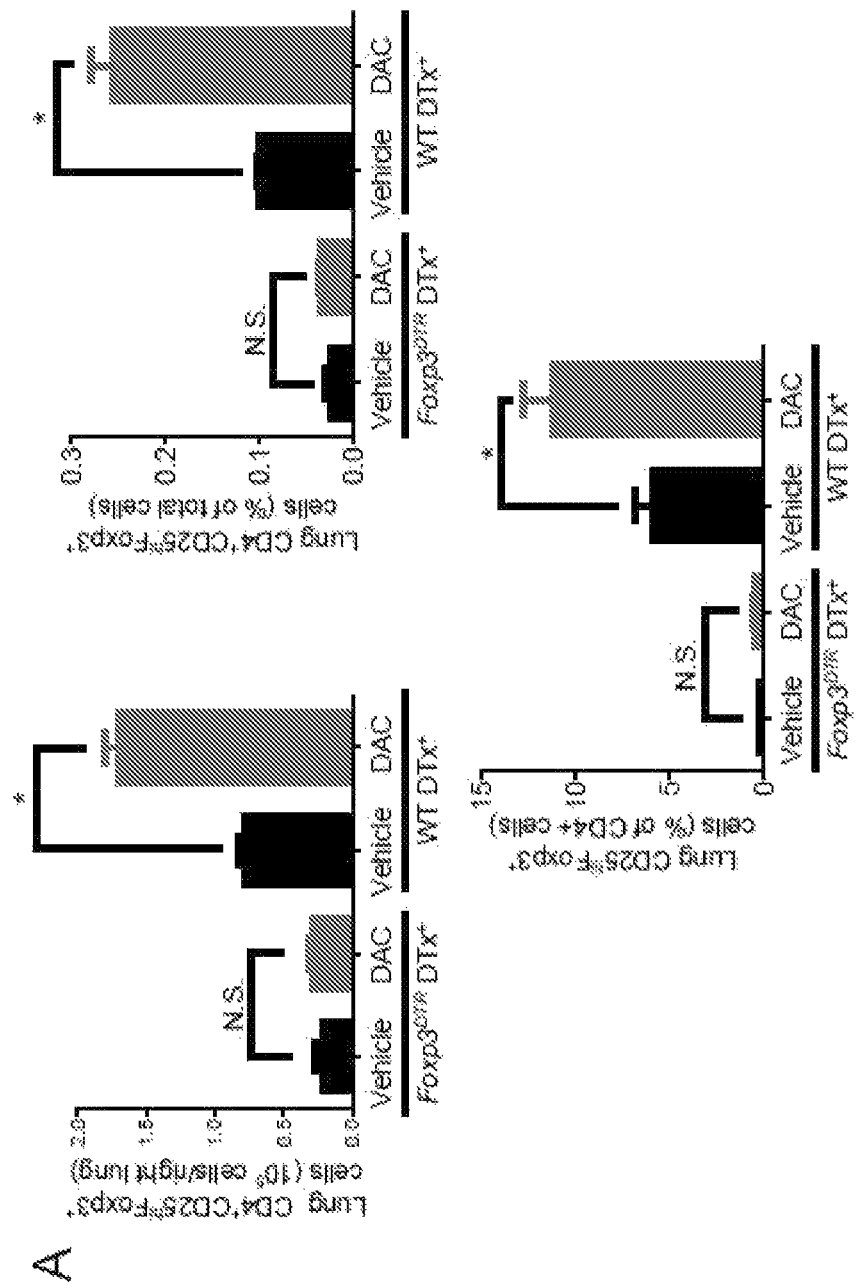
Figure 12:
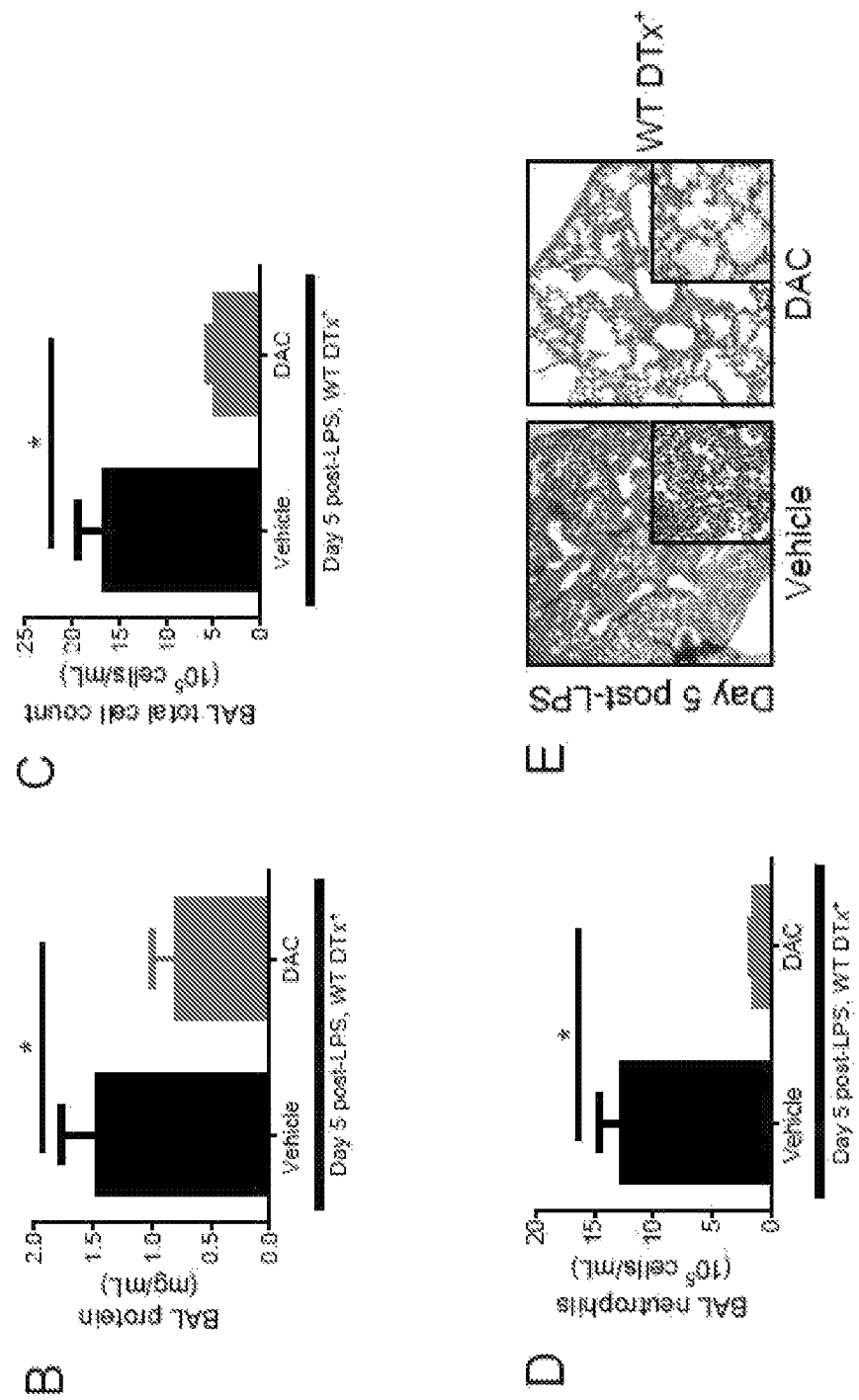

FIGS. 12A to 12E show lung Treg depletion in diphtheria toxin-treated Foxp3DTR mice compared to diphtheria toxin-treated LPS-injured WT mice 5 days post-injury (FIG. 12A). WT mice treated with diphtheria toxin experienced accelerated lung injury resolution in response to DAC (FIGS. 12B to 12E). DAC promoted lung injury resolution in diphtheria toxin-treated WT mice. FIG. 12A shows lung CD4+ CD25$^{hi}$Foxp3+ cells as number in the right lung, frequency of lung cells, and frequency of CD4+ cells five days post-injury in diphtheria toxin-treated Foxp3DTR mice (Foxp3DTR DTx+) and diphtheria toxin-treated wild type mice (WT DTx+). FIGS. 12B to 12D shows BAL total protein (FIG. 12B), total cell counts (FIG. 12C), and neutrophil counts (FIG. 12D) were determined in diphtheria toxin-treated WT mice five days after injury with LPS. In FIG. 12E, lung sections were stained with H&E. Original magnification, ×20; ×200 (insets). n=5 per group; *P<0.05, Mann-Whitney U test. Values reported are mean±SEM.

Figure 13:
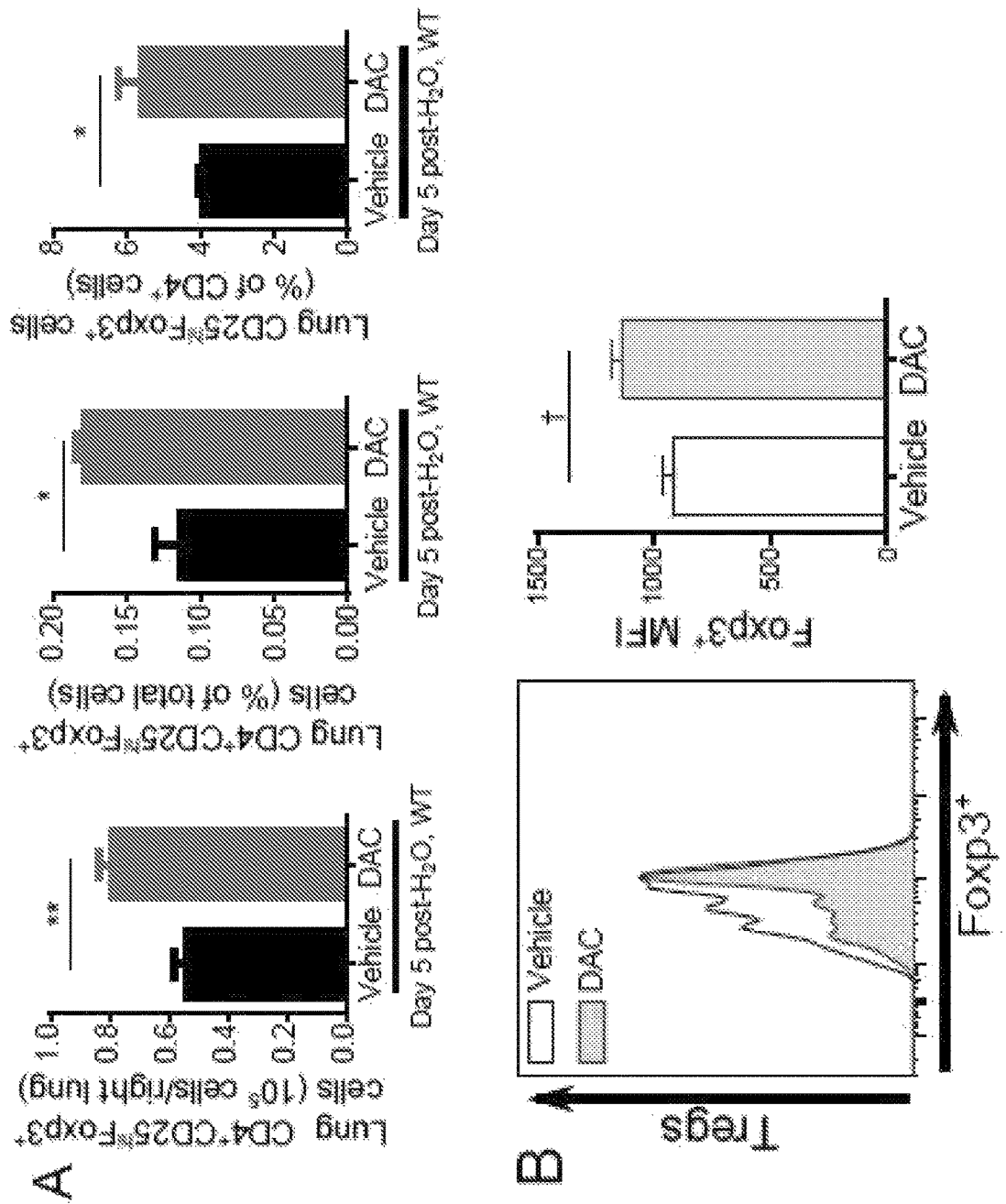

FIGS. 13A and 13B show that DAC increased lung Treg number and Foxp3 expression under sham injury conditions. In FIG. 13A, lung CD4+CD25$^{hi}$Foxp3+ cells are shown in wild type (WT) mice as number in the right lung, frequency of lung cells, and frequency of CD4+ cells five days after receiving intratracheal (i.t.) water. In FIG. 13B, Foxp3 expression was determined by fluorescence in lung Tregs five days after i.t. water. The accompanying bar graph shows summary mean fluorescence intensities. *P<0.05, †P<0.001, Mann-Whitney U test. Values reported are mean±SEM.

Figure 14:
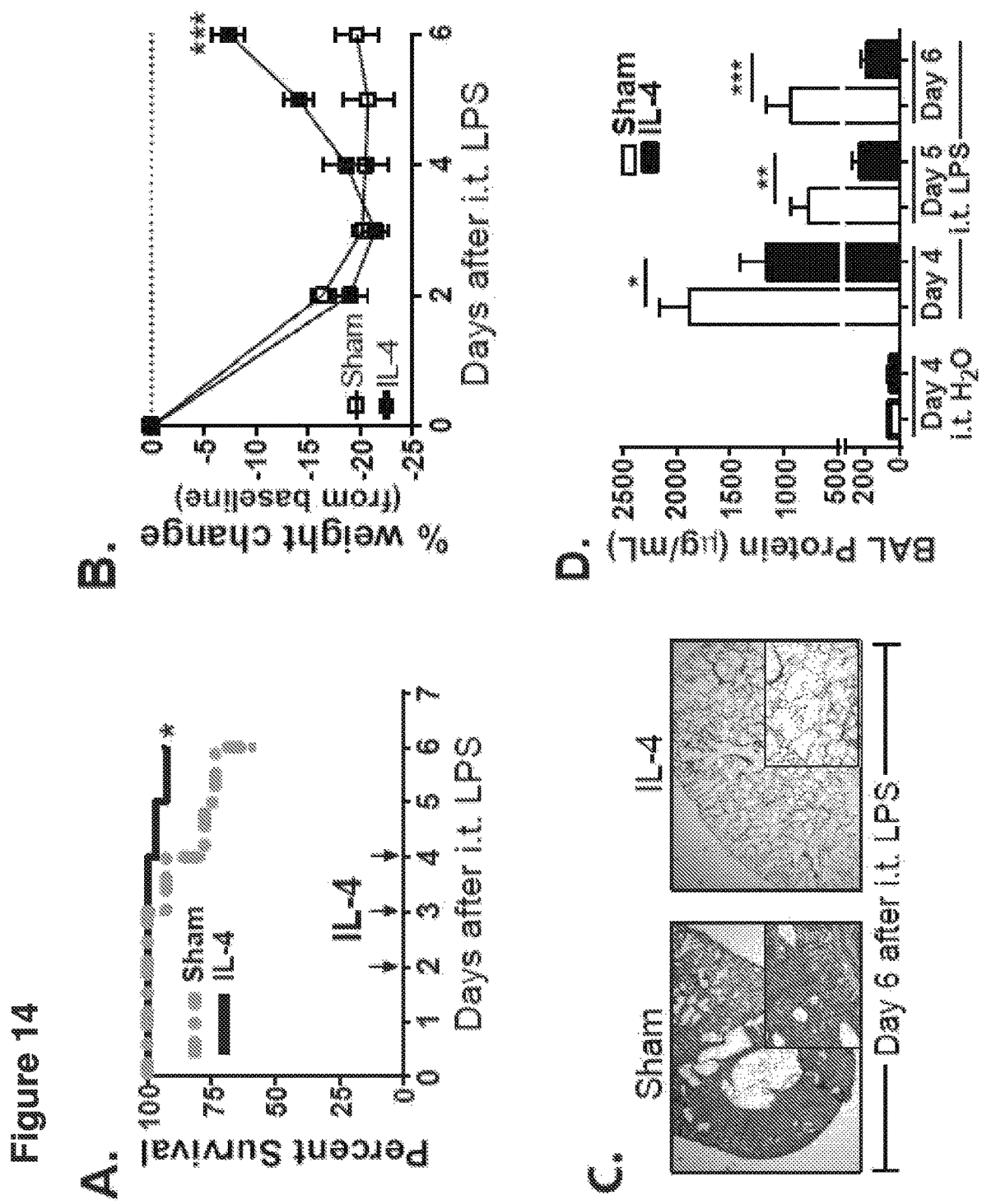
Figure 14:
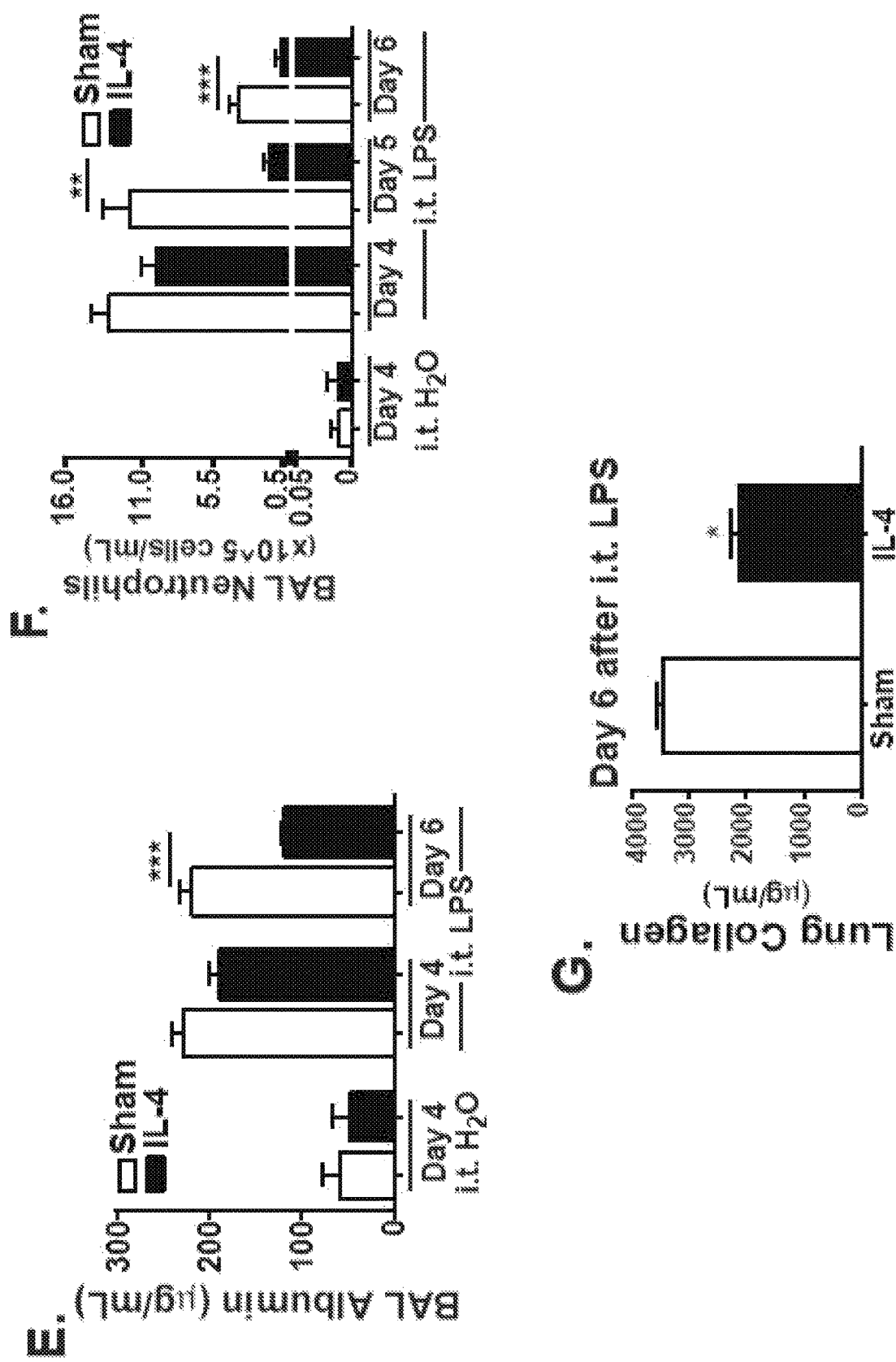
Figure 14:
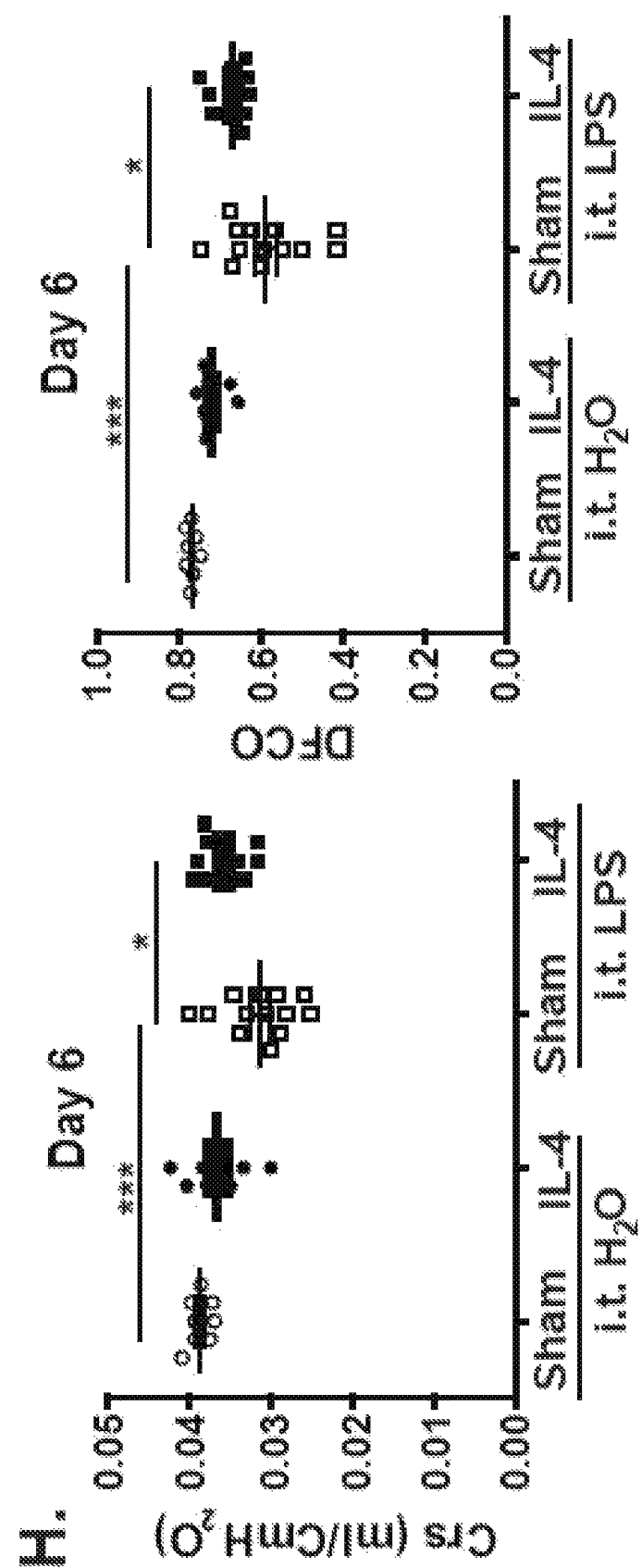

FIGS. 14A to 14H show that WT (C57BL/6) mice treated with IL-4 demonstrated improved survival and accelerated ALI resolution. FIG. 14A shows Kaplan-Meier survival curves for mice exposed to i.t. LPS (4 mg/kg) and treated with IL-4 or sham (n=27-30, p=0.006 by Mantel-Cox). FIG. 14B shows daily percent weight change from baseline for each group following i.t. LPS (n=6-10, ***p<0.001 by repeated-measures ANOVA). FIG. 14C shows representative H&E stain of the lung at day 6 after i.t. LPS in sham- or IL-4-treated mice at 4× and 20× (inserts) magnification.

FIGS. 14D-14F shows BAL protein (FIG. 14D) and BAL albumin (FIG. 14E) values, as well as BAL neutrophil numbers (FIG. 14F) at day 4 in i.t. H2O-exposed mice, or at days 4-6 in i.t. LPS-exposed mice (n=4 for i.t. H2O groups, 6-10 for i.t. LPS groups, *p<0.05, **p<0.01 by one-way ANOVA). FIG. 14G shows lung collagen at day 6 following i.t. LPS (n=5-6, *p<0.05) FIG. 14H shows dynamic lung compliance (Crs, ml/cmH2O) and diffusing capacity (DFCO) after i.t. LPS or i.t. H2O (n=8-12, *p<0.05, ***p<0.001 by one-way ANOVA).

FIGS. 15A to 15E show that following i.t. LPS exposure, blocking IL-4 delayed endogenous ALI resolution. Parameters of ALI and resolution including: BAL protein (FIG. 15A), neutrophils (FIG. 15B), and macrophages (FIG. 15C) quantified at day 6 after i.t. LPS. Percent-positive and MFI expression of the M2 macrophage markers MMR and Dectin-1 (FIG. 15D) and the M1 marker CD86 (FIG. 15E) among F4/80+ macrophages are shown. (n=4-5, p<0.01 and *p<0.001 by t-test).

Figure 16:
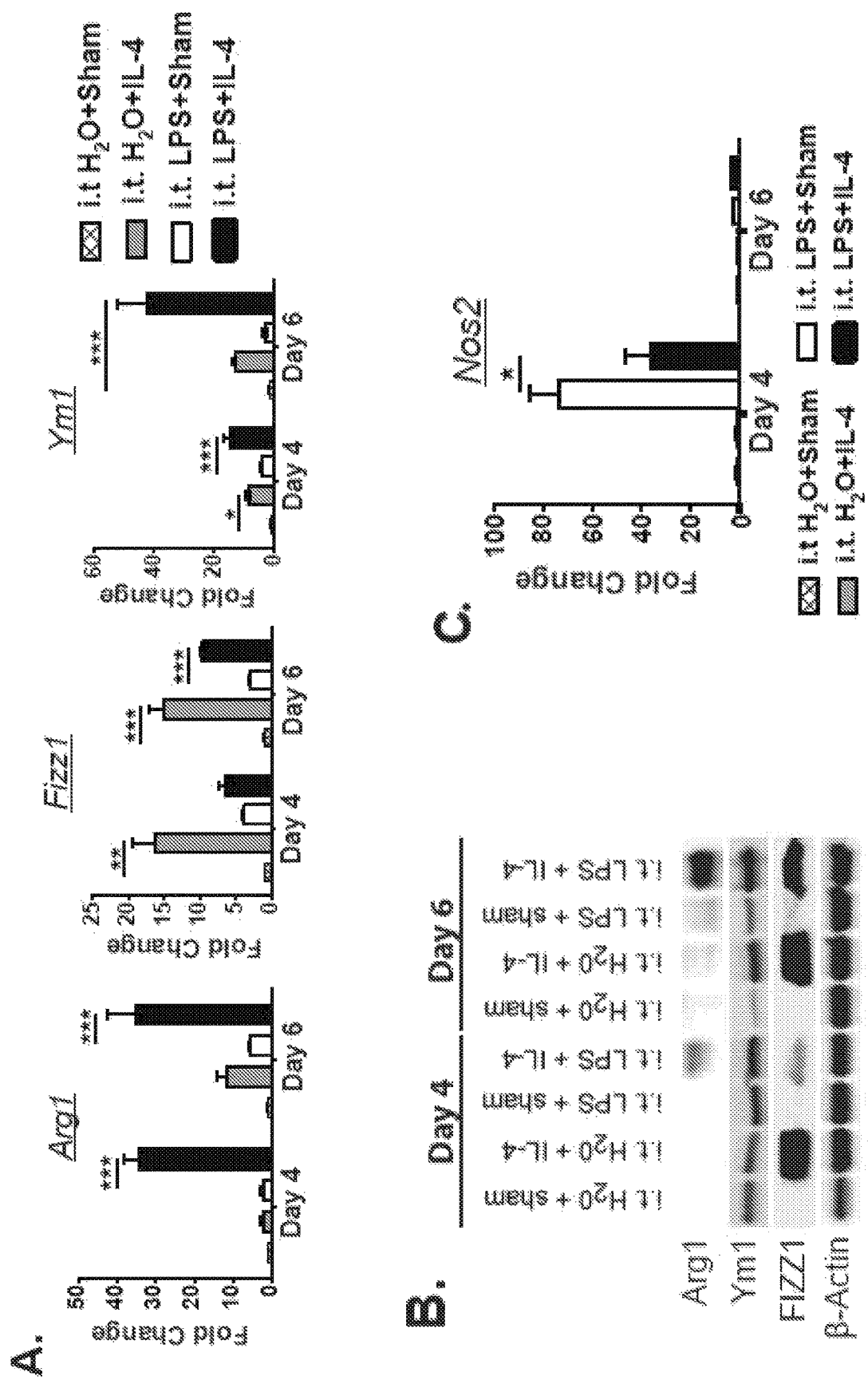
Figure 16:
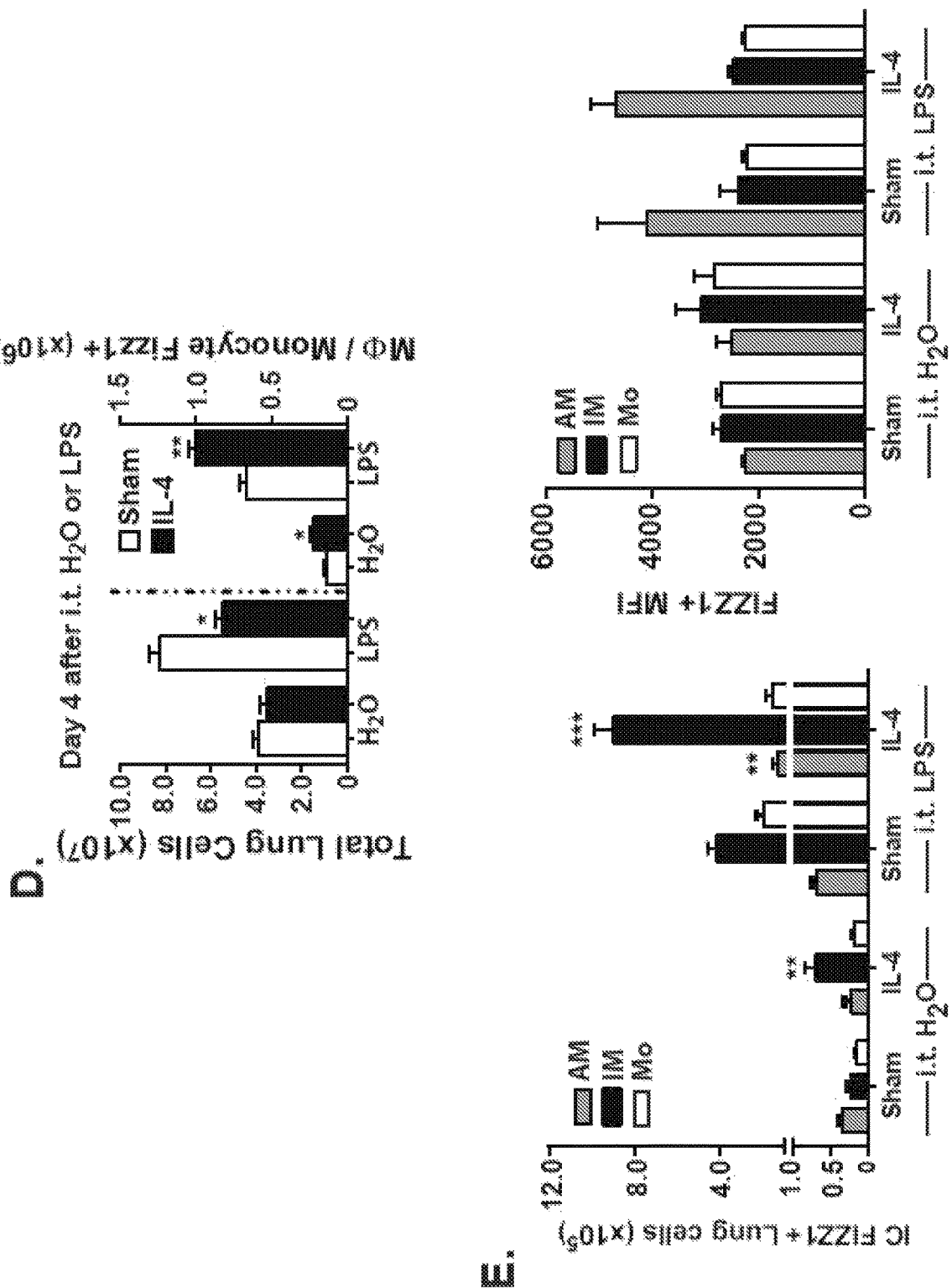
Figure 16:
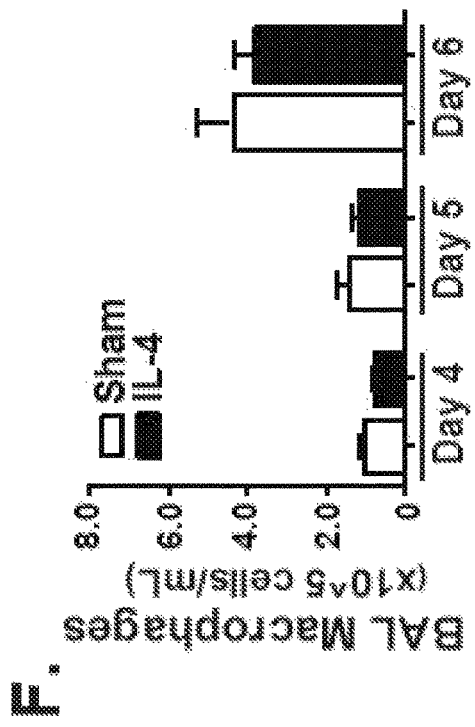
Figure 16:
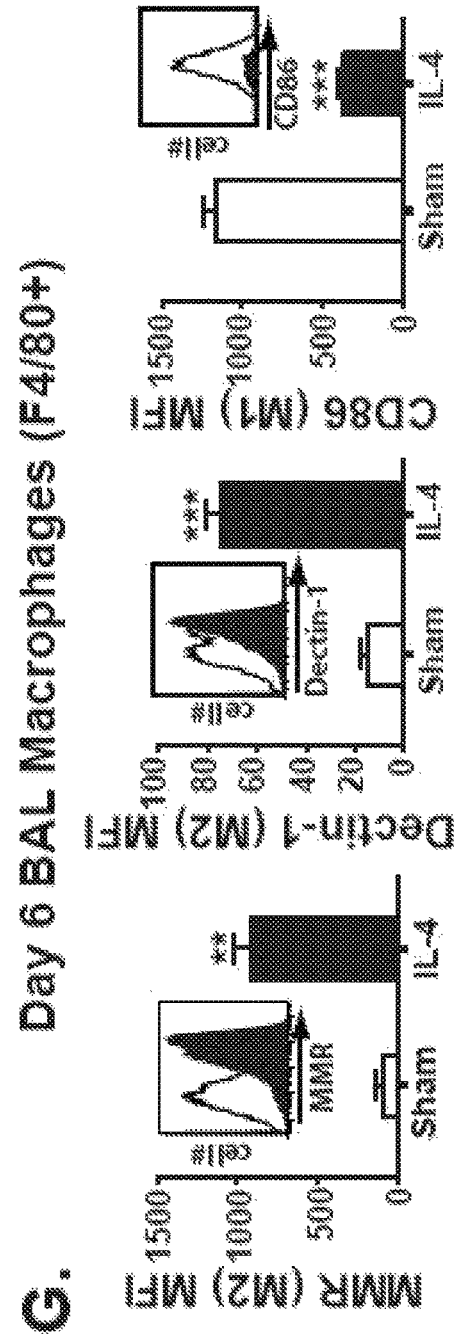

FIGS. 16A to 16G show that lung macrophages prominently expressed M2 proteins following IL-4-treatment in i.t. LPS-exposed WT mice. FIG. 16A shows mRNA expression for the M2 markers Arg1, Fizz1, and Ym1 quantified in the whole lung at days 4 and 6 among i.t. H2O- or LPS-exposed mice with IL-4 or sham treatment (n=3-6, *p<0.05, p<0.01, and *p<0.001 by one-way ANOVA). FIG. 16B shows whole lung tissue immunoblots for Arg1, Ym1, FIZZ1, and β-actin after i.t. LPS or H2O. FIG. 16C shows mRNA expression of the M1 marker Nos2 quantified in the whole lung of mice at days 4 and 6 among the four groups (n=3-6, *p<0.05 by one-way ANOVA). FIG. 16D shows total lung cells (left) and the number of lung monocytes and macrophages that expressed intracellular FIZZ1 using flow cytometry (right) at day 4 after i.t. H2O or i.t. LPS (n=4-5, *p<0.05, and p<0.01 by one-way ANOVA). FIG. 16E shows intracellular FIZZ1 expression quantified by the number of positive cells and MFI for monocyte (Mo, Ly6c+ CD11b+CD64low/−), interstitial macrophage (IM, CD64+ CD11b+F4/80+), and alveolar macrophage (AM, CD64+ SiglecF+CD11b−) populations in the whole lung of each group (n=4-5, p<0.01 and *p<0.001 by t-test comparing H2O or LPS groups for AM, IM, or Mo populations). FIG. 16F shows BAL macrophage numbers in i.t. LPS-exposed mice followed by IL-4 or sham (n=6-10). FIG. 16G shows the M2 markers MMR and Dectin-1, and the M1 marker CD86, quantified on the surface of F4/80+ macrophages at day 6 after i.t. LPS. Representative flow histogram plots of the # of cells (y-axis) and fluorescence intensity (x-axis, log scale) for each marker are shown (n=4-5, p<0.01 and ***p<0.001 by t-test).

Figure 17:
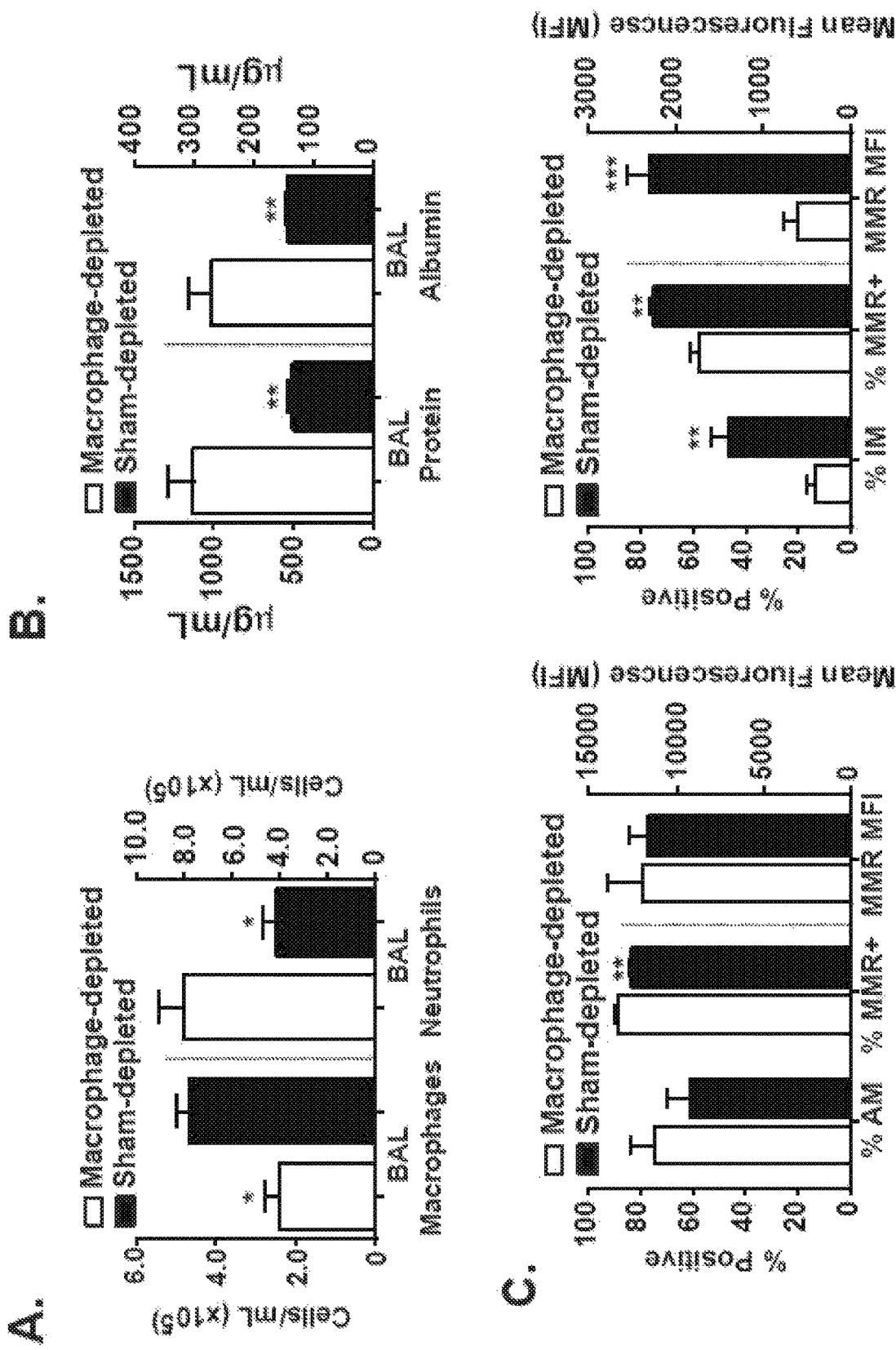

FIGS. 17A to 17C show that macrophage depletion mitigated IL-4 benefits on ALI resolution. FIG. 17A shows BAL macrophage and BAL neutrophil number at day 5 after i.t. LPS and IL-4 in mice receiving either liposomal clodronate (macrophage-depleted) or PBS liposomes (sham-depleted) (n=4-5, *p<0.05 by t-test). FIG. 17B shows BAL protein and BAL albumin at day 5 quantified in both groups following IL-4 therapy (n=4-5, **p<0.01 by t-test). FIG. 17C shows percent depletion of alveolar (AM, F4/80+CD11c+) and interstitial (IM, F4/80+CD11b+) macrophage subpopulations, as well as the % and MFI of MMR expression among these cells (n=4-5, *p<0.05, p<0.01, and *p<0.001 by t-test).

Figure 18:
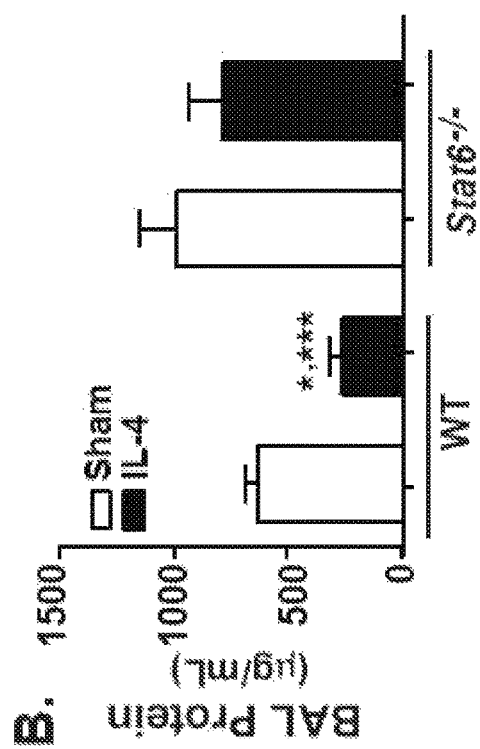
Figure 18:
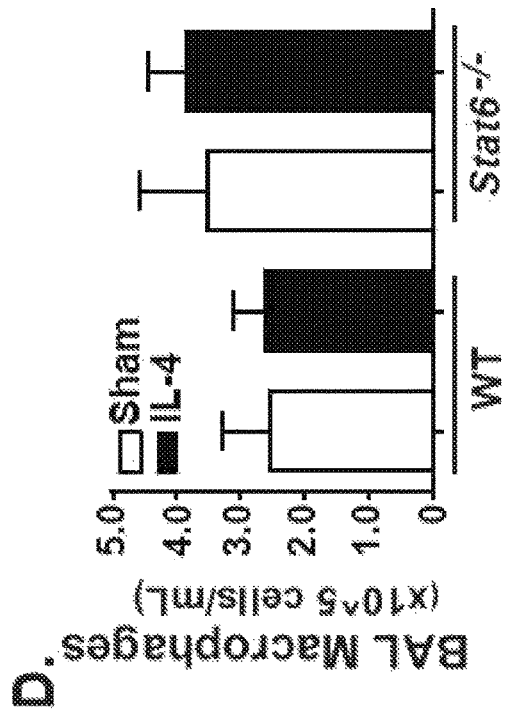
Figure 18:
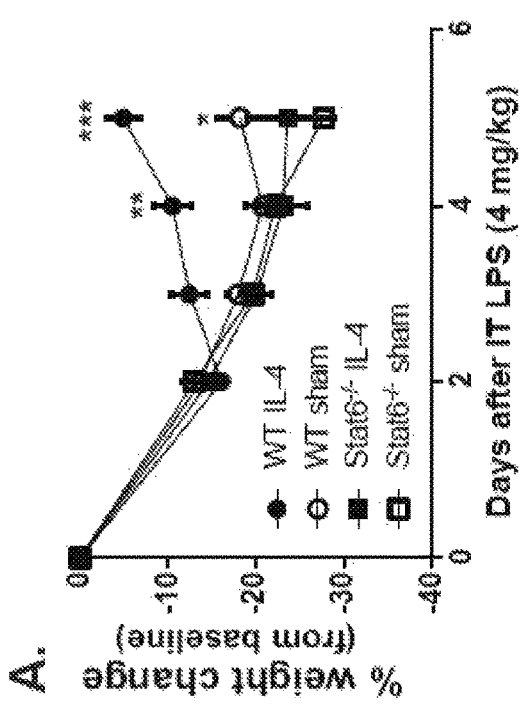
Figure 18:
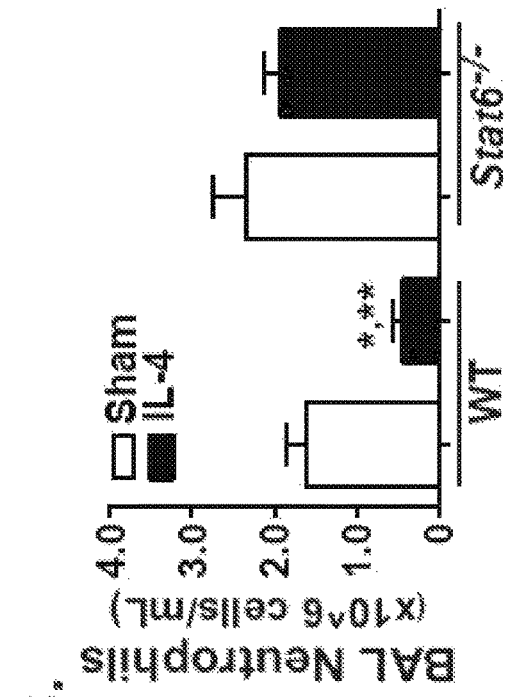
Figure 18:
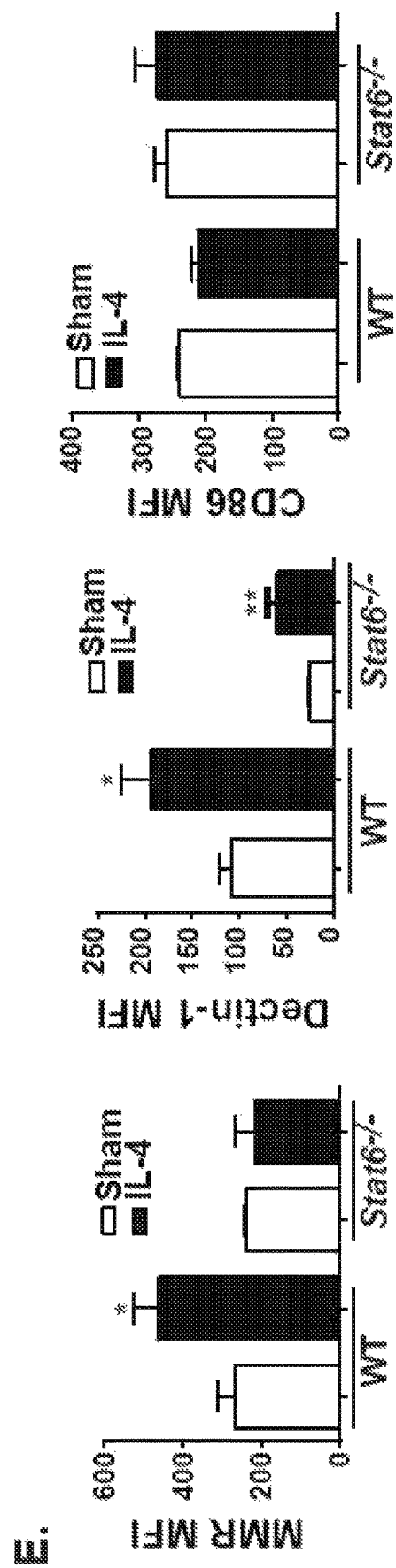

FIGS. 18A to 18E show that IL-4 did not accelerate ALI resolution in Stat6$^{-/-}$ mice. FIG. 18A shows weight change, FIG. 18B shows BAL protein, FIG. 18C shows neutrophils, and FIG. 18D shows macrophages quantified in wild-type (WT) and Stat6$^{-/-}$ mice with IL-4 or sham treatment on day 5 after i.t. LPS (n=7-10. For BAL protein, *p<0.05 compared to WT sham, Stat6$^{-/-}$ IL-4 and ***p<0.001 compared to Stat6$^{-/-}$ sham by t-test. For BAL neutrophils, *p<0.05 to WT sham, and **p<0.01 compared to Stat6$^{-/-}$ by t-test). FIG. 18E shows among BAL macrophages (F4/80+), MFI for mannose receptor (MMR), Dectin-1, and CD86 quantified by flow cytometry (n=4-5, *p<0.05 and **p<0.01 by t-test).

Figure 19:
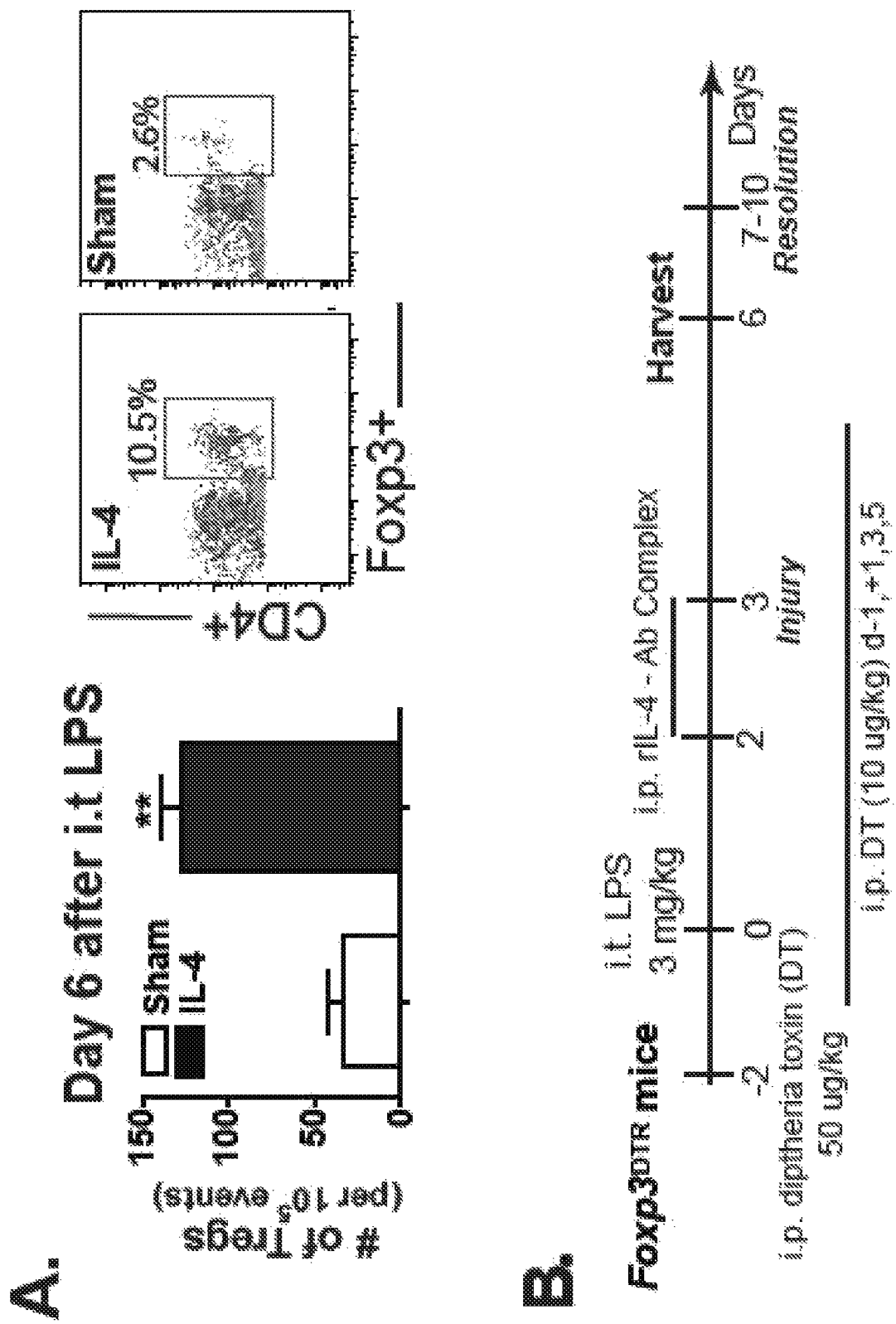
Figure 19:
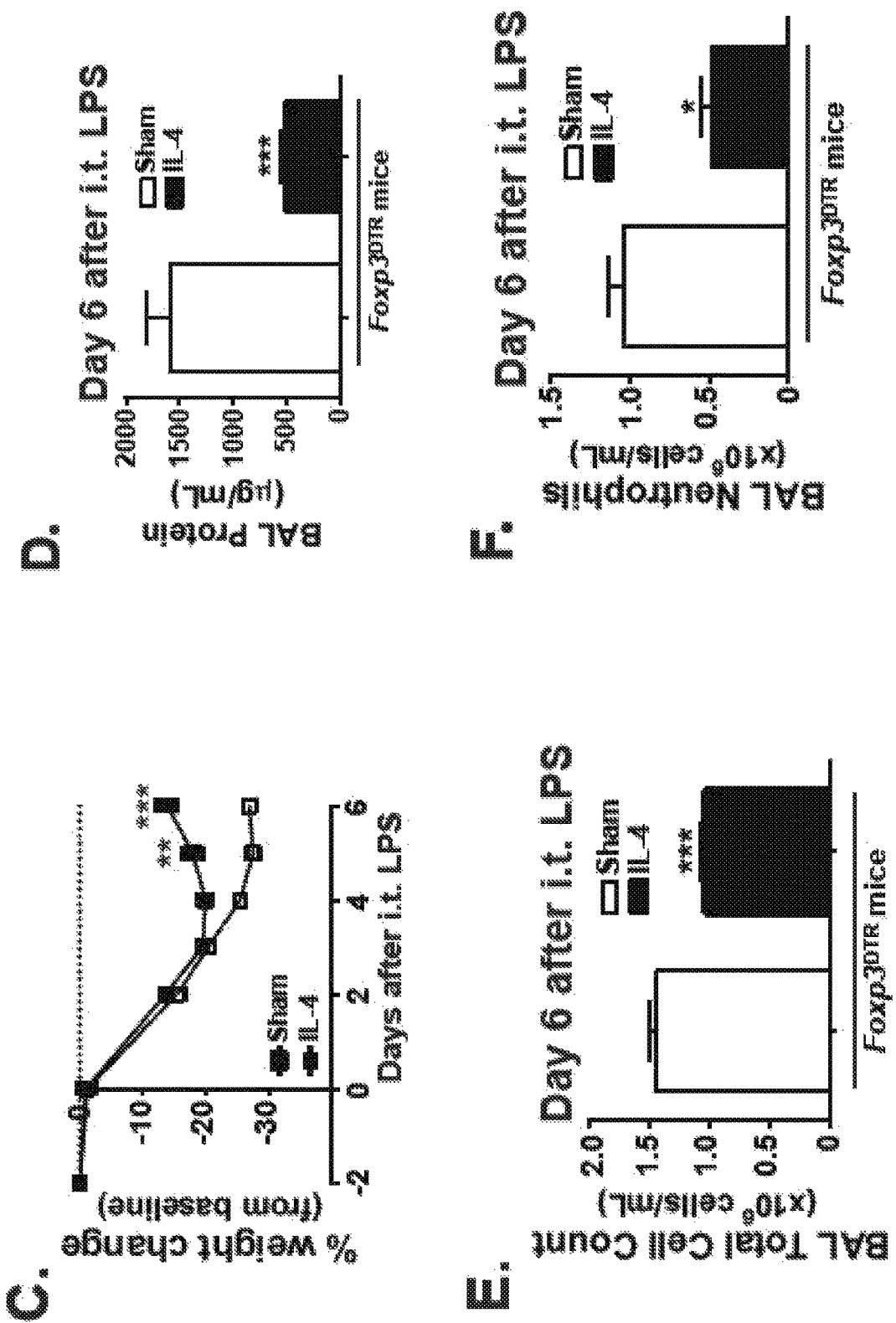
Figure 19:
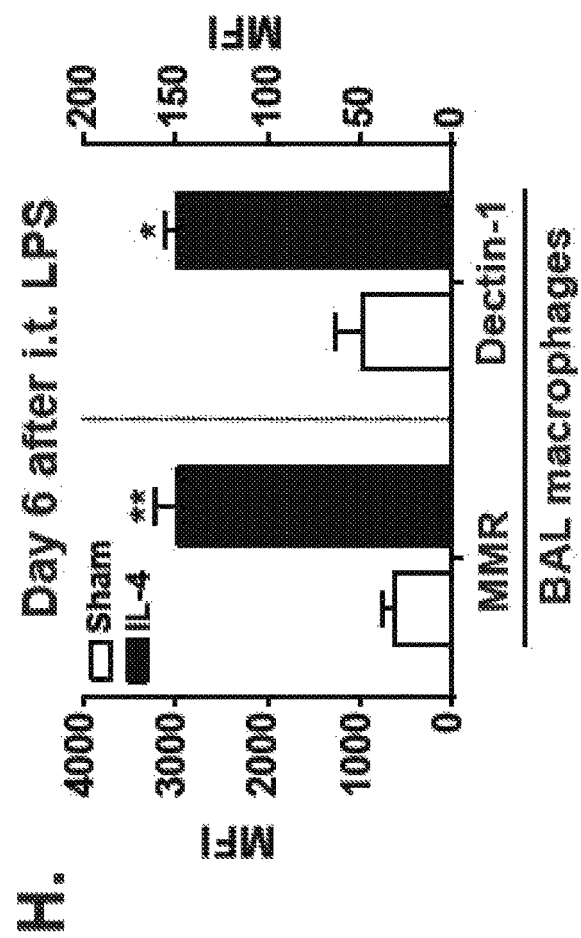
Figure 19:
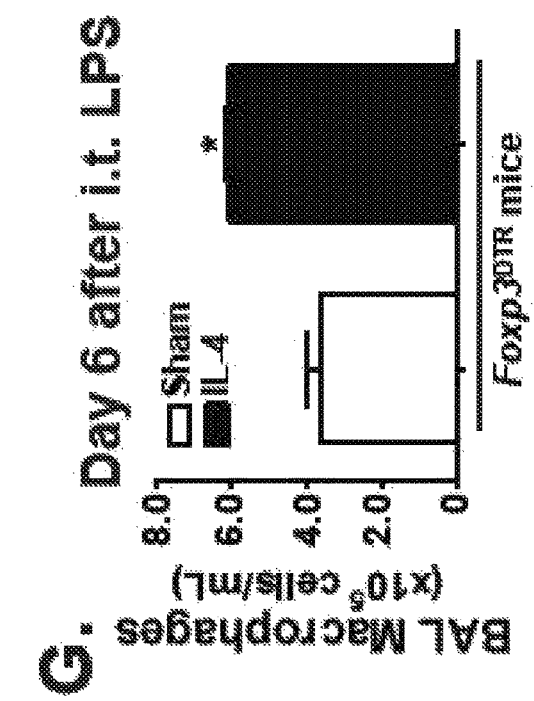

FIGS. 19A to 19H show that regulatory T-cells (Tregs) were not necessary for IL-4 to accelerate ALI resolution. FIG. 19A shows alveolar Tregs enumerated at day 6 following i.t. LPS in sham or IL-4 treated mice (n=4-5, p<0.01 by t-test), following identification by dual positive expression of CD4 and Foxp3 using flow cytometry. FIG. 19B shows the experimental design for Treg depletion in Foxp3DTR mice using i.p. injection of diphtheria toxin (DT). All Foxp3DTR mice received DT to deplete Tregs and either IL-4 or sham treatment following i.t. LPS. FIG. 19C shows daily weight difference compared to baseline (day −2) expressed as percent change (n=7-8, p<0.01, ***p<0.001 by repeated-measures ANOVA). At day 6 after i.t. LPS, ALI markers including: total protein (FIG. 19D), cell count (FIG. 19E), neutrophils (FIG. 19F), and macrophages (FIG. 19G) were quantified following BAL in IL-4 and sham-treated Foxp3DTR mice (n=8, *p<0.05, ***p<0.001 by t-test). FIG. 19H shows among BAL macrophages (F4/80+), the MFI for MMR and Dectin-1 (n=4, *p<0.05, **p<0.01 by t-test).

Figure 20:
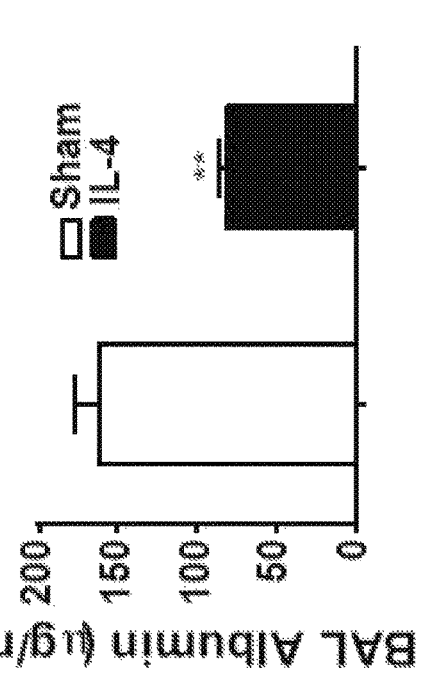
Figure 20:
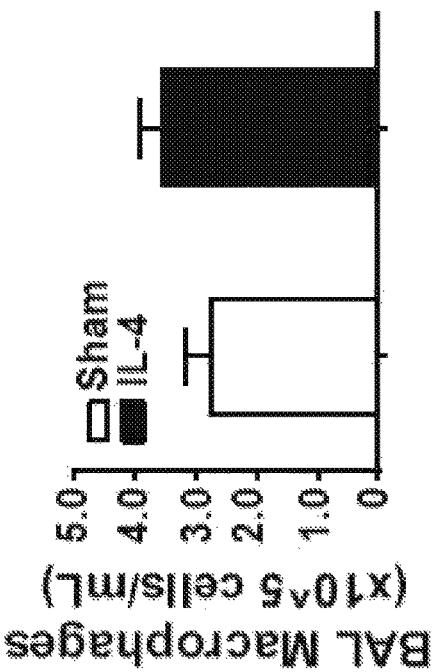
Figure 20:
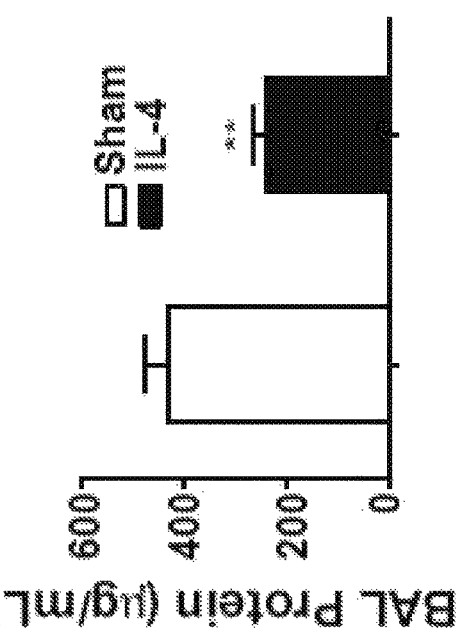
Figure 20:
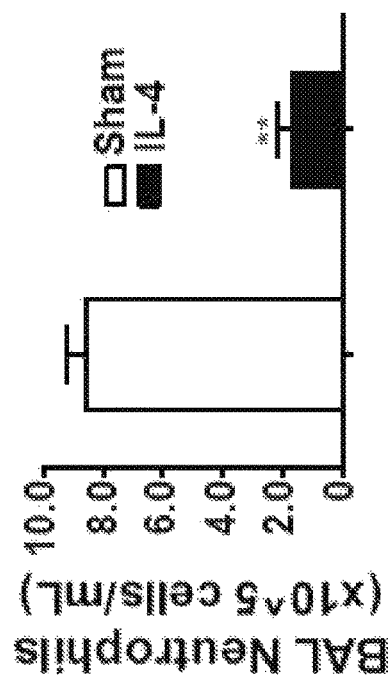
Figure 20:
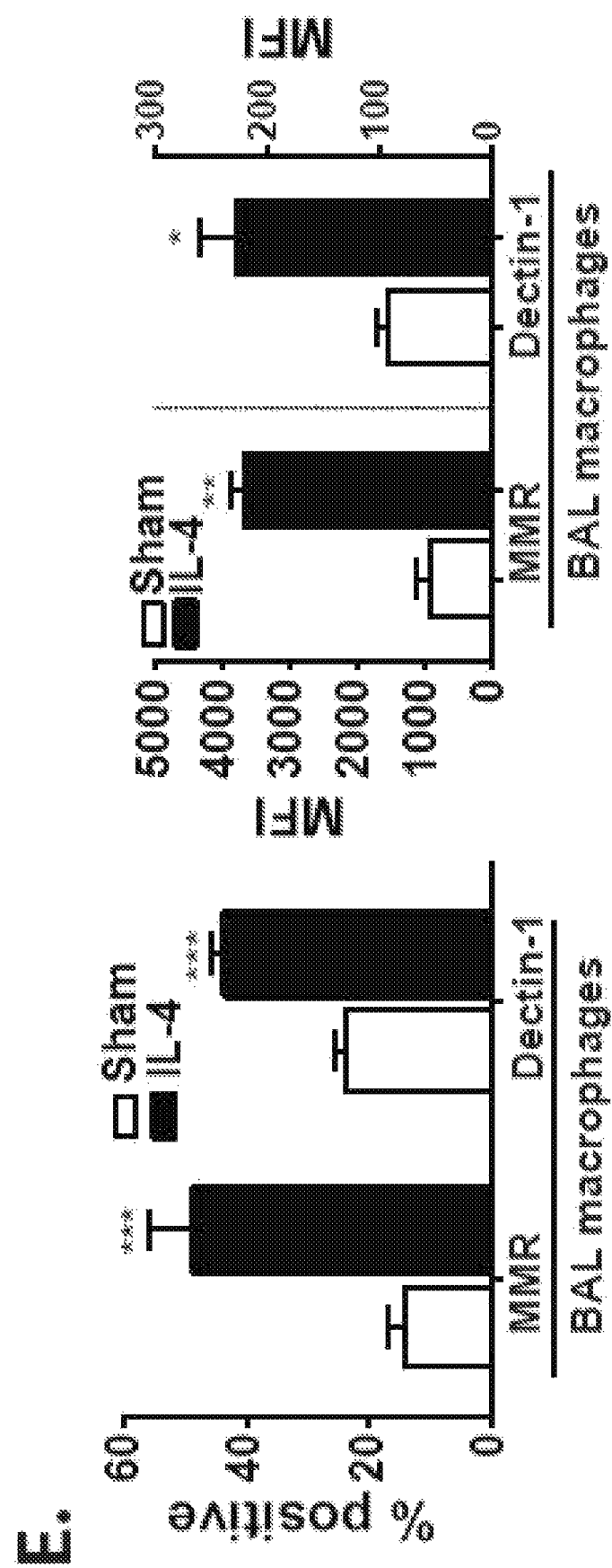

FIG. 20A to 20E show that IL-4 accelerated ALI resolution following lung *Pseudomonas* challenge. BAL protein (FIG. 20A), BAL albumin (FIG. 20B), BAL neutrophils (FIG. 20C), and BAL macrophages (FIG. 20D) were quantified (n=6, **p<0.01 by t-test.) at day 4 in wild-type mice exposed to i.t. PAO1 (2×10$^6$ CFUs) followed by IL-4 or sham on days 2 and 3. FIG. 20E shows among BAL macrophages (F4/80+), the % positive and MFI for the M2 markers MMR and Dectin-1 (n=6, *p<0.05, p<0.01, *p<0.001 by t-test).

DETAILED DESCRIPTION

The present invention relates, at least in part, to the unexpected observation that administration of a DNA methyltransferase inhibitor or an IL-4 agent to a mammalian subject having an acute lung injury promoted recovery of the subject from the acute lung injury. Administration of a DNA methyltransferase inhibitor activated and/or expanded the active population/raised the frequency of regulatory T cells in a mammalian subject having an acute lung injury, exerting a positive therapeutic outcome on recovery of the subject from the acute lung injury. Treg DNMT inhibition augmented Treg suppressive phenotype and function in the subject and accelerated resolution of LPS-induced lung injury. Ev vivo administration of a DNA methyltransferase inhibitor to a cell population comprising T cells was also identified as therapeutically effective—specifically, using adoptive transfer experiments, it was also established that the Treg subpopulation was the active lymphocyte fraction involved in promoting repair.

It was specifically established that Foxp3+ regulatory T cell DNA methyltransferase inhibition was an epigenetic mechanism that accelerated resolution of acute lung injury. The salutary effect of DNMT inhibition required Tregs, and adoptive transfer experiments confirmed that Tregs mediated the inhibitor's pro-resolution action. Without wishing to be bound by theory, while systemic DNMT inhibition likely acted upon multiple cell types involved in lung injury repair, Tregs were identified as exquisitely depending on DNA demethylation (10) and therefore Tregs might have also been more predisposed to the effects of a DNMT inhibitor. Previous reports described how histone deacetylase inhibition can avert or mitigate lung injury (33-35), perhaps via MAP kinase pathway modulation.

Acute respiratory distress syndrome (ARDS) is a devastating inflammatory lung disease for which there are no effective targeted therapies. In experimental models of acute lung inflammation and injury, regulatory T cells (Tregs) orchestrated a pro-repair program. Meanwhile, Tregs themselves were highly dependent on epigenetic mechanisms, such as DNA hypomethylation.

Epigenetic manipulation to promote resolution of ongoing inflammation has heretofore not been described in the literature, and DNA methylation has not been previously characterized as a mechanism in acute lung injury resolution.

Macrophages are critical for initiation of lung inflammation, but also for resolution and repair of the lung Immunotherapy with IL-4 reprogrammed macrophages into an anti-inflammatory and pro-repair phenotype. In an experimental lung injury model, it was determined that systemic delivery of recombinant IL-4 (rIL-4) initiated 2 days after onset of severe lung inflammation and damage dramatically accelerated resolution of lung inflammation and repair.

The model and findings presented herein have translational relevance to patients with ARDS or those patients at significant risk for ARDS. In particular, the ability to deliver systemic immunotherapy well after onset of lung inflammation is quite appealing for a severe condition in which patients rarely seek medical care prior to the development of lung inflammation. Because ARDS is an acute inflammatory process with a mortality in the range of 30-40%, any potential immunotherapy is promising. As has been shown herein, exogenous, systemic delivery of recombinant IL-4 (rIL-4) was clearly a beneficial therapy in experimental models of lung injury, promoting resolution of acute inflammatory conditions. Sterile direct lung injury using LPS, a Gram-negative bacterial cell wall component, is an established model to study lung inflammation and recapitulated many ARDS features, including neutrophilic alveolitis, modest mortality, and spontaneous resolution in survivors. The sterile inflammation model used herein is relevant to many causes of ARDS, including aspiration of gastric contents, ventilator-induced lung injury, near drowning, and collateral lung injury associated with treated infection. Additionally, it has been initially identified herein that rIL-4 can positively impact lung injury resolution following bacterial and viral pneumonia in experimental models.

In humans, rIL-4 has been shown to be safe and potentially effective in treating immune-mediated diseases such as psoriasis, but has never been used to treated acute inflammation as occurs in ARDS. The present invention is based, at least in part, upon identification of rIL-4 as an appropriate immunotherapy for patients with ARDS, establishing a basis for clinical testing of this agent as a therapeutic.

Definitions

The term "DNA methyltransferase inhibitor" or "DNMTi" has its general meaning in the art and refers to a lung injury treatment, e.g., systemic or ex vivo. Exemplary "DNA methyltransferase inhibitors" can be sub-divided into nucleoside analogues (e.g., 5-Azacytidine (azacytidine), 5-Aza-2'-deoxycytidine (decitabine, 5-Aza-Cd; referred to as "DAC" herein), zebularine, 5-Fluoro-2'-deoxycytidine (5-F-CdR), 5,6-Dihydro-5-azacytidine (DHAC)) and non-nucleoside analogue families (e.g., Hydralazine, Procainamide, Procaine, EGCG ((−)-epigallocatechin-3-gallate), Psammaplin A, MG98, RG108, and other inhibitors of DNA methyltransferase including, e.g., antisense and RNAi agents).

Regulatory T cells are also referred to as Treg and were formerly known as suppressor T cell. Regulatory T cells are a component of the immune system that suppress immune responses of other cells. Regulatory T cells usually express CD3, CD4, CD8, CD25, and Foxp3. Additional regulatory T cell populations include Th1, Th3, CD8+CD28−, CD69+, and Qa-1 restricted T cells. Regulatory T cells actively suppress activation of the immune system and prevent pathological self-reactivity, i.e. autoimmune disease. The immunosuppressive cytokines TGF-beta and Interleukin 10 (IL-10) have also been implicated in regulatory T cell function. Similar to other T cells, a subset of regulatory T cells can develop in the thymus and this subset is usually referred to as natural Treg (or nTreg). Another type of regulatory T cell (induced Treg or iTreg) can develop in the periphery from naïve CD4+ T cells. The large majority of Foxp3-expressing regulatory T cells are found within the major histocompatibility complex (MHC) class II restricted CD4-expressing (CD4+) helper T cell population and express high levels of the interleukin-2 receptor alpha chain (CD25). In addition to the Foxp3-expressing CD4+ CD25+, there also appears to be a minor population of MHC class I restricted CD8+ Foxp3-expressing regulatory T cells. Unlike conventional T cells, regulatory T cells do not produce IL-2 and are therefore anergic at baseline. An alternative way of identifying regulatory T cells is to determine the DNA methylation pattern of a portion of the foxp3 gene (TSDR, Treg-specific-demethylated region) which is found demethylated in Tregs.

As used herein, the term "inflammatory disease" or "inflammatory disorder" refers to pathological states resulting in inflammation, typically caused by leukocyte infiltration. Examples of such disorders include inflammatory skin diseases, including, without limitation, psoriasis and atopic dermatitis; systemic scleroderma and sclerosis; responses associated with inflammatory bowel disease (IBD) (such as Crohn's disease and ulcerative colitis); ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma, hypovolemic shock; asphyxia; acute respiratory distress syndrome; acute-lung injury; Behcet's Disease; dermatomyositis; polymyositis; multiple sclerosis (MS); dermatitis; meningitis; encephalitis; uveitis; osteoarthritis; lupus nephritis; autoimmune diseases such as rheumatoid arthritis (RA), Sjorgen's syndrome, vasculitis; diseases involving leukocyte diapedesis; central nervous system (CNS) inflammatory disorder, multiple organ injury syndrome secondary to septicaemia or trauma; alcoholic hepatitis; bacterial pneumonia; antigen-antibody complex mediated diseases including glomerulonephritis; sepsis; sarcoidosis; immunopathologic responses to tissue or organ transplantation; inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis; etc.

Exemplary "acute inflammatory diseases or disorders" include, but are not limited to, acute lung injury, acute liver failure, systemic inflammatory response syndrome (SIRS), different degrees of sepsis including sepsis, severe sepsis, and septic shock, etc.

The term "effective amount" includes an amount effective, at dosages and for periods of time necessary, to achieve the desired result, e.g., sufficient to treat lung injuries. An effective amount of a DNA methyltransferase inhibitor may vary according to factors such as the disease/injury state, age, and weight of the subject, and the ability of the DNA methyltransferase inhibitor to elicit a desired response in the subject. An effective amount of an IL-4 agent (e.g., IL-4, optionally a recombinant IL-4 or fragment thereof, or an IL-4 agonist (e.g., an activator of IL-4, an antibody, compound or other agent that activates IL-4Rα, etc.)) may vary according to factors such as the disease/injury state, age, and weight of the subject, and the ability of the IL-4 agent to elicit a desired response in the subject. Dosage regimens may be adjusted to provide the optimum therapeutic response. An effective amount is also one in which any toxic or detrimental effects (e.g., side effects) of an IL-4 agent or a DNA methyltransferase inhibitor are outweighed by the therapeutically beneficial effects.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between any two of these values. Such improvement or change may be observed in treated subjects as compared to subjects not treated with an IL-4 agent or a DNA methyltransferase inhibitor, where the untreated subjects have, or are subject to developing, the same or similar injury/condition, disease, symptom or the like. Amelioration of an injury/condition, disease, symptom or assay parameter may be determined subjectively or objectively, e.g., via self-assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s), by detection of respiratory or inflammatory disorders in a subject, and/or by modalities such as, but not limited to photographs, video, digital imaging and pulmonary function tests. Amelioration may be transient, prolonged or permanent, or it may be variable at relevant times during or after an IL-4 agent or a DNA methyltransferase inhibitor is administered to a subject or is used in an assay or other method described herein or a cited reference, e.g., within timeframes described infra, or about 12 hours to 24 or 48 hours after the administration or use of an IL-4 agent or a DNA methyltransferase inhibitor to about 3, 4, 5, 6, 7, 8, 9, 10, 11, 12, 13, 14, 21, 28 days, or 1, 3, 6, 9 months or more after a subject(s) has received such treatment.

The "modulation" of, e.g., a symptom, level or biological activity of a molecule, or the like, refers, for example, to the symptom or activity, or the like that is detectably increased or decreased. Such increase or decrease may be observed in treated subjects as compared to subjects not treated with an IL-4 agent or a DNA methyltransferase inhibitor, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self-assessment, by a clinician's assessment or by conducting an appropriate assay or measurement, including, e.g., quality of life assessments, suitable assays for the level or activity of molecules, cells or cell migration within a subject and/or by modalities such as, but not limited to photographs, video, digital imaging and pulmonary function tests. Modulation may be transient, prolonged or permanent or it may be variable at relevant times during or after an IL-4 agent or a DNA methyltransferase inhibitor is administered to a subject or is used in an assay or other method described herein or a cited reference, e.g., within times described infra, or about 12 hours to 24 or 48 hours after the administration or use of an IL-4 agent or a DNA methyltransferase inhibitor to about 3, 4, 5, 6, 7, 8, 9, 10, 11, 12, 13, 14, 21, 28 days, or 1, 3, 6, 9 months or more after a subject(s) has received such treatment.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

As used herein, the term "polypeptide", and the terms "protein" and "peptide" which are used interchangeably herein, refers to a polymer of amino acids. Exemplary polypeptides include gene products, naturally-occurring proteins, homologs, orthologs, paralogs, fragments, and other equivalents, variants and analogs of the foregoing.

As used herein, the term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, and multiplying the result by 100 to yield the percentage of sequence identity. Methods to calculate sequence identity are known to those of skill in the art and described in further detail below.

As used herein, the terms "stringent conditions" or "stringent hybridization conditions" refer to conditions which promote specific hybridization between two complementary polynucleotide strands so as to form a duplex. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of the a polynucleotide sequence hybridizes to a perfectly matched complementary strand. In certain cases it may be desirable to increase the stringency of the hybridization conditions to be about equal to the Tm for a particular duplex. In certain cases, stringent hybridization conditions include a wash step of 0.2×SSC at 65° C.

As used herein, "subject" includes organisms which are capable of suffering from a lung injury, disease and/or disorder treatable by an IL-4 agent or a DNA methyltransferase inhibitor (via direct administration of the IL-4 agent or DNA methyltransferase inhibitor to the subject or via treatment of cells with the IL-4 agent or DNA methyltransferase inhibitor, with such cells administered to the subject) or who could otherwise benefit from the administration of an IL-4 agent or a DNA methyltransferase inhibitor as described herein, such as human and non-human animals. Preferred human animals include human subjects. The term "non-human animals" includes all vertebrates, e.g., mammals, e.g., rodents, e.g., mice, and non-mammals, such as non-human primates, e.g., sheep, dog, cow, chickens, amphibians, reptiles, etc.

The term "carrier" refers to a diluent, excipient, and/or vehicle with which an active compound is administered. The pharmaceutical compositions of the invention may contain combinations of more than one carrier. Such pharmaceutical carriers are well known in the art. The pharmaceutical compositions may also comprise any suitable binder(s), lubricant(s), suspending agent(s), coating agent(s), and/or solubilizing agent(s) and so on. The compositions can also contain other active components, e.g. other drugs for the treatment of lung injury or other diseases and/or conditions that are co-treated.

A cell is considered "allogeneic" with respect to another cell if both cells are derived from the same animal species but presents sequence variation in at least one genetic locus. A cell is considered "allogeneic" with respect to a subject if the cell is derived from the same animal species as the subject but presents sequence variation in at least one genetic locus when compared to the subject's respective genetic locus.

A cell is considered "autologous" with respect to another cell if both cells are derived from the same individual or from genetically identical twins. A cell is considered "autologous" to a subject, if the cell is derived from the subject or a genetically identical twin. Autologous cells do not induce an immune reaction (such as a rejection) when they are introduced into an immuno-competent host. A "suitable dosage level" refers to a dosage level that provides a therapeutically reasonable balance between pharmacological effectiveness and deleterious effects. Often this dosage level is related to the peak or average serum levels resulting from administration of a drug at the particular dosage level.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

Any compositions or methods provided herein can be combined with one or more of any of the other compositions and methods provided herein.

In certain embodiments, the present invention provides isolated nucleic acid and/or polypeptide molecules having a nucleotide or polypeptide sequence at least 80% identical, at least 85% identical, at least 90% identical, at least 95% identical, or at least 96%, 97%, 98% or 99% identical to a polynucleotide or polypeptide comprising, consisting of, or consisting essentially of the polynucleotide or amino acid sequence of an IL-4 polynucleotide or polypeptide sequence as set forth herein, or fragments thereof.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

Polynucleotide variants can contain alterations in the coding regions, non-coding regions, or both. In some embodiments, the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

The terms "identical" or "percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software are known in the art that may be used to obtain alignments of amino acid or nucleotide sequences. One such non-limiting example of a sequence alignment algorithm is the algorithm described in Karlin et al., *Proc. Natl. Acad. Sci.*, 87:2264-2268 (1990), as modified in Karlin et al., *Proc. Natl. Acad. Sci.*, 90:5873-5877 (1993), and incorporated into the NBLAST and XBLAST programs (Altschul et al., *Nucleic Acids Res.*, 25:3389-3402 (1991)). In certain embodiments, Gapped BLAST may be used as described in Altschul et al., *Nucleic Acids Res.* 25:3389-3402 (1997). BLAST-2, WU-BLAST-2 (Altschul et al., *Methods in Enzymology*, 266:460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgap-dna.CMP matrix and a gap weight of 40, 50, 60, 70, or 90 and a length weight of 1, 2, 3, 4, 5, or 6). In certain embodiments, the GAP program in the GCG software package, which incorporates the algorithm of Needleman and Wunsch (*J. Mol. Biol.* (48):444-453 (1970)) may be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). In certain embodiments, the percent identity between nucleotide or amino acid sequences is determined using the algorithm of Myers and Miller (CABIOS, 4:11-17 (1989)). For example, the percent identity may be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 5, at least about 10, about 20, about 40-60 residues in length or any integral value therebetween, or over a longer region than 60-80 residues, at least about 90-100 residues, or the sequences are substantially identical over the full length of the sequences being compared.

A "conservative amino acid substitution" is one in which one amino acid residue is replaced with another amino acid residue having a similar side chain Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s). Methods of identifying nucleotide and amino acid conservative substitutions which do not eliminate antigen binding are well-known in the art (see, e.g., Brummell et al., *Biochem.* 32: 1180-1 187 (1993); Kobayashi et al. *Protein Eng.* 12(10):879-884 (1999); and Burks et al. *Proc. Natl. Acad. Sci. USA* 94:.412-417 (1997)).

The polypeptides of the present invention can be recombinant polypeptides, natural polypeptides, or synthetic polypeptides. It will be recognized in the art that some amino acid sequences of the invention can be varied without significant effect of the structure or function of the protein. Such mutants include deletions, insertions, inversions, repeats, and type substitutions.

The polypeptides and analogs can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in Remington's Pharmaceutical Sciences, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest (IL-4). Optionally, the sequence can be mutagenized by site-specific mutagenesis to provide functional analogs thereof. See, e.g. Zoeller et al., *Proc. Nat'l. Acad. Sci.* USA 81:5662-5066 (1984) and U.S. Pat. No. 4,588,585.

DNMT Inhibitor ARDS Therapeutic Approach

No previously known targeted therapies had been identified as promoting resolution of acute lung inflammation, as occurs in the acute respiratory distress syndrome (ARDS). It was unexpectedly determined that the DNA methyltransferase inhibitor 5-aza-2'-deoxycytidine accelerated resolution of experimental lung injury, at least in part via a salutary effect on Treg phenotype and function. Epigenetic manipulation of the regulatory T cell lineage represented a therapeutic strategy for the acute respiratory distress syndrome, which also appeared to be applicable to other acute inflammatory disorders.

Acute respiratory distress syndrome (ARDS) is a common and oftentimes fatal inflammatory lung condition without effective targeted therapies. Regulatory T cells (Tregs) resolve lung inflammation, but mechanisms that enhance Tregs to promote resolution of established damage remain unknown. DNA demethylation at the forkhead box protein 3 (Foxp3) locus and other key Treg loci typify the Treg lineage. To test how dynamic DNA demethylation affected lung injury resolution, the DNA methyltransferase inhibitor 5-aza-2'-deoxycytidine (DAC) was administered to wild type mice, beginning 24 hours after intratracheal lipopolysaccharide-induced lung injury. Mice that received DAC exhibited accelerated resolution of their injury. Lung CD4+ CD25$^{hi}$Foxp3+ Tregs from DAC-treated wild type mice increased in number and displayed enhanced Foxp3 expression, activation state, suppressive phenotype, and proliferative capacity. Lymphocyte-deficient recombinase activating gene-1-null (Rag-1$^{-/-}$) mice and Treg-depleted (diphtheria toxin-treated Foxp3DTR) mice did not resolve their injury in response to DAC. Adoptive transfer of 2×10$^5$ DAC-treated, but not vehicle-treated, exogenous Tregs rescued Treg-deficient mice from ongoing lung inflammation. Additionally, in wild type mice having influenza-induced lung inflammation, DAC rescue treatment facilitated recovery of their injury and promoted an increase in lung Treg number. Thus, DNA methyltransferase inhibition, at least in part, augmented Treg number and functioned to accelerate repair of experimental lung injury. Epigenetic pathways were therefore identified as novel manipulable targets for the treatment of ARDS.

Acute respiratory distress syndrome (ARDS), an inflammatory condition caused by direct or indirect lung injury, is a common and life-threatening disease (1). Despite extensive investigation into initial events that cause ARDS pathology, no targeted therapies have been previously identified to promote repair in the damaged lung. Resolution of inflammation following acute lung injury has been identified to be an active process (2) that required CD4+CD25+Foxp3+ regulatory T cells (Tregs) in a direct lung injury mouse model: intratracheal lipopolysaccharide (LPS) administration (3). In that model, surviving wild type mice spontaneously resolved their injury 7-10 days after receiving LPS. Lymphocytes did not determine initial injury severity; however, injury resolution required lymphocytes, as evidenced by unremitting LPS-induced lung inflammation in lymphocyte-deficient recombinase activating gene-1-null (Rag-1$^{-/-}$) mice. Using adoptive transfer experiments, the Treg subpopulation was identified as the active lymphocyte fraction involved in promoting resolution via pro-repair effects on macrophage inflammatory function, neutrophil efferocytosis, epithelial proliferation (4), and limitation of fibroproliferation (5). Tregs have also been characterized as promoting repair in other tissue damage models, as well as in clinical scenarios (6,7). While Treg cell transfer may be a viable management strategy for chronic conditions (7), the briskly evolving nature of ARDS makes a cell transfer-based therapy impractical.

Tregs comprise a CD4+ lymphocyte subset that attenuates both innate and adaptive immune responses (9). Treg development and function require epigenetic programming—prominently through DNA demethylation—and forkhead box protein 3 (Foxp3) transcription factor expression (10, 11). Constitutive Foxp3 expression was identified as necessary for Treg suppressive activity (12,13), and epigenetic marks were characterized as regulating transcription at the Foxp3 locus and the loci of other key Treg genes (10,14). In mice and humans, distinct regions within Treg gene loci (including Foxp3) were identified to display cytosine-phospho-guanine (CpG) methylation patterns that differed between Tregs and CD4+CD25− conventional T cells with hypomethylation dominating in Tregs (10,15-19). Importantly, Foxp3 expression correlated with Treg suppressive function (11,20,21). Epigenetic mechanisms could represent potential targets to rapidly expand Treg numbers and enhance their function (8).

DNA methyltransferases (DNMTs) control de novo and maintenance CpG methylation during cell division and development (22). CpG methylation within promoters and transcription factor binding sites represses gene transcription, and DNMT inhibition or knockdown can lead to DNA demethylation. DNMTs determine Foxp3 expression and Treg identity, as DNMT silencing or inhibition via siRNA or 5-aza-2'-deoxycytidine (DAC) have respectively been identified to lead to Foxp3 expression and Treg phenotype in naïve CD4+ non-Treg cells (17, 23-25).

DNA demethylation was therefore identified to be important to Treg biology, and it was newly hypothesized that pharmacologic DNMT inhibition might lead to enhanced repair following lung injury via a beneficial effect on Tregs. The results described herein demonstrated that Treg DNMT inhibition augmented Treg suppressive phenotype and function and accelerated resolution of direct lung injury. Certain results have been presented as abstracts (26,27).

Summary of DNA Methyltransferase Inhibition Results

As described herein, Foxp3+ regulatory T cell DNA methyltransferase inhibition was established as an epigenetic mechanism that accelerates resolution of acute lung injury. The salutary effect of DNMT inhibition required Tregs, and the adoptive transfer experiments described above confirmed that Tregs, at least in part, mediated the inhibitor's pro-resolution action. While systemic DNMT inhibition likely acts on multiple cell types involved in lung injury repair, Tregs exquisitely depend on DNA demethylation and therefore may be predisposed to the effects of a DNMT inhibitor.

ARDS is a devastating disease for which there is a lack of targeted therapy despite extensive insight into the initial inflammatory injury. Events determining resolution of lung inflammation were a main focus of the studies performed herein. Resolution of injury required not only cessation of ongoing pathology but also active repair of damaged tissues (2). In contrast to reports employing pre-treatment with a histone deacetylase inhibitor (33-35), as described herein, resolution was identified to be accelerated by a DNMT inhibitor administered after lung injury establishment. DNMT inhibition did not modify early LPS-injury as described herein, highlighting that dynamic changes in DNA methylation patterns that likely occur during resolution.

The findings and model described herein have translational relevance to ARDS. While systemic administration of a DNMT inhibitor represents one therapeutic strategy, ex vivo treatment of Tregs with a DNMT inhibitor followed by cell transfer are expected to improve the drug's therapeutic index. Adoptive transfer of Tregs that have been expanded or modified ex vivo is a validated experimental therapy to promote resolution of acute and chronic inflammatory conditions (7). Diseases with a predictable time course, such as graft-versus-host disease, are predicted to be ideal disorders for Treg-based clinical immunotherapy (38-40). However, the timescale required to generate a therapeutic Treg dose is on the order of weeks (41,42), which currently seems too long for a practical ARDS treatment. Epigenetic modification using DNMT inhibition to rapidly augment Treg number and function either in or ex vivo holds translational therapeutic potential for acute inflammatory diseases, including ARDS. The model described herein—sterile direct lung injury using the Gram-negative bacterial cell wall component LPS—is a well-characterized system for study of lung inflammation (43) and recapitulates many ARDS features including neutrophilic alveolitis, modest mortality, and spontaneous resolution in survivors (3). The sterile inflammatory model described herein has relevance for many ARDS causes including aspiration of gastric contents, ventilator-induced lung injury, near drowning, and collateral lung injury associated with treated bacterial infection. Moreover, the data described herein, obtained using an influenza model, broadens the applicability of epigenetic manipulation as a therapeutic strategy for ARDS.

Diphtheria toxin-treated WT mice were selected as controls for the experiments described herein using Foxp3DTR mice, which expressed a normal Foxp3 protein and a diphtheria toxin receptor-green fluorescent protein fusion product (DTR-GFP). While mice expressing a Foxp3-GFP fusion protein (Foxp3gfp) have facilitated studies of Treg biology (44), these mice exhibited abnormal Treg epigenetic programming due to the altered Foxp3 protein (45). Thus, mice with a normal Foxp3 protein were selected to ensure fidelity of epigenetic responses.

Despite their rarity, Tregs coordinate resolution of direct lung injury via cellular interactions that lead to pro-repair effects on alveolar macrophage responses (3), epithelial regeneration (4), and limitation of fibrocyte-mediated fibrosis (5). However, the specific Treg subset involved in injury resolution has remained undefined. Ex vivo treatment of Tregs with DAC followed by adoptive transfer to LPS-injured Treg-depleted animals increased BAL fluid active TGF-β concentration, as compared to ex vivo vehicle treatment. Tregs required TGF-β to effect repair following LPS injury (3), which indicated that peripherally induced Tregs (pTregs or iTregs) were likely the responsible fraction. However, thymus-derived natural Treg (tTreg or nTreg) expansion or recruitment might also have contributed to the lymphocyte response after lung injury, as adoptive transfer of $1 \times 10^6$ splenic nTregs mediated resolution in lymphocyte deficient mice (3,5). The CpG methylation signature of Treg gene loci distinguished committed thymus-derived Tregs and TGF-β-induced Tregs (10). The results were somewhat limited in that region-specific CpG methylation patterns were not measured directly; however, others have previously described that Treg induction in the presence of a DNMT inhibitor generated a thymus-derived Treg epigenetic profile (10,8,25). Lung Treg CpG methylation pattern analysis paired with gene expression profiling is currently pursued to identify the significance of Treg epigenetic signatures following injury and with DNMT inhibitor treatment.

The flow cytometric molecular phenotyping data suggested several mechanisms involved in DAC-enhanced injury repair. DNMT inhibition modestly augmented Foxp3 expression (19,24), which lead to increased Treg proliferation and immunoregulatory activity (11,20,21). The in vitro experiments described herein showed that DAC induced Foxp3 expression in non-Tregs. These results implicated that conversion of naïve CD4+ T cells into Foxp3+ cells (24) partially underlay the Treg increase observed in DAC-treated mice. However, the functional abilities of these converted cells remain unclear, at least in in vitro systems (46), and the results described herein showed a large difference in Foxp3 expression between DAC-induced Foxp3+ cells and Foxp3+ Tregs cultured with DAC. A recent report demonstrated that deletion of the DNMT adapter protein Uhrf1 within CD4+ cells reduced production of Tregs due to hypomethylation at the locus encoding the cyclin-dependent kinase inhibitor p21 (51). In contrast, the results described herein, indicated that demethylation in committed CD4+ CD25$^{hi}$Foxp3+ cells was different than demethylation in undifferentiated CD4+ cells, as demethylation in Foxp3+ cells led to proliferation of committed Tregs in vitro with in vivo data showing nominal effects on CD4+Foxp3− cells. Additionally, a study using mice with Dnmt1 deletion restricted to Foxp3+ cells suggested that Tregs required the Dnmt1 isoform to execute their suppressive program (52). In some embodiments, pharmacologic demethylation on an acute timescale can lead to different methylation patterns than those accompanying genetic deletion of Dnmt1.

Phenotypically, Treg CD39 surface expression increased in response to DAC after lung injury, indicating that extracellular ATP hydrolysis was involved as a mechanism by which Tregs exerted their pro-repair program following DNMT inhibition. Damaged cells released ATP into the extracellular milieu, where it exhibited multiple pro-inflammatory effects; CD39+ Treg-mediated ATP hydrolysis was identified to restore homeostasis to injured tissues (31). DAC did not increase Treg CD39 expression in the absence of inflammation—in vitro (FIG. 6) or following i.t. water. However, lung Treg CD39 expression increased following adoptive transfer of DAC-treated Tregs to an injured host. These data indicated that environmental conditions in the inflamed lung likely combined with the Treg epigenetic state to modulate gene and protein expression profiles. CTLA-4 was only slightly up-regulated upon systemic DAC treatment and although statistically different likely did not have biological relevance (32). Treg proliferation increased in response to DAC. Indeed, lung Treg number increased significantly in DAC-treated mice, as compared with vehicle, five days post-LPS, and DAC treatment led to robust proliferation following adoptive transfer. Finally, while not directly addressed by the instant experimental design, more efficient Treg homing to the inflamed lung also likely contributed to accelerated repair. Although DAC modestly increased individual Treg markers, the combined effect on Treg function was likely synergistic. Collectively, both a qualitative mechanism (augmentation of Treg suppressive function) and a quantitative mechanism (increased Treg proliferation) likely underlay the pro-resolution effect of DNMT inhibition.

Several questions were also raised by the current studies. For one, what other cell types underwent epigenetic changes in response to lung injury? A recent investigation showed that dual therapy with histone acetylation and DNA methylation modifiers could mitigate lung vascular hyperpermeability after systemic LPS injury in mice—an indirect lung injury model—via a beneficial effect on the pulmonary endothelium (53). Dynamic DNA methylation in non-Treg cells following lung injury remains to be explored. What DNA methylation pattern do Tregs that respond to lung injury display? Inhibition of Treg DNA methylation following injury promoted resolution, but it remained unclear if induced or thymus-derived Tregs drove lung injury repair. Future experiments employing lung Treg CpG methylation pattern analysis is expected to help determine the subset involved in the Treg response to injury. What effect does Treg plasticity have on the lung injury phenotype? Controversy surrounds whether committed Tregs undergo Foxp3 down-regulation or loss and assume T effector function in inflammatory environments (48,49). Since DNA demethylation was observed to stabilize Tregs, it is likely that pharmacologic DNMT inhibition following injury helps to maintain and stabilize Treg identity and mitigate any effect of Foxp3 loss that might otherwise occur (50). Fate-mapping experiments are expected to help elucidate how Treg plasticity affects lung injury pathology and resolution.

Thus, a role for regulatory T cell DNA methyltransferase inhibition in resolution of acute lung injury has been newly established. DNMT inhibition increased lung Treg frequency and suppressive phenotype and functioned to promote resolution. A therapeutic approach to treatment of lung injury has therefore been identified, and additional investigation into the epigenetic marks and mechanisms underlying the findings described herein are expected to further enhance therapeutic options for patients with ARDS and other acute inflammatory conditions.

Regulatory T Cells in Injury Repair

In certain aspects, the instant invention involves contacting Treg cells with a DNA methyltransferase inhibitor, to promote therapeutic effects of such treated Treg cells. Adoptive transfer experiments identified the Treg subpopulation as the active lymphocyte fraction involved in promoting repair, via its effects on macrophage function, neutrophil efferocytosis, epithelial proliferation (4), and limitation of fibroproliferation (5).

Tregs also had also been identified as promoting repair in other tissue damage models as well as clinical scenarios (6, 7). While Treg adoptive transfer may be a viable management strategy for chronic conditions (7), the briskly evolving nature of ARDS makes an adoptive transfer-based therapy impractical. Epigenetic mechanisms, such as those discovered in certain aspects of the instant invention, represent attractive targets to rapidly expand Treg numbers and enhance their function (8).

Tregs comprise a CD4+ lymphocyte subset that suppresses both innate and adaptive immune responses (9). Treg development and function require both epigenetic programming—prominently through DNA demethylation—and forkhead box protein 3 (Foxp3) transcription factor expression (10, 11). Constitutive Foxp3 expression was necessary for Treg suppressive activity (12, 13), and epigenetic marks tightly regulated transcription at the Foxp3 locus and the loci of other key Treg genes (10, 14). In mice and humans, distinct regions within Treg gene loci (including Foxp3) displayed cytosine-phospho-guanine (CpG) methylation patterns that differed between Tregs and CD4+ CD25− conventional T cells, with hypomethylation dominating in Tregs (10, 15-19). Importantly, Foxp3 expression was identified to correlate with Treg suppressive function (11, 20, 21).

Tregs coordinate repair following direct lung injury via effects on alveolar macrophage pro-inflammatory responses, neutrophil efferocytosis (3), alveolar epithelial regeneration (4), and limitation of fibrosis (5). In certain aspects of the invention, a key Treg feature—DNA demethylation—has been newly exploited to increase Treg frequency and suppressive phenotype and function following lung injury. While the specific Treg subset involved in injury resolution remains undefined, remarkable amelioration of recovery from acute lung injury was observed in performing the methods of the invention.

Tregs require transforming growth factor beta (TGF-β) to effect repair following LPS injury (3), which has suggested that peripherally induced Tregs (pTregs or iTregs) may be the responsible fraction. However, thymus-derived natural Treg (tTreg or nTreg) expansion and/or recruitment might also have contributed to the lymphocyte response after lung injury, as adoptive transfer of splenic nTregs mediated resolution in lymphocyte deficient mice (3,5). The CpG methylation signature of Treg gene loci distinguishes committed thymus-derived Tregs and TGF-β-induced Tregs (10). Treg induction in the presence of a DNMT inhibitor also generated a thymus-derived Treg epigenetic profile (8,10,25).

It is further contemplated that the significance of Treg epigenetic signatures following injury can be further surveyed by identifying lung Treg CpG methylation patterns, paired with gene expression profiling.

Flow cytometric molecular phenotyping data disclosed herein indicated that several mechanisms were involved in DAC-enhanced injury repair. DNMT inhibition augmented Foxp3 expression, a consequence likely attributable to DNA demethylation (19,24). Foxp3 critically drives Treg molecular biology, and enhanced Foxp3 expression led to increased Treg proliferation and activity in other studies (11,20,21). The in vitro experiments of the below examples showed that DAC induced Foxp3 expression in non-Tregs.

The results of the current examples also lent support to the idea that conversion of naïve CD4+ T cells into Foxp3+ cells (24) partially underpinned the Treg increase observed in DAC-treated mice. However, the functional abilities of these converted cells remains unclear, at least in in vitro systems (46), and these data showed an approximately 50-fold difference in Foxp3 mean fluorescence intensity between DAC-induced Foxp3+ cells and Foxp3+ Tregs cultured with DAC.

Phenotypically, Treg CD39 surface expression increased in response to DAC after lung injury, indicating extracellular ATP hydrolysis as a likely mechanism by which Tregs exerted their pro-repair program following DNMT inhibition. Damaged cells released ATP into the extracellular milieu, where it exhibited multiple pro-inflammatory effects; CD39+ Treg-mediated ATP hydrolysis can restore homeostasis to injured tissues (31). DAC did not increase Treg CD39 expression in the absence of inflammation—in vitro (FIG. 6) or following i.t. water (data not shown). However, lung Treg CD39 expression increased following adoptive transfer of DAC-treated Tregs to an injured host. These data indicated that environmental conditions in the inflamed lung likely combined with the Treg epigenetic state to modulate gene and protein expression profiles. CTLA-4 was modestly up-regulated with DAC treatment; these nominal increases might be significant, as CTLA-4 transmits a potent negative signal in the immunological synapse (32). CD25 expression was not modified by DNMT inhibition, potentially due to minimal pre-existing methylation at the Treg Il2ra gene locus (10). Finally, Treg Ki-67 expression increased in response to DAC, indicating an increased proliferative capacity. Indeed, lung Treg frequency increased over 2-fold in DAC-treated mice compared with vehicle five days post-LPS, and DAC treatment led to a robust proliferation following adoptive transfer. Collectively, both a qualitative mechanism (augmentation of Treg suppressive function) and a quantitative mechanism (increased Treg proliferation) was identified as likely responsible for the pro-resolution effect of DNMT inhibition in methods and compositions of the current invention.

DNA Methyltransferases as Epigenetic Modulatory Agents

DNA methyltransferases (DNMTs) control de novo CpG methylation and methylation maintenance during cell division and development (22). CpG methylation within promoters and transcription factor binding sites represses gene transcription, and DNMT inhibition or knockdown led to DNA demethylation. DNMTs determine Foxp3 expression and Treg identity, as DNMT silencing or inhibition via siRNA or 5-aza-2'-deoxycytidine (DAC), respectively, led to Foxp3 expression and Treg phenotype in naïve CD4+ non-Treg cells (17,23-25).

The DNA methyltransferase inhibitor 5-aza-2'-deoxycytidine accelerated resolution of experimental lung injury via a salutary effect on Treg phenotype and function. Epigenetic manipulation of the regulatory T cell lineage was thus identified as an attractive therapeutic strategy for the acute respiratory distress syndrome and other acute inflammatory disorders.

DNA Methyltransferases and Regulatory T (Treg) Cells

Acute respiratory distress syndrome (ARDS) is a common and lethal inflammatory condition without effective pharmacotherapy. CD4+CD25+Foxp3+ regulatory T cells (Tregs) resolve lung inflammation, but mechanisms that enhance Tregs to promote resolution of established damage have heretofore remained unknown. DNA methyltransferases repress gene transcription by catalyzing DNA methylation at CpG residues within gene promoters and transcription factor binding sites. DNA demethylation at the forkhead box protein 3 (Foxp3) locus and other key Treg loci typify the Treg lineage.

DNMT inhibition increases lung Treg frequency and suppressive phenotype and function after injury; moreover, Tregs mediated the pro-resolution effect of DNMT inhibition. Epigenetic pathways represent novel manipulable targets for the treatment of the acute respiratory distress syndrome. The epigenetic marks and mechanisms underlying the current findings promote contemplation of therapeutic options for patients with the acute respiratory distress syndrome and other acute inflammatory conditions.

Since DNA demethylation stabilized Tregs, it was possible that pharmacologic DNMT inhibition following injury helped to maintain Treg identity and mitigated any effect of Foxp3 loss that might otherwise have occurred (50). It is contemplated that fate-mapping experiments can help elucidate how Treg plasticity affects lung injury pathology and resolution.

IL-4 Treatment of ARDS

Despite intense investigation, acute respiratory distress syndrome (ARDS) has remained an enormous clinical problem for which no specific therapies have previously existed. As described herein, intratracheal lipopolysaccharide or *Pseudomonas* bacteria administration was used to model experimental acute lung injury (ALI) and to further understand mediators of the resolution phase of ARDS. Recent work has demonstrated that macrophages transition from a predominant pro-inflammatory M1 phenotype during acute inflammation to an anti-inflammatory M2 phenotype with ALI resolution. The hypothesis that IL-4, a potent inducer of M2-specific protein expression, would accelerate ALI resolution and lung repair through reprogramming of endogenous inflammatory macrophages was tested. IL-4 treatment was found to offer dramatic and surprising benefits following delayed administration to mice that had been subjected to experimental ALI, including increased survival, accelerated resolution of lung injury, and improved lung function. As demonstrated herein, expression of the M2 proteins Arg1, FIZZ1 and Ym1 was increased in lung tissues following IL-4 treatment, and among macrophages, FIZZ1 was most prominently upregulated in the interstitial subpopulation. A similar trend was observed for the expression of macrophage mannose receptor (MMR) and Dectin-1 on the surface of alveolar macrophages following IL-4 administration. Macrophage depletion or STAT6 deficiency abrogated the therapeutic effect of IL-4. Collectively, these data demonstrated that IL-4-mediated therapeutic macrophage reprogramming could accelerate resolution and lung repair despite delayed use following experimental ALI. IL-4 or other similar therapies that target late-phase, pro-resolution pathways have thus been identified herein for treatment of human ARDS.

Acute respiratory distress syndrome (ARDS) is a severe form of diffuse lung disease that imposes a substantial acute and chronic health burden in the United States (94, 102). Both the severity of ARDS and a failure to resolve ongoing inflammation increase mortality and prolong morbidity in survivors (94). Despite intense investigation into understanding ARDS pathogenesis, there has until now been no effective pharmacotherapy, and management has been primarily supportive (54, 70, 80, 88).

Investigation in experimental acute lung injury (ALI) models has primarily focused on interrupting the early pathophysiologic events (24-48 hours) of ALI/ARDS, but this strategy has resulted in limited clinical utility of those interventions in humans with ARDS. In contrast, a focus on identifying mediators of ALI resolution may provide a clinically relevant time frame during which intervention is feasible for humans with ARDS. The critical importance of regulatory T cells (Tregs) to resolve experimental acute lung injury (ALI) (59) was demonstrated. More recently, macrophages have also been shown to be necessary for resolution of severe lung inflammation (57).

Lung inflammation has been described as intimately associated with a phenotypically and functionally diverse set of monocytes and macrophages (69, 81, 95). Early macrophage classification of phenotypes included M1 (classically-activated or pro-inflammatory) or M2 (alternatively-activated or anti-inflammatory). In response to signaling via pattern recognition receptors (103, 104), macrophages become M1, possess strong microbiocidal activity, and secrete high levels of pro-inflammatory cytokines. However, persistence of M1 macrophages can be detrimental to wound healing (96). Experimental ALI models have demonstrated macrophage transformation from a predominant M1 phenotype during acute inflammation to a pro-resolution, M2 phenotype with initiation of lung repair and restoration of tissue homeostasis (56, 73). M2 macrophages have been identified as elicited by IL-4 and/or IL-13 in a STAT6-dependent manner, and have been commonly identified in the mouse by surface expression of mannose receptor, and intracellular expression of arginase-1 (Arg1), chitinase-like 3 (Ym1), and FIZZ1 (Relmα) (68). M2 macrophages have been believed to be important in wound healing and can promote tissue repair by limiting Th2-associated cellular inflammation, cytokine production, and fibroproliferation (86, 90, 91). Yet, a causal role for pro-resolution M2 macrophages during ALI resolution and lung repair has not previously been established.

Having recognized a M1 to M2 phenotypic transition during the resolution phase of acute lung inflammation, whether exogenously-administered IL-4 could induce M2 macrophages (identified as highly plastic in nature) that promote resolution of experimental ALI and enhance lung repair was examined As described herein, IL-4 therapy decisively and surprisingly accelerated resolution of sterile and infection-induced lung inflammation, and required macrophages and Stat6 expression to orchestrate this response.

Summary of IL-4 Therapy Results

As identified herein, delayed IL-4 therapy offered dramatic benefits following both sterile and infection-induced experimental ALI. Specifically, IL-4 improved mortality, accelerated resolution of lung injury, and restored lung function. Lung macrophages and STAT6 transcription factor expression were necessary for IL-4 to exert its therapeutic effects on lung injury resolution; Tregs, on the other hand, did not appear to be required. Prior to ALI resolution and lung repair, the M2 proteins Arg1, FIZZ1, and Ym1 were increased in the lung with IL-4 treatment, and among macrophages FIZZ1 upregulation was most pronounced in the interstitial sub-population. In addition, the importance of the interstitial macrophage sub-population towards IL-4-derived ALI resolution was further supported by their preferential depletion in intravenous liposomal clodronate experiments.

Study of experimental ALI models has been used to gain understanding of relevant biological pathways in human ARDS. Since the majority of ARDS cases are diagnosed after patients are hospitalized with acute lung inflammation (78), using IL-4 as a therapy to target late-phase, pro-resolution pathways is expected to be more effective in improving survival and restoring lung function (63). Researchers in ARDS have begun to focus on understanding the resolution phase in order to generate pharmacologic targets and even potential therapeutics, with an emphasis on epithelial and endothelial barrier restoration as well as neutrophil clearance (82). Despite their prominent role in neutrophil clearance, however, little previous effort has been invested to determine a primary role for macrophages to accelerate resolution of lung inflammation and enhance lung repair. For some time, it has been known that increased BAL macrophage number and phenotypic maturity have been associated with improved outcomes in human ARDS (93, 98), but such efforts have yet to define specific macrophage contributions to the active process of ARDS resolution.

Given the interest in knowing whether exogenous IL-4 could accelerate resolution and lung repair in a macrophage-dependent manner, the kinetics of endogenous IL-4 secretion were not examined, and no attempts to identify cellular sources of IL-4 were made, though work is currently underway to examine these relationships. In addition to its many potential cellular sources, measuring secreted IL-4 is expected to have limited utility due to its high receptor binding affinity to myeloid cells, which are abundantly present in circulation and in inflamed tissue (77). In fact, the rationale for complexing exogenous IL-4 to its antibody at ~2:1 molar ratio prior to delivery has been one of prolonging in vivo IL-4 activity from about 30 minutes to more than 24 hours (65). As such, the enthusiasm for the therapeutic potential of IL-4 is not expected to be diminished by prior reports that have demonstrated a lack of consistent association between serum or BAL IL-4 levels and better outcomes in human ARDS (58, 84). Furthermore, blocking endogenous IL-4 impaired ALI resolution and reduced expression of M2 macrophage proteins, and therefore have strongly supported the importance of IL-4 in endogenous ALI resolution.

Mitigating influx and enhancing removal of accumulated alveolar neutrophils has been identified as a hallmark of resolution of lung inflammation (79). M2 macrophages have been identified as effective at phagocytosis (61, 73), and IL-4 has been identified to restore impaired macrophage phagocytosis (64). Following infectious and sterile insults to the lung, IL-4 therapy resulted in a several-fold reduction in alveolar neutrophils at later time points. Therefore, a likely IL-4-mediated benefit is to enhance macrophage efferocytosis of apoptotic neutrophils to accelerate experimental ALI resolution. As another likely mechanism to enhance lung repair, IL-4 therapy reduced whole lung collagen, indicating that it likely also regulated fibroproliferation. Work by Huaux and colleagues also surmised an anti-fibrotic and immunoprotective effect of endogenous IL-4 early after bleomycin-induced lung injury, but also implicated a pro-fibrotic role during the reparative phase (74). The variable effects of IL-4 on fibrosis during different phases of the bleomycin model has highlighted that timing is of critical importance in lung inflammatory models, and has emphasized that testing therapies in more than one experimental ALI model is likely an important step towards translation to human ARDS (83).

Although M1 macrophages have been identified as typically associated with enhanced microbial phagocytosis and killing of intracellular bacteria via iNOS, TNF-α, IL-12 production (73), IL-4 reprogramming of M2 macrophages was observed to accelerate ALI resolution in the infection model described herein, without any apparent detrimental effects on bacterial clearance. M2 macrophages were reported to possess increased phagocytic activity via upregulation of Fc or scavenger receptors (61). Although on-going bacterial replication occurring simultaneously with IL-4 therapy could present a cause for concern in the clinical realm or in other infectious experimental models, macrophages have been characterized as a highly plastic cell, which therefore would likely reprogram to a predominant M1 phenotype in response to infection-induced signaling of pattern recognition receptors. Furthermore, in mice, and in at least some reports in humans, a significant percentage of quiescent alveolar macrophages have been identified to display an M2 phenotype with prominent mannose receptor expression (85, 89, 105), yet have exhibited undiminished capacity to initiate a robust pro-inflammatory response to infectious and non-infectious stimuli. Therefore, in some embodiments, not only has IL-4 therapy been identified to accelerate ALI resolution and lung repair, it likely has also promoted homeostasis by reprogramming lung macrophages back to their quiescent, predominantly M2 phenotypic state.

Unexpectedly, the salutary effects of IL-4 on lung repair did not require Tregs. Although this finding seemed at odds with other work, in fact it has been shown that Tregs can resolve lung inflammation by abrogating pro-inflammatory macrophage responses and, like IL-4, by reprogramming macrophages towards an M2 phenotype (59). Indeed, the work by Taams and colleagues showed that human Tregs dampened LPS-induced M1 monocyte pro-inflammatory responses while promoting an M2 phenotype (99, 101). Moreover, the prospect that Tregs provide an important IL-4 source, and as such, likely regulate macrophage phenotype and function during lung inflammation as a mechanism to support endogenous resolution, should not be excluded. Therefore, IL-4 treatment is expected to obviate the need for endogenous Treg-derived IL-4, likely explaining the lack of Treg requirement. Noting the ability of IL-4 to induce endogenous Treg proliferation and maintain their suppressive function (87), in some embodiments, IL-4 treatment is expected to exert a synergistic pro-repair effect by programming macrophages and Tregs.

IL-4 treatment was used instead of IL-13, the latter of which has also been described to signal through a macrophage IL-4 receptor to promote M2 protein expression. IL-4 has previously been described to induce more robust expression of M2 genes (72) and is also believed to be less likely to induce fibrosis (73). In addition to IL-4- or IL-13-derived M2 macrophages, there are several other subtypes of anti-inflammatory macrophages that are not addressed here yet would be predicted as important for endogenous repair pathways (56). Recent work has identified macrophages derived from stimulation with high-density immune complexes as expressing elevated levels of IL-10 and protecting from lethal endotoxemia in a STAT6-independent fashion (66). Signaling pathways that do not require STAT6 to induce M2 marker expression include IL-6/IL-10/STAT3- and TLR/MyD88/C/EBP, and both have also been described as of significance in experimental ALI (60, 92). In certain embodiments, the therapeutic benefits of IL-4 and M2 marker expression are expected to be amplified by similar STAT6-independent autocrine or paracrine signals. In the i.t. LPS model, IL-4 signaling through macrophage STAT6 appeared necessary to accelerate ALI resolution, indicating that the specific cytokine activity was critical. Given that the current data have associated select M2 markers with accelerated ALI resolution, however, a detailed molecular characterization of endogenous and IL-4-elicited macrophages supported by additional mechanistic studies is expected to further delineate a critical role for specific M2-associated genes.

Despite intensive investigation in ARDS pathogenesis, translation of therapies has been largely disappointing in human ARDS. In certain aspects of the current invention, a novel therapeutic agent, IL-4, that has been newly described to resolve sterile and non-sterile lung inflammation robustly, has been identified. By reprogramming macrophages into a critical pro-repair phenotype, a novel cellular player to promote ALI resolution and lung repair was also identified. Importantly, IL-4 treatment was administered as an effective rescue therapy, well after the onset of experimental ALI, indicating translational potential for other injuries, diseases and/or disorders.

Macrophages and Recovery from Lung Injury

The present invention is based, at least in part, upon identification of modulation of macrophages—specifically, enhancing transition of lung (e.g. alveolar) macrophages from an M1 phenotype to M2 phenotype—as a factor underlying accelerated recovery from acute lung injury of IL-4-treated subjects. Exemplary references that have identified macrophages as critical for resolution of lung inflammation include:

D'Alessio F R, Tsushima K, Aggarwal N R, Mock J R, Eto Y, Garibaldi B T, Files D C, Avalos C R, Rodriguez J V, Waickman A T, Reddy S P, Pearse D B, Sidhaye V K, Hassoun P M, Crow M T, King L S. Resolution of experimental lung injury by monocyte-derived inducible nitric oxide synthase. Immunol. 2012 Sep. 1; 189(5): 2234-45.

Aggarwal N R, D'Alessio F R, Eto Y, Chau E, Avalos C R, Waickman A T, Garibaldi B T, Mock J R, Files D C, Sidhaye V K, Polotsky V Y, Powell J, Horton M R, King L S. Macrophage adenosine receptor 2a (A2aR) protects against oxygen-induced augmentation of experimental lung injury. Am J Respir Cell Mol Biol. 2013 Jan. 24.

Aggarwal N R, King L S, and D'Alessio F R. Diverse macrophage populations mediate acute lung inflammation and resolution. Am J Physiol Lung Cell Mol Physiol, 2014 Feb. 7. PMID 24508730.

Aggarwal N R, Tsushima K, Eto Y, Tripathi A, Mandke P, Mock J R, Garibaldi B T, Singer B D, Sidhaye V K, Horton M R, King L S, D'Alessio F R Immunological Priming Requires Tregs and Interleukin-10-Producing Macrophages to Accelerate Resolution from Severe Lung Inflammation. J Immunol. 2014 Mar. 31. PMID: 24688024.

IL-4 Agents

Administration of IL-4, specifically recombinant forms of IL-4, was identified to accelerate recovery from acute lung injury. Exemplary forms of recombinant IL-4 include recombinant murine IL-4, which is a 13.5 kDa globular protein containing the following 121 amino acid residues, derived from an *E. coli* source: MHIHGCDKNHLREIIGIL-NEVTGEGTPCTEMDVPNVLTATKNTTE-SELVCRASKVLRI FYLKHGKTPCLK-KNSSVLMELQRLFRAFRCLDSSISCTMNESKSTSLKD-FLESLKSIM QMDYS (SEQ ID NO: 1). This recombinant form presents the fusion of a start methionine with residues 21 to 140 of GenBank accession number AAT73594.1. Synonyms for recombinant murine IL-4 include BCGF, BCDF and B cell stimulating factor (BSF-1). The nucleotide sequence of recombinant murine IL-4 is:

(SEQ ID NO: 2)
5'-ATGCACATACACGGATGCGACAAAAATCATCTTCGGGAGATTATTGG

GATCCTGAACGAGGTGACGGGAGAAGGAACCCCATGCACCGAGATGGACG

TCCCCAACGTTCTGACTGCCACTAAGAACACAACTGAAAGTGAACTCGTA

TGCCGCGCATCGAAGGTTTTGCGAATATTTTACCTTAAGCACGGGAAGAC

TCCGTGCTTGAAAAAGAACTCATCGGTTCTCATGGAATTGCAAAGACTTT

TCCGCGCCTTCCGGTGCCTCGACTCGTCTATTTCTTGCACTATGAACGAG

TCAAAAAGTACCAGTCTTAAAGATTTCCTCGAAAGCCTTAAGAGTATAAT

GCAGATGGATTATAGC-3'.

An example of a corresponding human IL-4 sequence is that of recombinant human IL-4, chain A, locus 1ITL, having accession number GI:157831503, which is a 15.1 kDa globular protein containing amino acid residues manufactured using all non-animal reagents: MHKCDITLQEIIKTLNSLTEQKTLCTELTVTDI-FAASKNTTEKETFCRAATVLRQFYSH HEKDTRCL-GATAQQFHRHKQLIRFLKRLDRNLWGLAGLN-SCPVKEANQSTLENFLE RLKTIMREKYSKCSS (SEQ ID NO: 3). This form presents the fusion of a start methionine with residues 25 to 153 of GenBank accession number AAT73594.1. The $ED_{50}$ for certain effects assessed for recombinant human IL-4 has been characterized as typically 6-30 pg/mL in solution. The nucleotide sequence of human recombinant IL-4 is: 5'-

(SEQ ID NO: 4)
ATGCACATACACGGATGCGACAAAAATCATCTTCGGGAGATTATTGGGATC

CTGAACGAGGTGACGGGAGAAGGAACCCCATGCACCGAGATGGACGTCCCC

AACGTTCTGACTGCCACTAAGAACACAACTGAAAGTGAACTCGTATGCCGC

GCATCGAAGGTTTTGCGAATATTTTACCTTAAGCACGGGAAGACTCCGTGC

TTGAAAAAGAACTCATCGGTTCTCATGGAATTGCAAAGACTTTTCCGCGCC

TTCCGGTGCCTCGACTCGTCTATTTCTTGCACTATGAACGAGTCAAAAAGT

ACCAGTCTTAAAGATTTCCTCGAAAGCCTTAAGAGTATAATGCAGATGGAT

TATAGC-3'.

Variant forms of human IL-4 polypeptide are also known in the art, including those of GenBank Accession Nos. 1HIJ_A GI:157831337 (chain A, Interleukin-4 mutant with Arg 88 replaced with Gln (R88q)); 2D48_A GI:109157435 (chain A, crystal structure of the Interleukin-4 variant T13d); 1HZI_A GI:15826610 (chain A, Interleukin-4 mutant E9a); and 2B8Z_A GI:109157203 (chain A, crystal structure of the Interleukin-4 variant R85a).

Mouse IL-4 mRNA consists of the sequence of GenBank Accession No. M25892.1 GI:533236, while an exemplary human IL-4 mRNA sequence is that of GenBank Accession No. M13982.1 GI:186334. As will be clear to the skilled artisan, a variety of nucleotide sequences are available and are contemplated herein for encoding of the IL-4 polypeptide sequences of the invention. As described in the following references, IL-4 in recombinant form is safe for human use and can be used as immunotherapy: Ghoreschi K, Thomas P, Breit S, Dugas M, Mailhammer R, Van Eden W, et al. Interleukin-4 therapy of psoriasis induced Th2 responses and improves human autoimmune disease. Nat Med 2003; 9:40-46.

Wong H L, Lotze M T, Wahl L M, Wahl S M. Administration of recombinant IL-4 to humans regulates gene expression, phenotype, and function in circulating monocytes J Immunol 1992; 148:2118-2125

In addition to IL-4, including recombinant IL-4, and fragments thereof, agonists of IL-4Rα are also contemplated for inclusion in the pharmaceutical compositions and use in the methods of the instant invention. Exemplary forms of IL-4 Rα agonists include mutein forms of IL-4 as set forth in Shanafelt et al. *Proc. Natl. Acad. Sci. USA* 95: 9454-94, while activating antibodies directed to IL-4Rα are also contemplated.

IL-4 Activity

Interleukin 4 (IL-4) is a cytokine that induces differentiation of naïve helper T cells (Th0 cells) to Th2 cells. Upon activation by IL-4, Th2 cells subsequently produce additional IL-4 in a positive feedback loop. The cell that initially produces IL-4, thus inducing Th0 differentiation, has not been identified, but recent studies suggest that basophils may be the effector cell. It is closely related and has functions similar to Interleukin 13. It has many biological roles, including the stimulation of activated B-cell and T-cell proliferation, and the differentiation of B cells into plasma cells. It is a key regulator in humoral and adaptive immunity. IL-4 induces B-cell class switching to IgE, and up-regulates MHC class II production. IL-4 decreases the production of Th1 cells, macrophages, IFN-gamma, and dendritic cell IL-12. Overproduction of IL-4 is associated with allergies.

Tissue macrophages play an important role in chronic inflammation and wound repair. The presence of IL-4 in extravascular tissues promotes alternative activation of macrophages into M2 cells and inhibits classical activation of macrophages into M1 cells. An increase in repair macrophages (M2) is coupled with secretion of IL-10 and TGF-β that result in a diminution of pathological inflammation. Release of arginase, proline, polyaminases and TGF-β by the activated M2 cell is tied with wound repair and fibrosis.

The receptor for Interleukin-4 is known as the IL-4Rα. This receptor exists in 2 different complexes throughout the body. Type 1 receptors are composed of the IL-4Rα subunit with a common y chain and specifically bind IL-4. Type 2 receptors consist of an IL-4Rα subunit bound to a different subunit known as IL-13Rα1, and have the ability to bind both IL-4 and IL-13, two cytokines with closely related biological functions. IL-4 also has been shown to drive mitogenesis, dedifferentiation, and metastasis in rhabdomyosarcoma. IL-4, along with other Th2 cytokines, is involved in the airway inflammation observed in the lungs of patients with allergic asthma.

Lung Injury

Acute lung injury caused by a wide variety of insults (including ventilation-induced lung injury) results in increased pulmonary capillary permeability and pulmonary edema without any increase in capillary or left atrial pressures: so called "low pressure edema" or ARDS. This is the single most common pulmonary complication of ICU patients, and accounts for a tremendous burden of morbidity and mortality.

Acute respiratory distress syndrome (ARDS), the clinical correlate of severe acute lung injury (ALI) in humans, is an important cause of morbidity and mortality in critically ill patients. Acute respiratory distress syndrome (ARDS) is a devastating disease hallmarked by acute inflammation of the lungs, and results in severe lung damage and an attributable mortality of 30-40%. Yet there is no effective therapy. Infectious etiologies, such as sepsis and pneumonia (including influenza and SARS), are leading causes of ALI/ARDS. Therefore, the treatment of these diseases or disorders (e.g., sepsis, pneumonia, influenza and/or SARS) using the agents of the invention is also contemplated. Histologically, ALI/ARDS in humans is characterized by a severe acute inflammatory response in the lungs and neutrophilic alveolitis. Inflammatory stimuli from microbial pathogens, such as endotoxin (lipopolysaccharide, LPS), are well recognized for their ability to induce pulmonary inflammation, and experimental administration of LPS, both systemically and intratracheally, has been used to induce pulmonary inflammation in animal models of ALI.

The physiological hallmark of ARDS is disruption of the alveolar-capillary membrane barrier (i.e., pulmonary vascular leak), leading to development of non-cardiogenic pulmonary edema in which a proteinaceous exudate floods the alveolar spaces, impairs gas exchange, and precipitates respiratory failure. Both alveolar epithelial and endothelial cell injury and/or death have been implicated in the pathogenesis of ALI/ARDS (1). However, despite decades of research, few therapeutic strategies for clinical ARDS have emerged and current specific options for treatment are limited. ARDS continues to be an important contributor to prolonged mechanical ventilation in the intensive care unit (ICU), and ARDS-associated mortality remains high at 30-50% despite optimal ICU supportive care.

ARDS is a complex clinical syndrome which is initiated by injury to the lung, often in the setting of pneumonia and/or sepsis, and aggravated by ventilator-induced injury. Some of the early features of ARDS can be reproduced by administration of bacterial endotoxin (LPS), which acts via Toll-like receptor 4 (TLR4), to increase the expression of inflammatory cyitokines and chemokines, and upregulate leukocyte adhesion molecules, results in EC activation.

Contemplated treatments for ARDS include treatments that involve decreasing lung inflammation, decreasing septal edema, decreasing alveolar and/or endothelial inflammation, or alleviating another symptom of the ARDS.

Acute lung injury (ALI) and acute respiratory distress syndrome (ARDS) were defined by a panel of experts in 2011 (an initiative of the European Society of Intensive Care Medicine endorsed by the American Thoracic Society and the Society of Critical Care Medicine) as the Berlin Definition. Presently there are three stages: mild, moderate, and severe with an associated increased mortality (27%; 95% CI, 24%-30%; 32%; 95% CI, 29%-34%; and 45%; 95% CI, 42%-48%, respectively; $P<0.001$) and increased median duration of mechanical ventilation in survivors (5 days; interquartile [IQR], 2-11; 7 days; IQR, 4-14; and 9 days; IQR, 5-17, respectively; $P<0.001$). The definition was empirically evaluated using patient-level meta-analysis of 4188 patients with ARDS from 4 multicenter clinical data sets and 269 patients with ARDS from 3 single-center data sets containing physiologic information. The categories of ARDS are based on the degree of hypoxemia determined by the ratio of Pa02/Fi02 where the Pa02 is the partial pressure of oxygen in arterial blood and the Fi02 is the fraction of inspired oxygen. In particular, the categorization is as follows: (1) Mild ARDS: 200 mm Hg<Pa02/Fi02 and less than or equal to 300 mm Hg; (2) Moderate ARDS: 100 mm Hg<PaO2/FiO2 and less than or equal to<200 mm Hg; and (3) Severe ARDS: PaO2/FiO2 is less than or equal to 100 mm Hg.

The causes of ARDS have been enumerated, with the most common being: sepsis, aspiration, pneumonia, severe trauma (bilateral lung contusion, fat embolism after long bone fracture, sepsis that develops several days after severe trauma or burns, and massive traumatic tissue injury), massive transfusion, transfusion related acute lung injury, lung and hematopoietic stem cell transplantation, drugs and alcohol, and genetic determinants such as mutations in the surfactant protein B (SP-B) gene.

Management of ARDS includes treatment of the underlying condition, mechanical or noninvasive ventilation, fluid and hemodynamic therapy, treatment of opportunistic infection, nutrition, and pharmacologic therapy. Previously, there has been no specific pharmacologic therapy for ALI/ARDS. Agents that have failed in large trials include in part, glucocorticoids, alprostadil, surfactant, ketoconazole, N-acetylcysteine, procysteine, lisofylline, and site-inactivated recombinant factor VIIa.

ARDS persists as a devastating disease with no effective pharmacotherapies despite extensive insight into the initial inflammatory injury (36). Therefore, the examples described herein focused on events determining resolution of lung inflammation. Resolution of injury requires not only cessation of ongoing pathology but also active repair of damaged tissues (2,37). Here, it was shown that resolution could be accelerated by an IL-4 agent or a small molecule administered after lung injury establishment. DNMT inhibition did not modify early injury in the studies described herein, highlighting that dynamic changes in DNA methylation patterns likely occurred during resolution.

Many experimental studies of acute lung injury have focused on early pathogenesis. However, most ARDS patients present to the ICU well after the initial pathogenic events have already occurred. For this reason, the experiments described herein have focused upon resolution of established lung damage. Administration of IL-4 agents (e.g., rIL-4) to promote repair of established lung injury has heretofore not been described. Furthermore, epigenetic manipulation to promote repair of established lung injury has heretofore not been described either. Additionally, manipulating Tregs to enhance their pro-repair function with the goal of accelerating resolution of lung injury—via an epigenetic or other mechanism—has also heretofore not been described.

(Lipopolysaccharide)-induced pulmonary inflammation is a well-known and well documented animal model for ARDS. Measures of extent of inflammation include cell counts from bronchoalveolar lavage (BAL) and a measure of pro-inflammatory cytokine levels in BAL fluid and lung parenchymal homogenates. LPS-induced permeability in the lung (i.e. extent of Acute Lung Injury) can also be measured.

It is contemplated that strategies to selectively reduce endothelial inflammation in response to injury can be of benefit, not only in ALI and ARDS, but also in systemic inflammatory disorders such as the Systemic Inflammatory Response Syndrome, sepsis, Multiple Organ Dysfunction/Failure Syndrome, etc.

An IL-4 agent of the invention can be administered to a subject at any time after a lung injury event and/or after diagnosis of a lung injury or other disease or disorder in a subject. In certain embodiments, an IL-4 agent of the invention is administered to a subject at least 2-3 hours after the lung injury event, at least 6 hours after the lung injury event, at least 12 hours after the lung injury event, or at least 24 hours after the lung injury event. Optionally, an IL-4 agent of the invention is administered to a subject at least 36 hours, at least 48 hours, at least 72 hours, at least 4 days, at least 5 days, at least 6 days, at least 7 days, at least 8 days, at least 9 days, or at least 10 days after the lung injury event. In some embodiments, an IL-4 agent of the invention is administered to a subject within 1-3 or 2-3 hours, 6, 12, 18 or 24 hours after diagnosis of a lung injury or of an acute inflammatory disease or disorder. Optionally, an IL-4 agent of the invention is administered within 36 hours of diagnosis, within 48 hours of diagnosis, within 72 hours of diagnosis, within four days of diagnosis, within five days of diagnosis, within six days of diagnosis, within seven days of diagnosis, or at more than seven days from diagnosis of a lung injury or of an acute inflammatory disease or disorder. Dramatic improvement/recovery from a lung injury, acute inflammatory disease or disorder or influenza are noted/are predicted to occur in instances where treatment with an IL-4 agent of the invention occurs, e.g., 24-48 or more hours after a lung injury event and/or onset of an acute inflammatory disease or disorder or influenza.

A DNA methyltransferase inhibitor of the invention can be administered to a subject at any time after a lung injury event and/or after diagnosis of a lung injury or other disease or disorder in a subject. In certain embodiments, a DNMT inhibitor of the invention is administered to a subject at least 2-3 hours after the lung injury event, at least 6 hours after the lung injury event, at least 12 hours after the lung injury event, or at least 24 hours after the lung injury event. Optionally, a DNMT inhibitor of the invention is administered to a subject at least 36 hours, at least 48 hours, at least 72 hours, at least 4 days, at least 5 days, at least 6 days, at least 7 days, at least 8 days, at least 9 days, or at least 10 days after the lung injury event. In some embodiments, a DNMT inhibitor of the invention is administered to a subject within 1-3 or 2-3 hours, 6, 12, 18 or 24 hours after diagnosis of a lung injury or of an acute inflammatory disease or disorder. Optionally, a DNMT inhibitor of the invention is administered within 36 hours of diagnosis, within 48 hours of diagnosis, within 72 hours of diagnosis, within four days of diagnosis, within five days of diagnosis, within six days of diagnosis, within seven days of diagnosis, or at more than seven days from diagnosis of a lung injury or of an acute inflammatory disease or disorder. Dramatic improvement/recovery from a lung injury, acute inflammatory disease or disorder or influenza are noted/are predicted to occur in instances where treatment with a DNA methyltransferase inhibitor of the invention occurs, e.g., 24-48 or more hours after a lung injury event and/or onset of an acute inflammatory disease or disorder or influenza.

Ex Vivo Therapy

To increase the Treg/pro-inflammatory T cells ratio, a cultured cellular preparation can be administered to the subject in a therapeutically effective amount. To do so, a T cell population containing Treg cells is obtained (e.g., via isolation from a subject) and is optionally cultured in vitro, with the cell population contacted with a DNA methyltransferase inhibitor to promote Treg activity and/or an expanded Treg cell population.

For certain ex vivo therapies of the invention, treated cells are (re)introduced into the pulmonary circulation by infusion of the cells either into a peripheral vein or a central vein, from where they move with the circulation to the pulmonary system, and become lodged in the smallest arterioles of the vascular bed of the lungs. Direct injection into the pulmonary circulation can also be adopted, for example through a Swan Ganz catheter. Injection into the right ventricle or right atrium may be carried out using the pacing port of a Swan Ganz catheter. The infusion can optionally be done in a bolus form i.e. injection of all the cells during a short period of time, or it may be accomplished by a continuous infusion of small numbers of cells over a long period of time, or alternatively by administration of limited size boluses on several occasions over a period of time. (Re)introduction of treated cells into the lungs can also be accomplished through inhalation of the cells using known pulmonary administration methods, such as an inhaler.

Where direct (re)introduction to the pulmonary system is performed, while the transferred, treated cells of ex vivo therapy applications of the invention can themselves largely or completely be retained in the pulmonary circulation, and especially in the arterioles of the patient's lungs, the expression products of the transgenes thereof are not restricted in this manner They can be expressed and secreted from the treated cells, and travel through the normal circulation of the patient to other, downstream body organs where they can exert a therapeutic effect. Thus, while one use of a process of the invention is in the treatment of pulmonary disorders, for those embodiments where the expression products initially contact the patient's pulmonary system, even such applications are not limited only to such treatments. The treated cells can optionally express products designed for treatment of other body organs of the patient. Such products expressed in the pulmonary system will target the other, predetermined organs and be delivered thereto by the natural circulation system of the patient.

It is also contemplated that an alternative means of increasing the Treg/pro-inflammatory T cell ratio involves the administration of the supernatant of a treated cell culture of Treg cells to a subject. In some embodiments, the cell culture supernatant can comprise certain cells or fractions (for example a part of the cytoplasmic membrane).

In related embodiments, testing for the possibility and/or development of an immune response is performed. It is possible to determine if two cells are considered immunogenic with respect to one another by conducting conventional in vitro assays, such as a mixed lymphocyte reaction. It is also expected that MHC-disparate cells would be considered immunogenic with respect to one another. Importantly, the cell culture supernatant, apart from being optionally filtered to remove cells and cellular debris, is not submitted to further extraction/size fractionation prior to its administration to the subject. The cell culture supernatant thus comprises the conditioned media from the cell culture (e.g. cellular by-products including the cytokines secreted by the cultured cells).

An alternative way of increasing the Treg/pro-inflammatory Tcell ratio in a subject to be treated, is to administer the plasma of an animal (such as a rodent) that has been treated with a DNMT inhibitor. In some embodiments, this plasma can comprise Treg cells of the animal or a derivative therefrom (a part of the cytoplamsic membrane from the Treg cell, for example). Processes for obtaining the plasma from an animal are known to those skilled in the art and usually include a cell lysis (to remove erythrocytes) as well as centrifugation. Importantly, the plasma, apart from being optionally filtered to remove cells and cellular debris, is not submitted to further extraction/size fractionation prior to its administration to the subject. The plasma thus comprises the cellular by-products generated upon the treatment of Treg cells with a DNMT inhibitor (including the cytokines produced by the immune system).

Where direct (re)introduction to the pulmonary system is performed, while the transferred, treated cells of ex vivo therapy applications of the invention can themselves largely or completely be retained in the pulmonary circulation, and especially in the arterioles of the patient's lungs, the expression products of the transgenes thereof are not restricted in this manner They can be expressed and secreted from the treated cells, and travel through the normal circulation of the patient to other, downstream body organs where they can exert a therapeutic effect. Thus, while one use of a process of the invention is in the treatment of pulmonary disorders, for those embodiments where the expression products initially contact the patient's pulmonary system, even such applications are not limited only to such treatments. The treated cells can optionally express products designed for treatment of other body organs of the patient. Such products expressed in the pulmonary system will target the other, predetermined organs and be delivered thereto by the natural circulation system of the patient.

Mammalian cells such as the patient's own (i.e. autologous) or cells from another individual (i.e. allogeneic) cells can be cultured in vitro and treated with a DNMT inhibitor. Then the treated cells are introduced into the patient, so that the treated Treg cells can exert their effect in the body, for therapeutic purposes. Following DNMT inhibitor treatment of a T cell-containing population, selective culturing of (active) Treg cells can be performed, so that administration of the cells to the patient can be limited to the (active) Treg. In other cases, all of the cells subject to the DNMT inhibitor treatment are administered.

It is contemplated that strategies to selectively reduce endothelial inflammation in response to injury could be of potential benefit, not only in ALI and ARDS, but also in systemic inflammatory disorders such as the Systemic Inflammatory Response Syndrome, sepsis, Multiple Organ Dysfunction/Failure Syndrome, etc.

Pharmaceutical Compositions

In certain embodiments, the present invention provides for a pharmaceutical composition comprising an IL-4 agent or a DNA methyltransferase inhibitor employed in the present invention. The IL-4 agent or DNA methyltransferase inhibitor targeting lung injury can be suitably formulated and introduced into a subject or the environment of a cell by any means recognized for such delivery.

Such compositions typically include the agent and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The compositions of the invention could also be formulated as nanoparticle formulations.

The compounds of the invention can be administered for immediate-release, delayed-release, modified-release, sustained-release, pulsed-release and/or controlled-release applications.

The pharmaceutical compositions of the invention may contain from 0.01 to 99% weight-per volume of the active material.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans The dosage of such compounds lies preferably within a range of circulating concentrations that include the ED50 with little or no toxicity. The dosage may vary within this range depending upon the dosage form employed and the route of administration utilized. For a compound used in a method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of an IL-4 agent or a DNA methyltransferase inhibitor targeting lung injury (i.e., an effective dosage) depends on the IL-4 agent or DNA methyltransferase inhibitor selected. For instance, single dose amounts of an IL-4 agent or a DNA methyltransferase inhibitor targeting lung injury in the range of approximately 1 pg to 1000 mg may be administered; in some embodiments, 10, 30, 100, or 1000 pg, or 10, 30, 100, or 1000 ng, or 10, 30, 100, or 1000 μg, or 10, 30, 100, or 1000 mg may be administered. In some embodiments, 1-5 g of the compositions can be administered.

A therapeutically effective amount of the compound of the present invention can be determined by methods known in the art. In addition to depending on the IL-4 agent or DNA methyltransferase inhibitor selected/pharmaceutical formulation used, the therapeutically effective quantities of a pharmaceutical composition of the invention will depend on the age and on the general physiological condition of the patient and the route of administration. In certain embodiments, the therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of an IL-4 agent or a DNA methyltransferase inhibitor targeting lung injury can include a single treatment or, optionally, can include a series of treatments.

It can be appreciated that the method of introducing an IL-4 agent or a DNA methyltransferase inhibitor targeting lung injury into the environment of a cell will depend on the type of cell and the makeup of its environment.

Suitable amounts of an IL-4 agent or a DNA methyltransferase inhibitor targeting lung injury must be introduced and these amounts can be empirically determined using standard methods. Exemplary effective concentrations of individual IL-4 agent or DNA methyltransferase inhibitor species in the environment of a cell can be 500 millimolar or less, 50 millimolar or less, 10 millimolar or less, 1 millimolar or less, 500 nanomolar or less, 50 nanomolar or less, 10 nanomolar or less, or even compositions in which concentrations of 1 nanomolar or less can be used.

The pharmaceutical compositions can be included in a kit, container, pack, or dispenser together with instructions for administration.

Methods of Treatment

The present invention provides for both prophylactic and therapeutic methods of treating a subject at risk of (or susceptible to) a lung injury.

"Treatment", or "treating" as used herein, is defined as the application or administration of a therapeutic agent (e.g., an IL-4 agent or a DNA methyltransferase inhibitor) to a patient, or application or administration of a therapeutic agent to an isolated tissue or cell line from a patient, who has the injury, (or, where an isolated tissue or cell line is used, from a subject not having the injury, e.g., for transfer to isolated tissue, cell or supernatant to a patient having the injury) for a symptom of the injury, with the purpose to cure, heal, alleviate, relieve, alter, remedy, ameliorate, improve or affect the injury and/or the symptoms of the injury.

Thus, a role for regulatory T cell DNA methyltransferase inhibition was identified in resolution of acute lung injury. DNA methyltransferase inhibition markedly enhanced Treg function to accelerate lung injury repair in a mouse model.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (Danio rerio), (4th Ed., Univ. of Oregon Press, Eugene, 2000).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

REFERENCES

1. Rubenfeld G D, Caldwell E, Peabody E, Weaver J, Martin D P, Neff M, Stern E J, Hudson L D. Incidence and outcomes of acute lung injury. *N Engl J Med* 2005; 353:1685-1693.
2. Buckley C D, Gilroy D W, Serhan C N, Stockinger B, Tak P P. The resolution of inflammation. *Nat Rev Immunol* 2013; 13:59-66.
3. D'Alessio F R, Tsushima K, Aggarwal N R, West E E, Willett M H, Britos M F, Pipeling M R, Brower R G, Tuder R M, McDyer J F, King L S. CD4+CD25+Foxp3+ Tregs resolve experimental lung injury in mice and are present in humans with acute lung injury. *J Clin Invest* 2009; 119:2898-2913.
4. Mock J R, Garibaldi B T, Aggarwal N R, Jenkins J, Limjunyawong N, Singer B D, Chau E, Rabold R, Files D C, Sidhaye V, Mitzner W, Wagner E M, King L S, D'Alessio FR. Foxp3(+) regulatory T cells promote lung epithelial proliferation. Mucosal Immunol [serial online] 2014 May [cited 2014 May 23]; Available from: http://http//www.nature.com/mi/journal/vaop/ncurrent/full/mi201433a.html
5. Garibaldi B T, D'Alessio F R, Mock J R, Files D C, Chau E, Eto Y, Drummond M B, Aggarwal N R, Sidhaye V, King L S. Regulatory T cells reduce acute lung injury fibroproliferation by decreasing fibrocyte recruitment. *Am J Respir Cell Mol Biol* 2013; 48:35-43.
6. Burzyn D, Kuswanto W, Kolodin D, Shadrach J L, Cerletti M, Jang Y, Sefik E, Tan T G, Wagers A J, Benoist C, Mathis D. A special population of regulatory T cells potentiates muscle repair. *Cell* 2013; 155:1282-1295.
7. Singer B D, King L S, D'Alessio F R. Regulatory T cells as immunotherapy. *Front Immunol* 2014; 5:46.
8. Lal G, Bromberg J S. Epigenetic mechanisms of regulation of Foxp3 expression. *Blood* 2009; 114:3727-3735.
9. Sakaguchi S, Sakaguchi N, Asano M, Itoh M, Toda M Immunologic self-tolerance maintained by activated T cells expressing IL-2 receptor alpha-chains (CD25). Breakdown of a single mechanism of self-tolerance causes various autoimmune diseases. *J Immunol* 1995; 155:1151-1164.
10. Ohkura N, Hamaguchi M, Morikawa H, Sugimura K, Tanaka A, Ito Y, Osaki M, Tanaka Y, Yamashita R, Nakano N, Huehn J, Fehling H J, Sparwasser T, Nakai K, Sakaguchi S. T cell receptor stimulation-induced epigenetic changes and Foxp3 expression are independent and complementary events required for Treg cell development. *Immunity* 2012; 37:785-799.
11. Hori S, Nomura T, Sakaguchi S. Control of regulatory T cell development by the transcription factor Foxp3. *Science* 2003; 299:1057-1061.
12. Fontenot J D, Gavin M A, Rudensky A Y. Foxp3 programs the development and function of CD4+CD25+ regulatory T cells. *Nat Immunol* 2003; 4:330-336.
13. Josefowicz S Z, Rudensky A. Control of regulatory T cell lineage commitment and maintenance. *Immunity* 2009; 30:616-625.
14. Wilson C B, Rowell E, Sekimata M. Epigenetic control of T-helper-cell differentiation. *Nat Rev Immunol* 2009; 9:91-105.
15. Floess S, Freyer J, Siewert C, Baron U, Olek S, Polansky J, Schlawe K, Chang H-D, Bopp T, Schmitt E, Klein-Hessling S, Serfling E, Hamann A, Huehn J. Epigenetic control of the foxp3 locus in regulatory T cells. *PLoS Biol* 2007; 5:e38.
16. Janson P C J, Winerdal M E, Marits P, Thörn M, Ohlsson R, Winqvist O. FOXP3 promoter demethylation reveals the committed Treg population in humans. *PLoS One* 2008; 3:e1612.
17. Kim H-P, Leonard W J. CREB/ATF-dependent T cell receptor-induced FoxP3 gene expression: a role for DNA methylation. *J Exp Med* 2007; 204:1543-1551.
18. Mantel P-Y, Quaked N, Rückert B, Karagiannidis C, Welz R, Blaser K, Schmidt-Weber C B. Molecular mechanisms underlying FOXP3 induction in human T cells. *J Immunol* 2006; 176:3593-3602.
19. Toker A, Engelbert D, Garg G, Polansky J K, Floess S, Miyao T, Baron U, Düber S, Geffers R, Giehr P, Schallenberg S, Kretschmer K, Olek S, Walter J, Weiss S, Hori S, Hamann A, Huehn J. Active demethylation of the Foxp3 locus leads to the generation of stable regulatory T cells within the thymus. *J Immunol* 2013; 190:3180-3188.
20. Chauhan S K, Saban D R, Lee H K, Dana R. Levels of Foxp3 in regulatory T cells reflect their functional status in transplantation. *J Immunol* 2009; 182:148-153.
21. Van Loosdregt J, Fleskens V, Fu J, Brenkman A B, Bekker C P J, Pals C E G M, Meerding J, Berkers C R, Barbi J, Gröne A, Sijts A J A M, Maurice M M, Kalkhoven E, Prakken B J, Ovaa H, Pan F, Zaiss D M W, Coffer P J. Stabilization of the transcription factor Foxp3 by the deubiquitinase USP7 increases Treg-cell-suppressive capacity. *Immunity* 2013; 39:259-271.
22. Leonhardt H, Page A W, Weier H U, Bestor T H. A targeting sequence directs DNA methyltransferase to sites of DNA replication in mammalian nuclei. *Cell* 1992; 71:865-873.
23. Lal G, Zhang N, van der Touw W, Ding Y, Ju W, Bottinger E P, Reid S P, Levy D E, Bromberg J S. Epigenetic regulation of Foxp3 expression in regulatory T cells by DNA methylation. *J Immunol* 2009; 182:259-273.
24. Moon C, Kim S H, Park K S, Choi B K, Lee H S, Park J B, Choi G S, Kwan J H, Joh J W, Kim S J. Use of epigenetic modification to induce FOXP3 expression in naïve T cells. *Transpl Proc* 2009; 41:1848-1854.
25. Polansky J K, Kretschmer K, Freyer J, Floess S, Garbe A, Baron U, Olek S, Hamann A, von Boehmer H, Huehn J. DNA methylation controls Foxp3 gene expression. *Eur J Immunol* 2008; 38:1654-1663.
26. Singer B D, Mock J R, Garibaldi B T, Chau E, Aggarwal N R, Sidhaye V K, King L S, D'Alessio F R. Pharmacologic epigenetic manipulation rescues experimental lung injury and promotes lung regulatory T cell number and suppressive phenotype [abstract]. *Am J Respir Crit Care Med* 2013; 187:A1213.

27. Singer B D, Mock J R, Giibs K W, Garibaldi B T, Aggarwal N R, Sidhaye V K, King L S, D'Alessio F R. DNA demethylation promotes regulatory T cell-mediated resolution of acute lung injury [abstract]. *Am J Respir Crit Care Med* 2014; 189:A5575.

28. Collison L W, Vignali D A A. In vitro Treg suppression assays. *Methods Mol Biol* 2011; 707:21-37.

29. Festing M F W, Altman D G, Guidelines for the design and statistical analysis of experiments using laboratory animals. *ILAR J* 2002; 43:244-258.

30. Bollyky P L, Falk B A, Long S A, Preisinger A, Braun K R, Wu R P, Evanko S P, Buckner J H, Wight T N, Nepom G T. CD44 costimulation promotes FoxP3+ regulatory T cell persistence and function via production of IL-2, IL-10, and TGF-beta. *J Immunol* 2009; 183:2232-2241.

31. Borsellino G, Kleinewietfeld M, Di Mitri D, Sternjak A, Diamantini A, Giometto R, Höpner S, Centonze D, Bernardi G, Dell'Acqua M L, Rossini P M, Battistini L, Rötzschke O, Falk K. Expression of ectonucleotidase CD39 by Foxp3+ Treg cells: hydrolysis of extracellular ATP and immune suppression. *Blood* 2007; 110:1225-1232.

32. Wing K, Onishi Y, Prieto-Martin P, Yamaguchi T, Miyara M, Fehervari Z, Nomura T, Sakaguchi S. CTLA-4 control over Foxp3+ regulatory T cell function. *Science* 2008; 322:271-275.

33. Ni Y-F, Wang J, Yan X-L, Tian F, Zhao J-B, Wang Y-J, Jiang T. Histone deacetylase inhibitor, butyrate, attenuates lipopolysaccharide-induced acute lung injury in mice. *Respir Res* 2010; 11:33.

34. Kochanek A R, Fukudome E Y, Li Y, Smith E J, Liu B, Velmahos G C, DeMoya M, King D, Alam H B. Histone deacetylase inhibitor treatment attenuates MAP kinase pathway activation and pulmonary inflammation following hemorrhagic shock in a rodent model. *J Surg Res* 2012; 176:185-194.

35. Li Y, Liu B, Zhao H, Sailhamer E A, Fukudome E Y, Zhang X, Kheirbek T, Finkelstein R A, Velmahos G C, deMoya M, Hales C A, Alam H B. Protective effect of suberoylanilide hydroxamic acid against LPS-induced septic shock in rodents. *Shock* 2009; 32:517-523.

36. Ware L B, Matthay M A. The acute respiratory distress syndrome. *N Engl J Med* 2000; 342:1301-1308.

37. Serhan C N, Brain S D, Buckley C D, Gilroy D W, Haslett C, O'Neill L A J, Perretti M, Rossi A G, Wallace J L. Resolution of inflammation: state of the art, definitions and terms. *FASEB J* 2007; 21:325-332.

38. Trzonkowski P, Bieniaszewska M, Juścińska J, Dobyszuk A, Krzystyniak A, Marek N, Myśliwska J, Hellmann A. First-in-man clinical results of the treatment of patients with graft versus host disease with human ex vivo expanded CD4+CD25+CD127− T regulatory cells. *Clin Immunol* 2009; 133:22-26.

39. Brunstein C G, Miller J S, Cao Q, McKenna D H, Hippen K L, Curtsinger J, Defor T, Levine B L, June C H, Rubinstein P, McGlave P B, Blazar B R, Wagner J E. Infusion of ex vivo expanded T regulatory cells in adults transplanted with umbilical cord blood: safety profile and detection kinetics. *Blood* 2011; 117:1061-1070.

40. Di Ianni M, Falzetti F, Carotti A, Terenzi A, Castellino F, Bonifacio E, Del Papa B, Zei T, Ostini R I, Cecchini D, Aloisi T, Perruccio K, Ruggeri L, Balucani C, Pierini A, Sportoletti P, Aristei C, Falini B, Reisner Y, Velardi A, Aversa F, Martelli M F. Tregs prevent GVHD and promote immune reconstitution in HLA-haploidentical transplantation. *Blood* 2011; 117:3921-3928.

41. Hippen K L, Merkel S C, Schirm D K, Sieben C M, Sumstad D, Kadidlo D M, McKenna D H, Bromberg J S, Levine B L, Riley J L, June C H, Scheinberg P, Douek D C, Miller J S, Wagner J E, Blazar B R. Massive ex vivo expansion of human natural regulatory T cells (T(regs)) with minimal loss of in vivo functional activity. *Sci Transl Med* 2011; 3:83ra41.

42. Hoffmann P, Eder R, Kunz-Schughart LA, Andreesen R, Edinger M. Large-scale in vitro expansion of polyclonal human CD4(+)CD25high regulatory T cells. *Blood* 2004; 104:895-903.

43. Matute-Bello G, Frevert C W, Martin T R. Animal models of acute lung injury. *Am J Respir Cell Mol Biol* 2008; 295:L379-L399.

44. Fontenot J D, Rasmussen J P, Williams L M, Dooley J L, Farr A G, Rudensky A Y. Regulatory T cell lineage specification by the forkhead transcription factor foxp3. *Immunity* 2005; 22:329-341.

45. Bettini M L, Pan F, Bettini M, Finkelstein D, Rehg J E, Floess S, Bell B D, Ziegler S F, Huehn J, Pardoll D M, Vignali D A. Loss of epigenetic modification driven by the Foxp3 transcription factor leads to regulatory T cell insufficiency. *Immunity* 2012; 36:717-730.

46. Kehrmann J, Tatura R, Zeschnigk M, Probst-Kepper M, Geffers R, Steinmann J, Buer J. Impact of 5-aza-2'-deoxycytidine and epigallocatechin-3-gallate for induction of human regulatory T cells. Immunology [serial online] 2014 January [cited 2014 Feb. 3]; Available from: http://onlinelibrary.wiley.com/doi/10.1111/imm 12261/abstract 47. Ishii M, Wen H, Corsa C A S, Liu T, Coelho A L, Allen R M, Carson 4th W F, Cavassani K A, Li X, Lukacs N W, Hogaboam C M, Dou Y, Kunkel S L. Epigenetic regulation of the alternatively activated macrophage phenotype. *Blood* 2009; 114:3244-3254.

48. Miyao T, Floess S, Setoguchi R, Luche H, Fehling H J, Waldmann H, Huehn J, Hori S. Plasticity of Foxp3(+) T cells reflects promiscuous Foxp3 expression in conventional T cells but not reprogramming of regulatory T cells. *Immunity* 2012; 36:262-275.

49. Komatsu N, Okamoto K, Sawa S, Nakashima T, Oh-hora M, Kodama T, Tanaka S, Bluestone J A, Takayanagi H. Pathogenic conversion of Foxp3+ T cells into TH17 cells in autoimmune arthritis. *Nat Med* 2013; 20:62-68.

50. Bailey-Bucktrout S L, Martinez-Llordella M, Zhou X, Anthony B, Rosenthal W, Luche H, Fehling H J, Bluestone J A. Self-antigen-driven activation induces instability of regulatory T cells during an inflammatory autoimmune response. *Immunity* 2013; 39:949-962.

51. Obata Y, Furusawa Y, Endo T A, Sharif J, Takahashi D, Atarashi K, Nakayama M, Onawa S, Fujimura Y, Takahashi M, Ikawa T, Otsubo T, Kawamura Y I, Dohi T, Tajima S, Masumoto H, Ohara O, Honda K, Hori S, Ohno H, Koseki H, Hase K. The epigenetic regulator Uhrf1 facilitates the proliferation and maturation of colonic regulatory T cells. *Nat Immunol* 2014; 15:571-579.

52. Wang L, Liu Y, Beier U H, Han R, Bhatti T R, Akimova T, Hancock W W. Foxp3+ T-regulatory cells require DNA methyltransferase 1 expression to prevent development of lethal autoimmunity. *Blood* 2013; 121:3631-3639.

53. Thangavel J, Malik A B, Elias H K, Rajasingh S, Simpson A D, Sundivakkam P K, Vogel S M, Xuan Y-T, Dawn B, Rajasingh J. Combinatorial therapy with acety- 54. Ventilation with lower tidal volumes as compared with traditional tidal volumes for acute lung injury and the acute respiratory distress syndrome. The Acute Respiratory Distress Syndrome Network. *The New England journal of medicine* 342: 1301-1308, 2000.
55. Aggarwal N R, D'Alessio F R, Tsushima K, Files D C, Damarla M, Sidhaye V K, Fraig M M, Polotsky V Y, and King L S. Moderate oxygen augments lipopolysaccharide-induced lung injury in mice. *Am J Physiol Lung Cell Mol Physiol* 298: L371-381.
56. Aggarwal N R, King L S, and D'Alessio F R. Diverse macrophage populations mediate acute lung inflammation and resolution. *Am J Physiol Lung Cell Mol Physiol* 306: L709-725, 2014.
57. Aggarwal N R, Tsushima K, Eto Y, Tripathi A, Mandke P, Mock J R, Garibaldi B T, Singer B D, Sidhaye V K, Horton M R, King L S, and D'Alessio F R Immunological priming requires regulatory T cells and IL-10-producing macrophages to accelerate resolution from severe lung inflammation. *J Immunol* 192: 4453-4464, 2014.
58. Bouros D, Alexandrakis M G, Antoniou K M, Agouridakis P, Pneumatikos I, Anevlavis S, Pataka A, Patlakas G, Karkavitsas N, and Kyriakou D. The clinical significance of serum and bronchoalveolar lavage inflammatory cytokines in patients at risk for Acute Respiratory Distress Syndrome. *BMC pulmonary medicine* 4: 6, 2004.
59. D'Alessio F R, Tsushima K, Aggarwal N R, West E E, Willett M H, Britos M F, Pipeling M R, Brower R G, Tuder R M, McDyer J F, and King L S. CD4+CD25+ Foxp3+ Tregs resolve experimental lung injury in mice and are present in humans with acute lung injury. *J Clin Invest* 119: 2898-2913, 2009.
60. El Kasmi K C, Qualls J E, Pesce J T, Smith A M, Thompson R W, Henao-Tamayo M, Basaraba R J, Konig T, Schleicher U, Koo M S, Kaplan G, Fitzgerald K A, Tuomanen E I, Orme I M, Kanneganti T D, Bogdan C, Wynn T A, and Murray P J. Toll-like receptor-induced arginase 1 in macrophages thwarts effective immunity against intracellular pathogens. *Nat Immunol* 9: 1399-1406, 2008.
61. Fadok V A, Bratton D L, Konowal A, Freed P W, Westcott J Y, and Henson P M. Macrophages that have ingested apoptotic cells in vitro inhibit proinflammatory cytokine production through autocrine/paracrine mechanisms involving TGF-beta, PGE2, and PAF. *J Clin Invest* 101: 890-898, 1998.
62. Fallica J, Das S, Horton M, and Mitzner W. Application of carbon monoxide diffusing capacity in the mouse lung. *J Appl Physiol* (1985) 110: 1455-1459, 2011.
63. Fan E, Dowdy D W, Colantuoni E, Mendez-Tellez P A, Sevransky J E, Shanholtz C, Himmelfarb C R, Desai S V, Ciesla N, Herridge M S, Pronovost P J, and Needham D M. Physical complications in acute lung injury survivors: a two-year longitudinal prospective study. *Crit Care Med* 42: 849-859, 2014.
64. Fernandez-Boyanapalli R F, Frasch S C, McPhillips K, Vandivier R W, Harry B L, Riches D W, Henson P M, and Bratton D L. Impaired apoptotic cell clearance in CGD due to altered macrophage programming is reversed by phosphatidylserine-dependent production of IL-4. *Blood* 113: 2047-2055, 2009.
65. Finkelman F D, Madden K B, Morris S C, Holmes J M, Boiani N, Katona I M, and Maliszewski C R. Anti-cytokine antibodies as carrier proteins. Prolongation of in vivo effects of exogenous cytokines by injection of cytokine-anti-cytokine antibody complexes. *J Immunol* 151: 1235-1244, 1993.
66. Fleming B D, Chandrasekaran P, Dillon L A, Dalby E, Suresh R, Sarkar A, El-Sayed N M, and Mosser D M. The generation of macrophages with anti-inflammatory activity in the absence of STAT6 signaling. *Journal of leukocyte biology* 2015.
67. Garibaldi B T, D'Alessio F R, Mock J R, Files D C, Chau E, Eto Y, Drummond M B, Aggarwal N R, Sidhaye V, and King L S. Regulatory T cells reduce acute lung injury fibroproliferation by decreasing fibrocyte recruitment. *Am J Respir Cell Mol Biol* 48: 35-43, 2012.
68. Gordon S, and Martinez F O. Alternative activation of macrophages: mechanism and functions. *Immunity* 32: 593-604, 2010.
69. Gordon S, and Taylor P R. Monocyte and macrophage heterogeneity. *Nat Rev Immunol* 5: 953-964, 2005.
70. Guerin C, Reignier J, Richard J C, Beuret P, Gacouin A, Boulain T, Mercier E, Badet M, Mercat A, Baudin O, Clavel M, Chatellier D, Jaber S, Rosselli S, Mancebo J, Sirodot M, Hilbert G, Bengler C, Richecoeur J, Gainnier M, Bayle F, Bourdin G, Leray V, Girard R, Baboi L, Ayzac L, and Group P S. Prone positioning in severe acute respiratory distress syndrome. *N Engl J Med* 368: 2159-2168, 2013.
71. Halbower A C, Mason R J, Abman S H, and Tuder R M. Agarose infiltration improves morphology of cryostat sections of lung. *Lab Invest* 71: 149-153, 1994.
72. Heller N M, Qi X, Junttila I S, Shirey K A, Vogel S N, Paul W E, and Keegan A D. Type I IL-4Rs selectively activate IRS-2 to induce target gene expression in macrophages. *Sci Signal* 1: ra17, 2008.
73. Herold S, Mayer K, and Lohmeyer J. Acute lung injury: how macrophages orchestrate resolution of inflammation and tissue repair. *Front Immunol* 2: 65, 2011.
74. Huaux F, Liu T, McGarry B, Ullenbruch M, and Phan S H. Dual roles of IL-4 in lung injury and fibrosis. *J Immunol* 170: 2083-2092, 2003.
75. Lawrence T, and Natoli G. Transcriptional regulation of macrophage polarization: enabling diversity with identity. *Nat Rev Immunol* 11: 750-761, 2011.
76. Lazarski C A, Ford J, Katzman S D, Rosenberg A F, and Fowell D J. IL-4 attenuates Th1-associated chemokine expression and Th1 trafficking to inflamed tissues and limits pathogen clearance. *PLoS One* 8: e71949, 2013.
77. Lee Y J, Holzapfel K L, Zhu J, Jameson S C, and Hogquist K A. Steady-state production of IL-4 modulates immunity in mouse strains and is determined by lineage diversity of iNKT cells. *Nat Immunol* 14: 1146-1154, 2013.
78. Levitt J E, Bedi H, Calfee C S, Gould M K, and Matthay M A. Identification of early acute lung injury at initial evaluation in an acute care setting prior to the onset of respiratory failure. *Chest* 135: 936-943, 2009.
79. Levy B D, and Serhan C N. Resolution of acute inflammation in the lung. *Annual review of physiology* 76: 467-492, 2014.
80. Li G, Malinchoc M, Cartin-Ceba R, Venkata C V, Kor D J, Peters S G, Hubmayr R D, and Gajic O. Eight-year trend of acute respiratory distress syndrome: a population-based study in Olmsted County, Minnesota. *Am J Respir Crit Care Med* 183: 59-66, 2011.

81. Mantovani A, Biswas S K, Galdiero M R, Sica A, and Locati M. Macrophage plasticity and polarization in tissue repair and remodelling. *J Pathol.* January; 229(2): 176-85, 2013.
82. Matthay M A, Ware L B, and Zimmerman G A. The acute respiratory distress syndrome. *J Clin Invest* 122: 2731-2740, 2012.
83. Matute-Bello G, Frevert C W, and Martin T R. Animal models of acute lung injury. *Am J Physiol Lung Cell Mol Physiol* 295: L379-399, 2008.
84. Meduri G U, Headley S, Kohler G, Stentz F, Tolley E, Umberger R, and Leeper K. Persistent elevation of inflammatory cytokines predicts a poor outcome in ARDS. Plasma IL-1 beta and IL-6 levels are consistent and efficient predictors of outcome over time. *Chest* 107: 1062-1073, 1995.
85. Melgert B N, ten Hacken N H, Rutgers B, Timens W, Postma D S, and Hylkema M N. More alternative activation of macrophages in lungs of asthmatic patients. *J Allergy Clin Immunol* 127: 831-833, 2011.
86. Nair M G, Du Y, Perrigoue J G, Zaph C, Taylor J J, Goldschmidt M, Swain G P, Yancopoulos G D, Valenzuela D M, Murphy A, Karow M, Stevens S, Pearce E J, and Artis D. Alternatively activated macrophage-derived RELM-{alpha} is a negative regulator of type 2 inflammation in the lung. *The Journal of experimental medicine* 206: 937-952, 2009.
87. Pace L, Rizzo S, Palombi C, Brombacher F, and Doria G. Cutting edge: IL-4-induced protection of CD4+CD25− Th cells from CD4+CD25+ regulatory T cell-mediated suppression. *J Immunol* 176: 3900-3904, 2006.
88. Papazian L, Forel J M, Gacouin A, Penot-Ragon C, Perrin G, Loundou A, Jaber S, Arnal J M, Perez D, Seghboyan J M, Constantin J M, Courant P, Lefrant J Y, Guerin C, Prat G, Morange S, Roch A, and Investigators AS. Neuromuscular blockers in early acute respiratory distress syndrome. *N Engl J Med* 363: 1107-1116, 2010.
89. Pechkovsky D V, Prasse A, Kollert F, Engel K M, Dentler J, Luttmann W, Friedrich K, Muller-Quernheim J, and Zissel G. Alternatively activated alveolar macrophages in pulmonary fibrosis-mediator production and intracellular signal transduction. *Clinical immunology* 137: 89-101, 2010.
90. Pesce J T, Ramalingam T R, Mentink-Kane M M, Wilson M S, El Kasmi K C, Smith A M, Thompson R W, Cheever A W, Murray P J, and Wynn T A. Arginase-1-expressing macrophages suppress Th2 cytokine-driven inflammation and fibrosis. *PLoS Pathog* 5: e1000371, 2009.
91. Pesce J T, Ramalingam T R, Wilson M S, Mentink-Kane M M, Thompson R W, Cheever A W, Urban J F, Jr., and Wynn T A. Retnla (relmalpha/fizz1) suppresses helminth-induced Th2-type immunity. *PLoS Pathog* 5: e1000393, 2009.
92. Qualls J E, Neale G, Smith A M, Koo M S, DeFreitas A A, Zhang H, Kaplan G, Watowich S S, and Murray P J. Arginine usage in mycobacteria-infected macrophages depends on autocrine-paracrine cytokine signaling. *Science signaling* 3: ra62, 2010.
93. Rosseau S, Hammerl P, Maus U, Walmrath H D, Schutte H, Grimminger F, Seeger W, and Lohmeyer J. Phenotypic characterization of alveolar monocyte recruitment in acute respiratory distress syndrome. *Am J Physiol Lung Cell Mol Physiol* 279: L25-35, 2000.
94. Rubenfeld G D, Caldwell E, Peabody E, Weaver J, Martin D P, Neff M, Stern E J, and Hudson L D. Incidence and outcomes of acute lung injury. *The New England journal of medicine* 353: 1685-1693, 2005.
95. Sica A, and Mantovani A. Macrophage plasticity and polarization: in vivo veritas. *J Clin Invest* 122: 787-795.
96. Sindrilaru A, Peters T, Wieschalka S, Baican C, Baican A, Peter H, Hainzl A, Schatz S, Qi Y, Schlecht A, Weiss J M, Wlaschek M, Sunderkotter C, and Scharffetter-Kochanek K. An unrestrained proinflammatory M1 macrophage population induced by iron impairs wound healing in humans and mice. *J Clin Invest* 121: 985-997, 2011.
97. Singer B D, Mock J R, Aggarwal N R, Garibaldi B T, Sidhaye V K, Florez M A, Chau E, Gibbs K W, Mandke P, Tripathi A, Yegnasubramanian S, King L S, and D'Alessio F R. Regulatory T cell DNA methyltransferase inhibition accelerates resolution of lung inflammation. *Am J Respir Cell Mol Biol* 52: 641-652, 2015.
98. Steinberg K P, Milberg J A, Martin T R, Maunder R J, Cockrill B A, and Hudson L D. Evolution of bronchoalveolar cell populations in the adult respiratory distress syndrome. *Am J Respir Crit Care Med* 150: 113-122, 1994.
99. Taams L S, van Amelsfort J M, Tiemessen M M, Jacobs K M, de Jong E C, Akbar A N, Bijlsma J W, and Lafeber F P. Modulation of monocyte/macrophage function by human CD4+CD25+ regulatory T cells. *Human immunology* 66: 222-230, 2005.
100. Thepen T, Van Rooijen N, and Kraal G. Alveolar macrophage elimination in vivo is associated with an increase in pulmonary immune response in mice. *J Exp Med* 170: 499-509, 1989.
101. Tiemessen M M, Jagger A L, Evans H G, van Herwijnen M J, John S, and Taams L S. CD4+CD25+Foxp3+ regulatory T cells induce alternative activation of human monocytes/macrophages. *Proc Natl Acad Sci USA* 104: 19446-19451, 2007.
102. Ware L B, and Matthay M A. The Acute Respiratory Distress Syndrome. *N Engl J Med* 342: 1334-1349, 2000.
103. Wynn T A. IL-13 effector functions. *Annual review of immunology* 21: 425-456, 2003.
104. Wynn T A, and Cheever A W. Cytokine regulation of granuloma formation in schistosomiasis. *Curr Opin Immunol* 7: 505-511, 1995.
105. Zaynagetdinov R, Sherrill T P, Kendall P L, Segal B H, Weller K P, Tighe R M, and Blackwell T S. Identification of Myeloid Cell Subsets in Murine Lungs Using Flow Cytometry. *Am J Respir Cell Mol Biol* 2013.

The invention is further described for illustrative purposes, in the following specific, non-limiting Examples.

EXAMPLES

Example 1

Methods

Lung injury and Therapy: 5-aza-2'-deoxycytidine (DAC) was administered commencing 24 hours after intratracheal lipopolysaccharide-induced lung injury to wild type, lymphocyte-deficient recombinase activating gene-1-null (Rag-$1^{-/-}$), and to Treg-depleted (diphtheria toxin-treated Foxp3DTR) mice. Lung injury phenotype during resolution was then measured. Furthermore, the specific effect of Treg DNA methyltransferase inhibition by adoptive transfer of ex vivo-treated Tregs to Treg-depleted mice following lung injury was assessed.

Mice. C57BL/6 wild type (WT) and Rag-$1^{-/-}$ mice were purchased from Jackson Laboratory (Bar Harbor, Me.). Foxp3DTR (B6.129(Cg)-Foxp3tm3Ayr/J) mice—which express a diphtheria toxin receptor-green fluorescent protein (DTR-GFP) fusion product from an internal ribosome entry site within the Foxp3 3' untranslated region (1)—were a gift from Alexander Rudensky, PhD (Sloan-Kettering Institute, New York, N.Y.). Animals were bred and housed in a pathogen-free facility. All animal protocols were approved by the Johns Hopkins Animal Care and Use Committee. Male mice aged 8-10 weeks were used.

Preparation of Mice. Intraperitoneal (i.p) ketamine (150 mg/kg) and acetylpromazine (2.5 mg/kg) were administered before tracheal exposure and intubation with a 20-gauge catheter. *Escherichia coli* O55:B5 lipopolysaccharide (LPS, 4 mg/kg; Sigma-Aldrich, St. Louis, Mo.) was injected into the trachea as an injurious stimulus; sterile water served as a sham for LPS. 4 mg/kg was found to be the LPS dose that caused approximately 50% mortality in Rag-1−/− mice using our current lot (109K4075). Beginning 24 hours after LPS or water administration, 5-aza-2'-deoxycytidine (DAC, 1 mg/kg; Sigma-Aldrich) or vehicle containing DMSO (0.438 mL/kg, Invitrogen, Carlsbad, Calif.) was administered in phosphate-buffered saline (PBS, 0.1 mL total volume) via daily i.p. injection. Diphtheria toxin (List Biologicals, Campbell, Calif.) was administered i.p. in PBS (0.1 mL) in the following doses on days relative to LPS injection: 50 mcg/kg on day −2 and 10 mcg/kg on alternate days beginning with day −1. For influenza experiments, 600 EID50 units of A/PR/8/34 H1N1 influenza virus (Charles River Laboratories, Wilmington, Mass.) in 30 μL PBS was administered via intratracheal (i.t.) injection (2). Vehicle or DAC was given as above on days 3 through 7 post-inoculation. Euthanasia was performed by inferior vena cava exsanguination at the described time points. Following euthanasia, bronchoalveolar lavage (BAL) fluid analysis and lung histology were performed as previously described (3).

Diphtheria toxin-treated WT mice were used as controls for certain of the experiments that used Foxp3DTR mice. Foxp3DTR mice expressed a normal Foxp3 protein and a diphtheria toxin receptor-green fluorescent protein fusion product (DTR-GFP). While mice expressing a Foxp3-GFP fusion protein (Foxp3gfp) had previously facilitated studies of Treg biology (44), these mice exhibited abnormal Treg epigenetic programming, due to the altered Foxp3 protein (45). Thus, for the current experiments, mice with a normal Foxp3 protein were selected, to ensure fidelity of epigenetic responses.

Bronchoalveolar lavage (BAL) fluid analysis. Two 0.7-mL PBS aliquots were instilled into the right lung via a 20-gauge catheter. Typical return was 0.9-1.1 mL. Total BAL cell counts were measured using trypan blue (Invitrogen) exclusion on a hemocytometer following erythrocyte lysis with ACK lysis buffer (Invitrogen). Differential cell counts were performed by cytospin preparation (Cytospin 3; Shandon Scientific, Rockville, Md.) and Diff-Quik staining (Baxter Diagnostics, Deerfield, Ill.), counting 300 cells per sample. BAL fluid total protein concentration was measured using Lowry's method (3). BAL fluid active TGF-β concentration was measured by ELISA (R&D Systems, Minneapolis, Minn.).

Histology. Left lungs were excised and prepared for histologic analysis (4). Briefly, lungs were inflated to 25 cm H2O with 1% low-melting agarose (Invitrogen), fixed in formalin, embedded in paraffin, sectioned, and stained with hematoxylin and eosin. Images were captured at 20× and 200× magnification using a Nikon inverted microscope with Image-Pro Discovery software (Media Cybernetics, Rockville, Md.).

Flow Cytometry. Following euthanasia and flushing the pulmonary circulation with 1 mL PBS, right lungs were excised, minced, and incubated in PBS containing 5 mg/mL collagenase I (Worthington Biochemical Corporation, Lakewood, N.J.) and 1 mg/mL DNase (Sigma-Aldrich) with 3% bovine serum albumin (BSA, Sigma-Aldrich) at 37° C. for 30 minutes. Suspensions were then aspirated eight times through an 18-gauge needle before being filtered through a 70-μm nylon strainer (BD Biosciences, San Jose, Calif.) to remove cell clumps. Erythrocytes were removed using ACK lysis buffer before a second 70-μm nylon strainer filtration and re-suspension in PBS containing 0.5% BSA. Spleen was mashed through a 40-μm nylon strainer, treated with ACK lysis buffer, and re-suspended in 0.5% BSA.

Cells were prepared for FACS analysis (4) with fluorochrome-conjugated antibodies purchased from BD Pharmingen, BioLegend (San Diego, Calif.), and eBioscience (San Diego, Calif.). Surface stains included PE-Cy7-conjugated anti-CD39, PE-CF594-conjugated anti-CD8 (to confirm exclusion of CD8+ cells from analysis), APC-Cy7-conjugated anti-CD25, Alexa Fluor 700-conjugated anti-CD4, and V500-conjugated anti-CD44. Intracellular stains included PE-, FITC-, or PerCP eFluor 710-conjugated anti-Ki-67, APC-conjugated anti-Foxp3, and BV421-conjugated anti-CTLA-4. Live-dead discrimination was performed with Fixable UV-excitable Blue Dead Cell Stain (Invitrogen). Compensation was completed with UltraComp eBeads (eBioscience). Acquisition was performed using a FACSAria instrument with FACSDiva software (BD) and FlowJo version 7.6.5 (Tree Star, Inc., Ashland, Oreg.) for analysis. FIG. 9 shows the Treg gating strategy. Mean fluorescence intensity was calculated as the geometric mean of the positive population fluorescence. Lung cell number was estimated by flow cytometry and confirmed with a hemocytometer using trypan blue exclusion.

DNA methylation. Tregs cultured with vehicle or 100 nM DAC as above were harvested after 48 hours. DNA was isolated using an AllPrep DNA/RNA Micro kit (Qiagen, Valencia, Calif.) according to the manufacturer's recommendations. Global DNA methylation was measured on 100 ng of DNA using an Imprint Methylated DNA Quantification kit (Sigma-Aldrich) according to the manufacturer's recommendations and compared to a methylated DNA control.

Lymphocyte Culture. Splenic CD4+ CD25+ cells (>85% Foxp3+) and CD4+ CD25− cells were isolated using magnetic bead separation (Miltenyi Biotec, Auburn, Calif.) as previously described (3). Foxp3 positivity using this method was always >85%. Tregs were then plated in 96-well plates at $2 \times 10^5$ cells per well containing 200 μL media (5), 1 μg/mL plate-bound anti-CD3 and soluble anti-CD28 (eBioscience) to provide T cell stimulation, and 40 IU/mL recombinant murine IL-2 (Peprotech, Rocky Hill, N.J.) as a survival factor. Cells were then plated in media (28) with plate-bound anti-CD3, soluble anti-CD28 (eBioscience), and recombinant murine IL-2 (Peprotech, Rocky Hill, N.J.). Cells were incubated for 48 hours with vehicle or 10 or 100 nM DAC before FACS analysis, DNA methylation measurement, use in suppression assays, or adoptive transfer.

Lymphocyte Suppression Assay. Tregs cultured with 100 nM DAC or vehicle as above were incubated with anti-CD3/CD28-coated latex microbeads and CellTrace Violet-pulsed (Invitrogen) CD4+ CD25− effector T cells (Teff) purified by Miltenyi magnetic bead separation (28). Teff did not receive DAC or vehicle treatment. Treg:Teff ratios ranged from 1:8-1:2 with $1 \times 10^5$ Teff per well. After 72 hours, effector T cell proliferation was assayed by FACS analysis.

Adoptive Transfer. Following 48 hours in culture with 100 nM DAC or vehicle as above, $2 \times 10^5$ live Tregs were administered via retro-orbital injection to Treg-depleted Foxp3DTR mice one hour after intratracheal LPS. These mice did not receive systemic DAC or vehicle administration.

Statistical Analysis. Groups of 5-9 mice were used for all experiments and repeated (29). In vitro experiments were performed in triplicate and repeated at least three times. Values are reported as mean±standard error (SEM). Differences between groups were compared using two-tailed Mann-Whitney U tests or Student's t-tests with Holm-Sidak correction for multiple comparisons (mean fluorescence intensity data). Ki-67 positivity was compared using a chi-square test with Yates' correction. Multiple group comparisons were performed using one-way ANOVA or one-way ANOVA on ranks. Mortality differences were analyzed with the Mantel-Cox test. Significance was determined at alpha values less than 0.05.

Example 2

Overview: DAC Accelerated Recovery from LPS-Induced Acute Lung Injury

To test how dynamic DNA demethylation affects lung injury resolution, the DNA methyltransferase inhibitor 5-aza-2'-deoxycytidine (DAC) was administered to wild type mice beginning 24 hours after intratracheal lipopolysaccharide-induced lung injury. Mice that received DAC had similar early lung inflammation compared to vehicle-treated mice but exhibited accelerated resolution of their injury. Lung Tregs from DAC-treated wild type mice increased in frequency and displayed an enhanced activation state, suppressive phenotype, and proliferative capacity. Lymphocyte-deficient recombinase activating gene-1-null (Rag-1$^{-/-}$) mice and Treg depleted (diphtheria toxin-treated Foxp3DTR) mice did not resolve their injury in response to DAC, confirming the criticality of both Rag-1 and Treg to the DAC therapy. Adoptive transfer of only 200,000 DAC-treated, but not vehicle-treated, exogenous Tregs rescued Treg-deficient mice from ongoing lung inflammation, thereby identifying an attractive additional form of therapy (ex vivo cell-based) for lung injury. These results indicated that DNA methyltransferase inhibition markedly enhanced Treg function to accelerate lung injury repair in a mouse model. Epigenetic pathways were thereby identified as novel manipulable targets for the treatment of ARDS and other acute inflammatory disorders.

Example 3

DAC Therapy Increased Lung Regulatory T Cell Frequency

Figure 1:
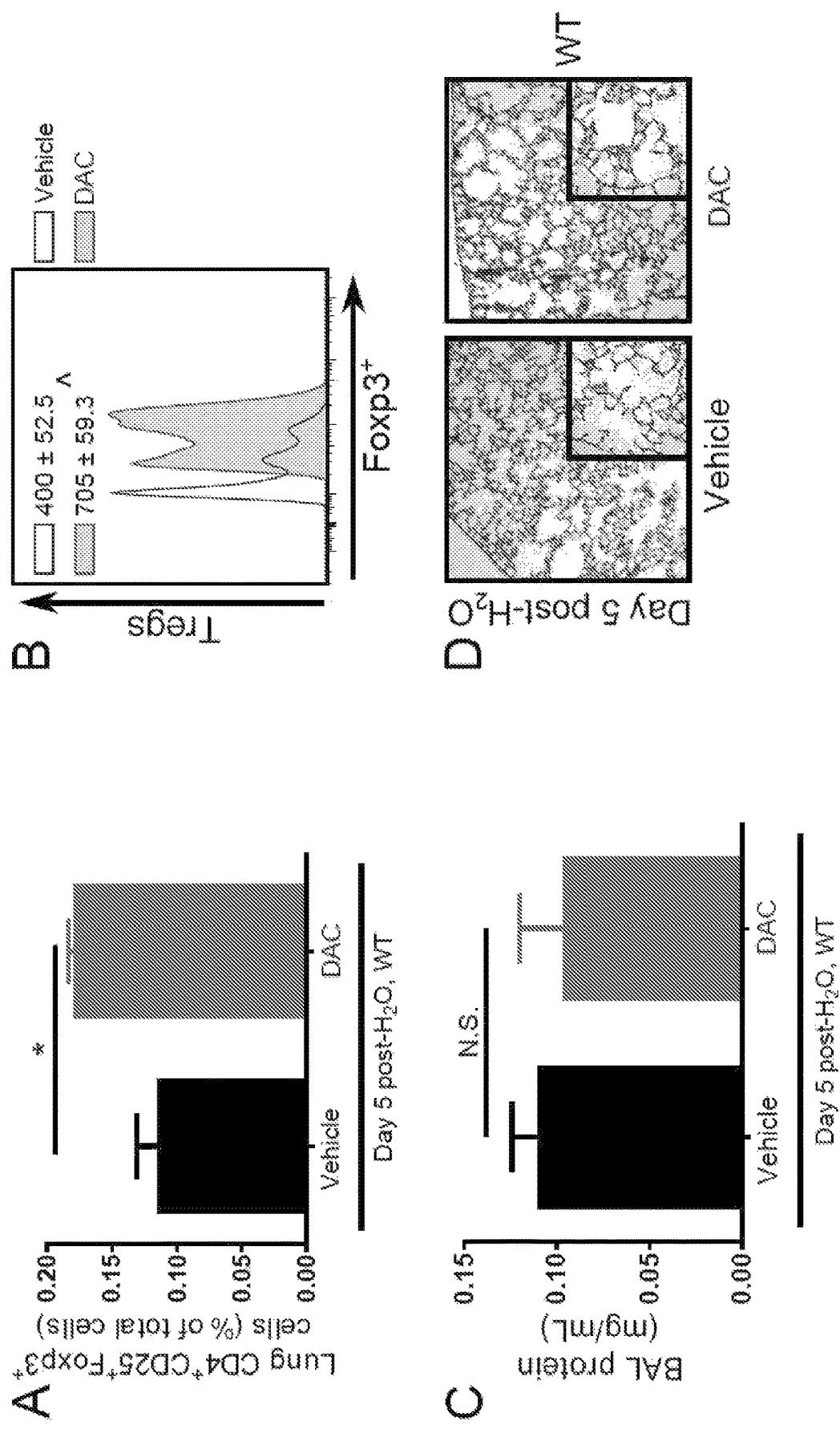
FIGS. 1A to 1D show that DAC increased lung Treg frequency and Foxp3 expression under sham injury conditions.

The impact of DAC administration upon Treg frequency and Foxp3 expression was assessed in wild type (WT) mice under non-injurious circumstances, with the goal of ascertaining whether DAC treatment could expand lung Treg frequency and increase Foxp3 expression. As a sham condition for lung injury, WT mice received an intratracheal (i.t.) sterile water dose on day 0. They then received daily intraperitoneal (i.p.) DAC or vehicle on days 1 through 4. On day 5 post-water, increased lung Treg frequency was observed in DAC-treated mice, as compared to vehicle-treated mice (FIG. 1A and FIG. 13A). Lung Treg Foxp3 expression also increased in the DAC treatment group (FIG. 1B and FIG. 13B), as determined by FACS analysis using fluorochrome-conjugated antibodies. To ensure that neither the drug nor vehicle contributed to lung injury, bronchoalveolar lavage (BAL) was performed to assess total protein concentration (a lung permeability marker), and histological examination was also performed. BAL protein was low overall following i.t. water in both groups (FIG. 1C). Lung histology (FIG. 1D) was normal after four days of DAC or vehicle treatment. Neither group lost weight or experienced mortality (data not shown). Thus, DAC increased both lung Treg frequency and Foxp3 expression at a non-toxic dose under non-injurious circumstances. Collectively, DAC increased lung Treg number and Foxp3 expression in a dose that did not cause pulmonary or overt systemic toxicity.

Example 4

DAC Accelerated Resolution of Lung Injury

Figure 2:
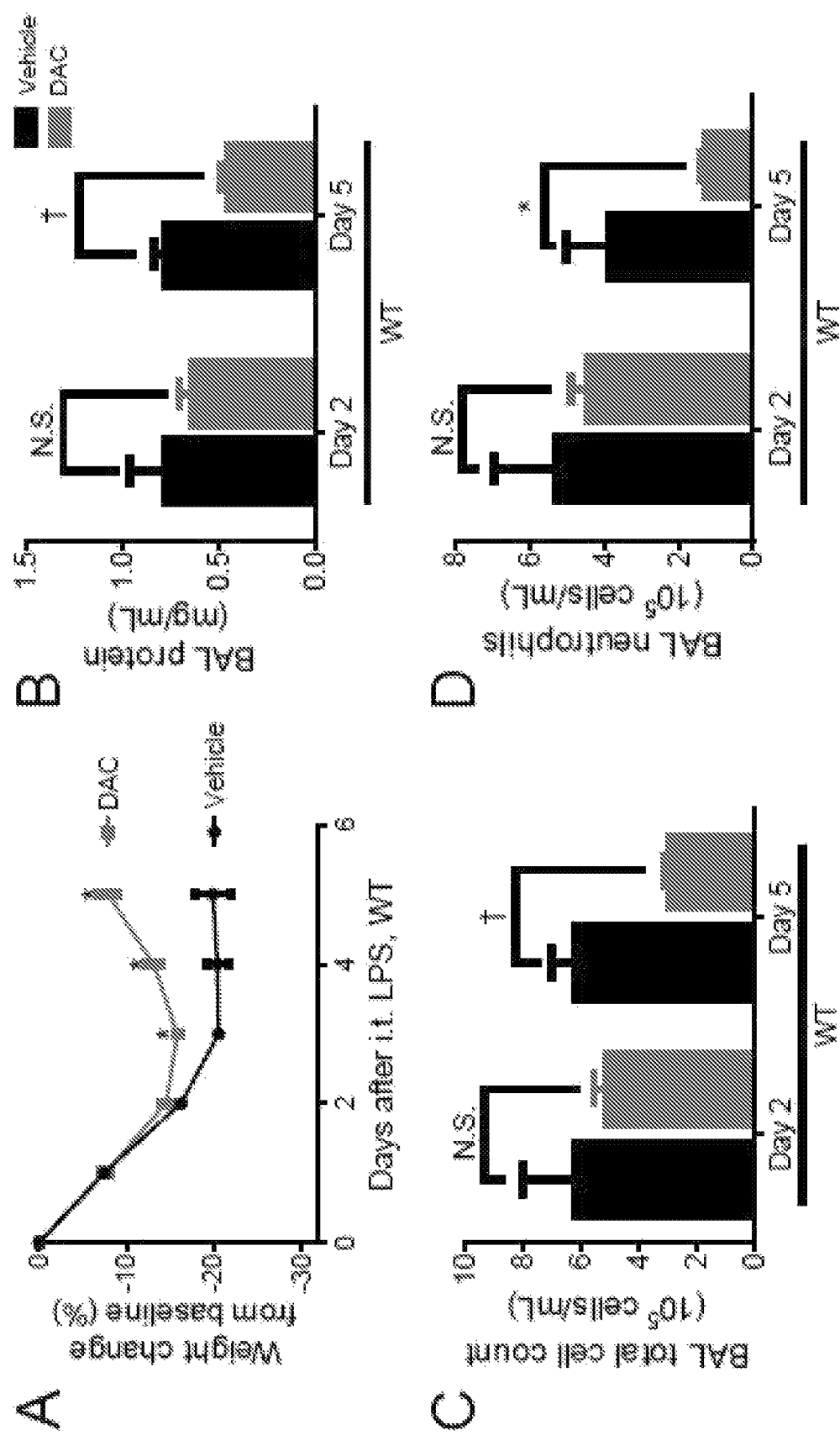
FIGS. 2A to 2E demonstrate that DAC treatment promoted resolution of lung injury in WT mice.

Having identified DAC to promote Treg frequency and Foxp3 expression in healthy subjects, the impact of DAC upon subjects with lung injury was then examined Specifically, in view of DAC-induced expansion of Treg frequency and the role that Treg cells were previously identified to play in recovery from acute lung inflammation, the ability of DAC to enhance resolution of severe i.t. LPS-induced lung injury was examined In such experiments, WT mice received DAC or vehicle starting 24 hours after injury (performed via i.t. LPS administration). Mice in the vehicle group exhibited sustained weight loss, consistent with lasting injury, whereas DAC-treated mice steadily regained weight after initial injury (FIG. 2A). Mortality was ultimately 28.5% in the vehicle group, whereas none of the DAC group mice died during the course of the experiment (P=0.029, Mantel-Cox test). Vehicle- and DAC-treated mice exhibited similar early injury as measured by BAL protein, cell count, neutrophil count, and lung histology, performed two days after injury (FIGS. 2B-E). At day 5 post-LPS, DAC-treated, but not vehicle-treated, mice displayed a resolving phenotype, with injury parameters returning toward normal (FIGS. 2B-E). Thus, DAC adminstration did not affect early injury but enhanced resolution of severe i.t. LPS-induced lung injury in WT mice.

Example 5

DAC Treatment Increased Lung Treg Frequency and Suppressed Injury Phenotypes Post-Injury Tregs were previously identified to resolve lung injury following LPS administration (3). The cellular basis for the above-identified DAC-induced recovery from lung injury was then examined via assessment of the effect of systemic DAC treatment upon Treg cells post-injury. When Treg cells were examined, lung Treg frequency was observed to have increased more than two-fold at day 5 post-injury in response to systemic DAC treatment (FIG. 3A), with significant results observed for fixed numbers of cells taken from the right lung (FIG. 3A, left panel), for such cells as a percentage of total cells (FIG. 3A, middle panel) and for such cells as a percentage of CD4$^+$ cells (FIG. 3A, right panel). However, at two days post-injury (following one DAC dose) no effect was observed on lung Treg frequency or phenotype (data not shown). Foxp3 expression, the master regulator of Treg development and function, also increased in lung Tregs isolated from DAC-treated mice five days post-LPS (FIG. 3B). FIG. 3C shows the Treg phenotypic response to DAC five days after injury. CD44, a Treg activation marker (30), also increased (FIG. 3C, left panel), as did CD39, an ecto-enzyme that catalyzes ATP hydrolysis and serves as an important Treg suppressive mediator (FIG. 3C, middle panel; 31). CTLA-4, a powerful negative signal to other immune cells (32), was modestly yet significantly increased (FIG. 3C, right panel). There was no significant change in CD25 expression in response to DAC (data not shown). Consistent with an overall increase in Treg frequency, the expression of Ki-67 (a cell proliferation marker) increased in lung Tregs isolated from DAC-treated mice (FIG. 3D). DAC treatment did not impact lung CD4+ Foxp3− cell frequency or phenotype (FIGS. 10A to 10C). Splenic Treg frequency paralleled the lung findings (FIG. 11). Thus, the frequency, activation state, suppressive phenotype, and proliferative capacity of lung Tregs following DNMT inhibition post-injury was augmented.

Example 6

The Therapeutic Effect of DAC Required Lymphocytes

DNMT inhibition exerts profound effects on lymphocyte phenotype and function (14), but can affect virtually any cell type. To examine if lymphocytes were involved in the therapeutic (pro-resolution) effect of DNMT inhibition observed in WT mice, DAC or vehicle was also administered on days 1 through 4 to LPS-injured lymphocyte-deficient (Rag-1$^{-/-}$) mice. Five days post-injury, a time point at which DAC-treated WT mice exhibited a resolving phenotype, Rag-1$^{-/-}$ mice displayed persistent injury and could not be rescued by DAC. The Rag-1$^{-/-}$ mice also experienced sustained weight loss, elevated BAL protein, cell count, neutrophil count, and severe histological lung inflammation five days post-injury (FIGS. 4A-E). Mortality was 50% in the vehicle group and 44% in the DAC group (P=0.7, Mantel-Cox test). Thus, the non-resolving phenotype in Rag-1$^{-/-}$ mice demonstrated that lymphocytes were required for DAC to exert its pro-resolution action.

Example 7

Tregs were Required for DAC-Enhanced Resolution

To confirm whether DAC-induced resolution of acute lung injury was mediated by Treg cells (noting that DNA hypomethylation was previously identified as a defining Treg characteristic (17)), Treg cells were specifically depleted from injured mice, and the effects were examined. To deplete Tregs, Foxp3DTR mice (in such mice, diphtheria toxin (DT) administration results in ablation of Treg cells in thymus, lymph nodes, and spleen 2 days after injection, with cell numbers rebounding 10-15 days post-injection) were administered diphtheria toxin beginning two days prior to LPS injury and then every other day thereafter. Similar to the Rag-1$^{-/-}$ results described above, and in contrast to WT mice, DAC treatment in Treg-depleted Foxp3DTR mice did not accelerate lung injury resolution, as measured by weight, BAL protein, cell count, neutrophil count, and lung histology five days post-LPS (FIGS. 5A-E). Mortality was 33% in both groups. Lung Treg depletion in diphtheria toxin-treated Foxp3DTR mice was also confirmed, as compared to diphtheria toxin-treated LPS-injured WT mice 5 days post-injury (FIG. 12A). In a pattern similar to WT mice from FIG. 2 above, WT mice treated with diphtheria toxin experienced accelerated lung injury resolution in response to DAC (FIGS. 12B-12E). These data confirmed that Tregs were required for DAC to exert its therapeutic influence in resolving lung inflammation.

Example 8

DAC Increased Treg Foxp3 Expression and Suppressive Activity In Vitro

Having established the role of Treg cells in DAC-induced recovery from lung injury, it was examined whether such effects could be recapitulated in Treg cells in vitro. To determine the effects of DNMT inhibition on CD4+ T cells in vitro, either CD4+ CD25− cells (conventional T cells) or CD4+ CD25+ cells (Tregs, >85% Foxp3$^+$) were cultured with anti-CD3/CD28 antibodies and IL-2, with or without DAC treatment. DAC administration induced Foxp3 expression in conventional T cells and augmented Foxp3 expression in Tregs (FIG. 6A). When cultured with DAC, Tregs increased CD44 expression (FIG. 6B, first panel). In contrast to the in vivo findings, DAC did not augment Treg CD39 (FIG. 6B, second panel), and modestly increased CTLA-4 expression (FIG. 6C, third panel). A higher percentage of the DAC-treated Tregs expressed Ki-67 compared with vehicle treatment (FIG. 6C). After 48 hours in culture, the classical Treg suppressive activity in a mixed lymphocyte reaction was tested. DAC-treated Tregs suppressed effector T cell proliferation with greater potency than vehicle-treated Tregs (FIG. 6D). Effector T cells did not receive DAC or vehicle treatment. A significant decrease in the proportion of methylated DNA (relative to methylated control DNA) was also confirmed following 48 hours of 100 nM treatment with DAC, as compared to treatment with vehicle control (FIG. 6E). Collectively, DNMT inhibition in culture hypomethylated Tregs and recapitulated some features observed in injured mice (Foxp3 expression, activation, and proliferation) but not increased CD39 expression. Thus, DNMT inhibitor-treated Tregs had greater suppressive function in a mixed lymphocyte reaction.

Example 9

Adoptive Transfer of DAC-Treated Tregs Mediated Resolution

Because systemic DAC administration likely affects a myriad of cell types, ex vivo approaches to DAC treatment of Treg cells might also be attractive for use as a lung injury therapeutic. It was therefore examined how ex vivo DAC-treated Tregs specifically influenced lung injury resolution. Previous work had indicated that therapeutic adoptive transfer of less than 10$^6$ vehicle-treated Tregs provided an insufficient dose to effect robust resolution of LPS-induced acute lung injury (3). Thus, LPS-injured Treg-depleted Foxp3DTR mice were administered 2×10$^5$ WT splenic DAC- or vehicle-treated Tregs via retro-orbital injection one hour after i.t. LPS, to assess whether DAC treatment of Treg cells could reduce the number of Treg cells necessary for adoptive transfer to be effective. Initial injury was similar between the two groups. Seven days post-injury, mice that received vehicle-treated Tregs displayed unremitting lung inflammation characterized by sustained weight loss and elevations in BAL cell count, neutrophil count, and protein, as well as injured histology. In contrast, lung injury resolution occurred in mice that received DAC-treated Tregs (FIGS. 7A-E). Flow cytometry confirmed successful adoptive transfer and homing to the lung (FIG. 9 shows gating).

BAL active TGF-β was significantly increased in DAC-treated Tregs, as compared with vehicle-treated Treg recipients (FIG. 7F). Mortality was 25% in vehicle-treated Treg recipients and 14% in DAC-treated Treg recipients (P=0.6, Mantel-Cox test). Exogenous lung Tregs (Foxp3-APC+ GFP− ) were significantly elevated in DAC-treated Treg populations, when assessed in a fixed number of cells (FIG. 7G, left panel), as a percentage of total cell count (FIG. 7G, middle panel), or as a percentage of CD4$^+$ cells. Among exogenous Tregs, the DAC-treated phenotype resembled the profile observed with systemic DAC administration, with increases in Foxp3, CD44, CD39, CTLA-4, and Ki-67 expression (FIGS. 7H and 7I) and no difference in CD25 (data not shown). Thus, an otherwise sub-therapeutic dose of ex vivo DAC-treated Tregs facilitated lung injury resolution.

Example 10

DAC Treatment Increased Lung Treg Frequency and Suppressed Influenza-Induced Injury Phenotypes Post-Influenza Challenge in a Mouse Influenza Model Use of DAC as a therapeutic for Influenza-induced lung injury was also examined In addition to LPS-induced lung inflammation, wild type mice were inoculated via the intratracheal route with a laboratory strain of H1N1 influenza and administered DAC or vehicle on days 3 through 7 post-inoculation. At day 10 post-inoculation, DAC-treated mice exhibited a smaller magnitude of weight loss and decreased BAL protein, cell count, neutrophil count, and histologic injury, as compared to vehicle-treated mice (FIGS. 8A-8E). DAC-treated animals displayed an increase in lung Treg number and Foxp3 expression (FIGS. 8F and 8G). Rescue treatment with DAC exerted favorable effects on lung injury and Tregs in an infectious model of direct lung inflammation. As shown in FIGS. 8A to 8G significant, beneficial impact of DAC treatment was observed upon weight (FIG. 8A), BAL levels (FIGS. 8B to 8D) histological recovery from influenza (FIG. 8E), and Treg levels (FIGS. 8F and 8G) in mice that had received an influenza challenge, with such results assessed at ten days post-inflenza challenge. Thus, use of DNMT inhibitors in an influenza therapeutic capacity was confirmed.

While the above Examples primarily assessed lung Treg levels, it was further noted that DAC treatment significantly elevated spleen Treg levels, at either five days post-LPS challenge or at five days post-water treatment (FIG. 11).

Example 11

Methods for Investigating IL-4 Treatment

Lung injury and Therapy: Intratracheal (i.t.) lipopolysaccharide (LPS, 4-5 mg/kg mouse) was delivered to C57BL/6 (BL/6) WT mice, BALB/c WT mice, and Stat6$^{-/-}$ mice. Mice were treated with systemic rIL-4 complex (rIL-4 2.5 ug/dose+IL-4 antibody (Ab) 15 ug/dose on days 2, 3, +/−4 or sham) or IL-4 blocking Ab (150 ug/dose on days 1-5 or sham) In addition, Foxp3DTR mice were treated with i.t. LPS (3 mg/kg) along with systemic diptheria toxin (DT) on days −2, −1, +1, 3, 5 (relative to i.t. LPS on day 0) and finally with systemic rIL-4 complex on days 2 and 3 (vs. sham) All mice were harvested on day 6 after i.t. LPS for the endpoints described below.

IL-4 Complex Preparation and Antibody Injections. IL-4 was complexed to an anti-IL-4 antibody to prolong bioavailability, extending the half-life in mice from 0.5 to 24 hours (65). Each dose of IL-4 complex contained 2.5 µg of recombinant IL-4 cytokine (PeptroTech) and 15 µg of an anti-IL-4 antibody (BioXcell, clone 11B11) suspended in 150 µL of sterile PBS and was administered by i.p. injection on days 2-4 after i.t. LPS, or on days 2-3 after i.t. PAO1 vs. sham (150 µL PBS) unless stated otherwise. For blocking experiments, anti-IL-4 antibody (200 µg, BioXcell, clone 11B11) suspended in 150 µL of sterile PBS or sham (150 µL PBS) was delivered i.p. on days 1-5 after i.t. LPS.

Diphtheria Toxin and Clodronate Liposome Injections. Diphtheria toxin (List Biological Laboratories, Inc, Lot #15043A1) was diluted in PBS and administered via i.p. injection on days −2 (50 µg/kg mouse) and −1 (10 µg/kg) prior to i.t. LPS, and on days +1, +3, and +5 (10 µg/kg) following i.t. LPS as previously described (97). Clodronate liposomes (Cl$_2$MDP) or PBS liposomes (control) were prepared as previously described (100), followed by intravenous (i.v.) instillation after being diluted in 150 µL of PBS on days 0 and +3 relative to i.t. LPS exposure.

Animals. Male C57BL/6J and BALB/cJ wild type (WT) mice (8-10 weeks old) were purchased from Jackson Laboratories (Bar Harbor, Me.). Stat6-/- mice on a BALB/c background (gift of Dr. Alan Scott) and Foxp3DTR mice on a C57BL/6 background (gift of Dr. Alexander Y. Rudensky of Memorial Sloan-Kettering) were bred. All mice were housed at the Johns Hopkins University Asthma and Allergy Bldg, and experiments conducted under a protocol approved by the Johns Hopkins Animal Care and Use Committee.

Preparation of Mice. Animals were anesthetized and the trachea was intubated as previously described (D'Alessio et al. *J Clin Invest* 119: 2898-2913). *Escherichia coli* O55:B5 lipopolysaccharide (LPS, 4 mg/kg; Sigma-Aldrich, St. Louis, Mo.) or sterile water was injected into the trachea. Beginning 24 hours later, rIL-4 or vehicle was administered via daily intraperitoneal (i.p.) injection. Diphtheria toxin (List Biologicals, Campbell, Calif.) was administered i.p. in a dosing scheme. Following euthanasia, bronchoalveolar lavage (BAL) fluid analysis and lung histology were performed as previously described (D'Alessio et al. *J Clin Invest* 119: 2898-2913). Diphtheria toxin-treated WT mice were used as controls for certain of the experiments that used Foxp3DTR mice. Foxp3DTR mice expressed a normal Foxp3 protein and a diphtheria toxin receptor-green fluorescent protein fusion product (DTR-GFP).

Animal Injections and Harvest. Intratracheal (i.t.) injections were performed as before (59). Briefly, mice were anesthetized with intraperitoneal (i.p.) ketamine/acetylpromazine (100/2.5 µg/g) before exposure of the trachea. Lipopolysaccharide (LPS) (3-5 mg/kg mouse weight diluted in sterile water), *Pseudomonas aeruginosa* (PAO1) (2×10$^6$ CFUs, ATCC, in 50 µL PBS) or respective vehicle controls were instilled i.t. through a 20-gauge endotracheal catheter on experiment day 0. After 4, 5, or 6 days, groups of mice were anesthetized with i.p. ketamine/acetylpromazine and euthanized by exsanguination from the inferior vena cava. The lungs were perfused with 1 ml of phosphate-buffered saline (PBS), followed by bronchoalveolar lavage (BAL) of the right lung following each of two aliquots of 0.7 mL PBS without calcium that was instilled via a 20-gauge endotracheal catheter. The left lung was processed for histology, collagen, immunoblot, or mRNA. BAL samples were routinely cultured to assess for bacterial infection.

BAL Analysis. BAL was centrifuged at 700×g for 10 min at 4° C. The cell-free supernatants were stored at −80° C. until further analysis. The cell pellet was diluted in PBS, and total cell number was counted with a hemacytometer using trypan blue exclusion. Cell differentials (300 cells per sample) were counted on cytocentrifuge preparation with Diff-Quik stain (Baxter Diagnostics, McGaw Park, Ill.). Total protein was measured in the cell-free supernatant by the Lowry method (55). Albumin was quantified in the cell-free supernatant by ELISA (Bethyl Laboratories, Montgomery, Tex.).

Lung Histology—H&E. Lungs were inflated to a pressure of 25 cmH2O using 1% low melting agarose (Invitrogen, Carlsbad, Calif.) prior to sectioning and staining with hemotoxylin and eosin (71).

Assessment of Lung Collagen Content. On day 6 after i.t. LPS, left lungs were homogenized in 1 ml of Complete Lysis Buffer (Roche, Indianapolis) using an UltraTurrax tissue homogenizer (Janke and Kunkel, Wilmington, N.C.). Collagen was measured by Sircol Assay (BioColor, Carrickferguss, UK) according to the manufacturer's instructions as before (67).

Lung Function Measurements. On day 6 after i.t. LPS, diffusing capacity was assessed by calculating the diffusion factor for carbon monoxide (DFCO) using a published method (62). In short, the lungs were inflated with 0.8 ml of a gas mixture (~0.5% carbon monoxide (CO), 0.5% neon (Ne), and 99% room air). After a 9 second exposure, the gas mixture was withdrawn from the lungs and diluted to 2 ml with room air. After 15 seconds the recovered gas was injected into a Micro GC gas chromatograph (INFICON, Micro GC Model 3000A, East Syracuse, N.Y.) and the concentrations of Ne and CO were determined. The DFCO was defined as 1-(CO9/COC)/(Ne9/NeC), where COC and NeC represent the concentration of CO and Ne in the calibration gas and CO9 and Ne9 reflect the concentrations of CO and Ne after the 9-second breath hold. After DFCO measurements, mice were paralyzed by administration of 75 mg/kg succinylcholine and connected to a flexiVent™ system (Scireq, Montreal, QC, Canada). Mice were ventilated with 100% oxygen at a tidal volume of 10 ml/kg, a rate of 150 breaths per minute, and a positive end-expiratory pressure (PEEP) of 3 cmH2O. After 3 minutes of ventilation, the lungs were inflated to 30 cmH2O for 5 seconds, returned to normal ventilation for 1 minute, and single-compartment mechanics were measured with a 2.5-Hz sinusoidal oscillation (Snapshot-150) to obtain respiratory system dynamic compliance (Crs).

Whole Lung Homogenate RNA and Protein Isolation. On days 4 and 6 following LPS exposure, lung tissues were homogenized in Trizol Reagent (Life Technologies) and RNA and protein were extracted following phase-separation with chloroform. The aqueous phase was removed and total RNA was precipitated with 100% isopropyl alcohol, washed with 75% ethanol, and redissolved in DEPC-treated water. DNA was removed from the interphase/organic phase with 100% ethanol before protein was precipitated from the remaining phenol-ethanol supernatant by 100% isopropyl alcohol. Protein pellets were washed three times with 0.3 M guanidine hydrochloride in 95% ethanol, once with 100% ethanol, air-dried, and resuspended in 1% sodium dodecyl sulfate (SDS).

Real-Time Polymerase Chain Reaction (PCR). Purified RNA sample concentrations were determined on a Nano-Drop 1000 (Thermo Scientific). 1 µg of total RNA from whole lung homogenates was reverse-transcribed into cDNA with oligo-dT and random primers using an iScript cDNA synthesis kit (Bio-Rad). Gene expression was assessed utilizing TaqMan Gene Expression Assays-On-Demand primer/probe sets and TaqMan Universal Master Mix (Life Technologies) on the Applied Biosystems 7500 real-time PCR system complete with SDS software. 15 µl PCR reactions were performed using 2 µl of cDNA, 0.5 µl of primer/probe set, 7.5 µl of master mix, and 5 µl of DEPC-treated water by initially heating the samples to 50° C. for 2 minutes and 95° C. for 10 minutes, followed by 40 cycles of heating to 95° C. for 15 seconds and 60° C. for 1 minute. Target gene expression levels were normalized to the housekeeping gene Actinb and the fold change was calculated using the $2^{-\Delta\Delta C_t}$ method.

Western Blotting. Purified protein concentrations were determined by standard BCA assay (Pierce). SDS-PAGE using 50 µg of total protein was carried out with the Mini-Protean II System (BioRad) prior to Western blotting. Samples were heated at 95 oC for 20 minutes in Laemmli sample buffer (BioRad) containing 5% 2-mercaptoethanol before being loaded onto AnykD™ Mini-Protean TGX polyacrylamide gels (BioRad). Samples were run at 60V through the stacking gel and then 90V through the resolving gel in the presence of 1× Tris/Glycine/SDS buffer (BioRad). Gels were subsequently transferred in 1× Tris/Glycine buffer (BioRad) onto 0.2 µm PVDF membranes (BioRad) for 1 hour using 250 mA of constant current on ice. Membranes were blocked in SuperBlock® T20 blocking buffer (Pierce) for 30 minutes at room temperature and then incubated overnight at 4° C. with polyclonal rabbit anti-mouse Ym1 (STEMCELL Technologies), rabbit anti-mouse FIZZ1 (Peprotech), mouse anti-mouse Arg1 (BD Transduction Laboratories) or rabbit anti-mouse β-actin (Abcam) antibodies diluted 1:1500 in blocking solution. After three washes in 1× PBS with 0.05% Tween-20 (Promega), blots were incubated with either goat anti-rabbit-HRP or goat anti-mouse-HRP (1:5000, Thermo Scientific) for 1 hour at room temperature, washed again, and developed using ECL reagents (GE Healthcare) according to manufacturer's instructions. Blots were imaged using the FluorChem Q system and software (Protein Simple). Digital images were enhanced for clarity by uniformly adjusting the tonal range across samples for each band of interest using the black point slider of the Levels Tool in Adobe Photoshop.

Figure 3:
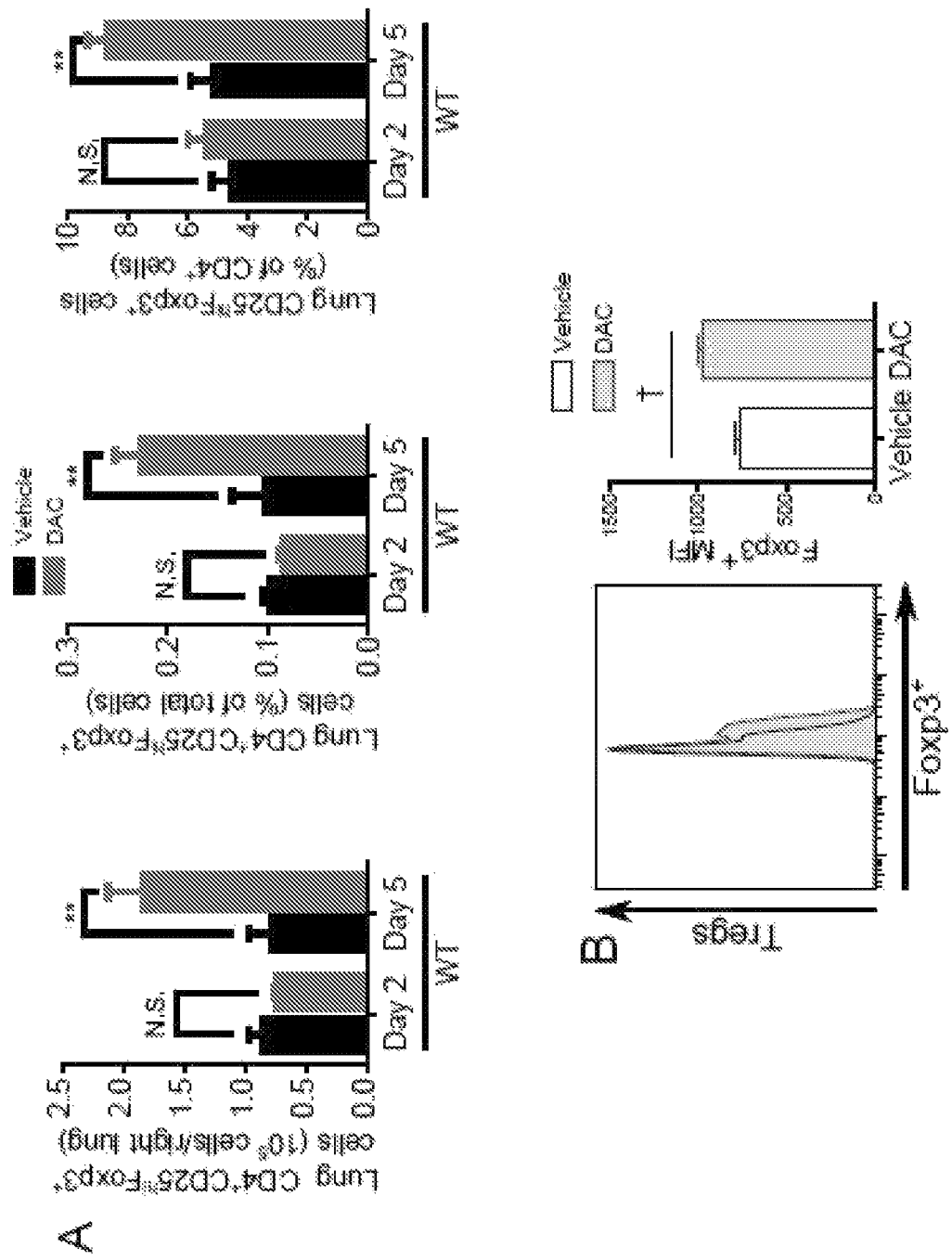
FIGS. 3A to 3D demonstrate that lung Treg frequency, activation state, suppressive phenotype, and proliferative capacity increased with DAC treatment after injury.
Figure 3:
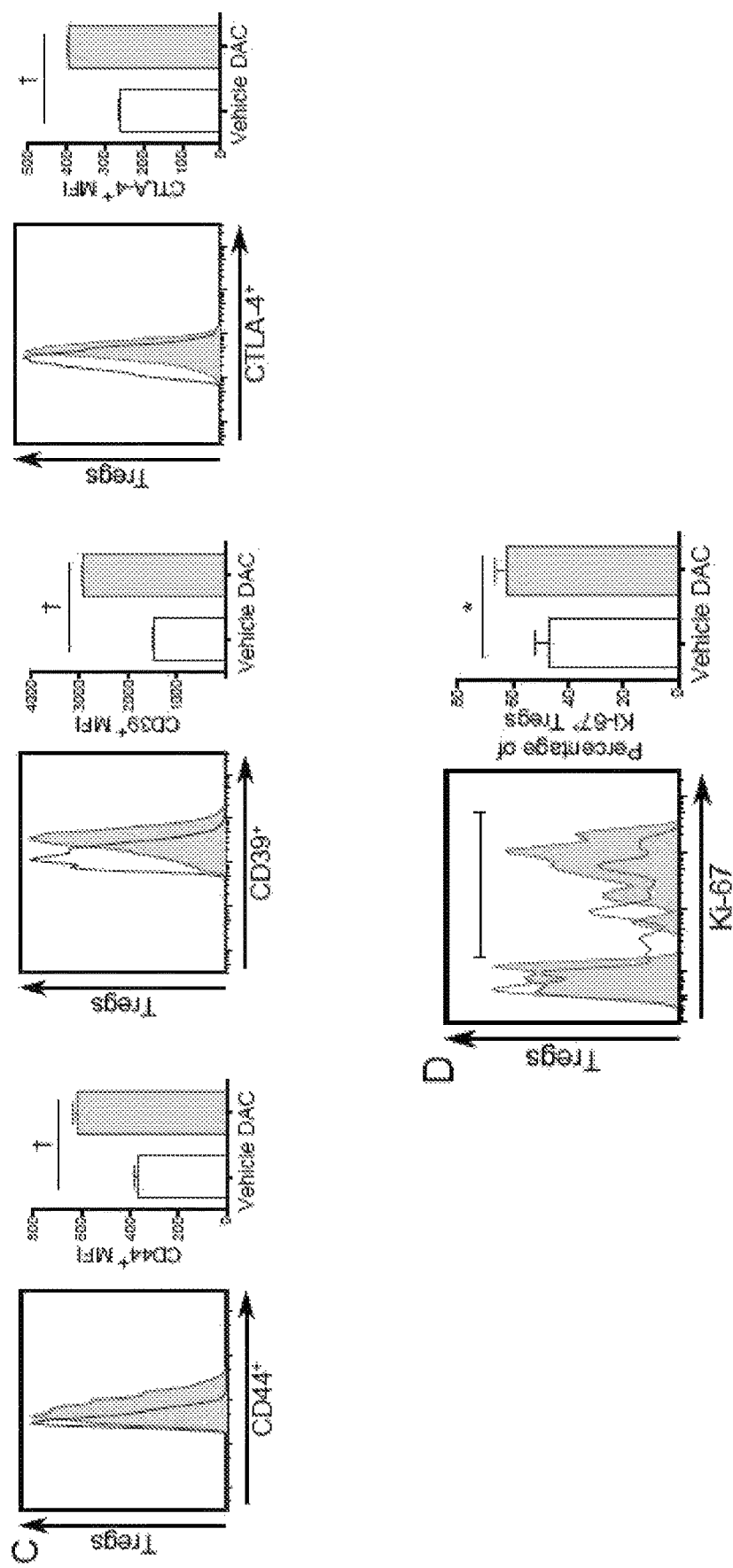
Figure 4:
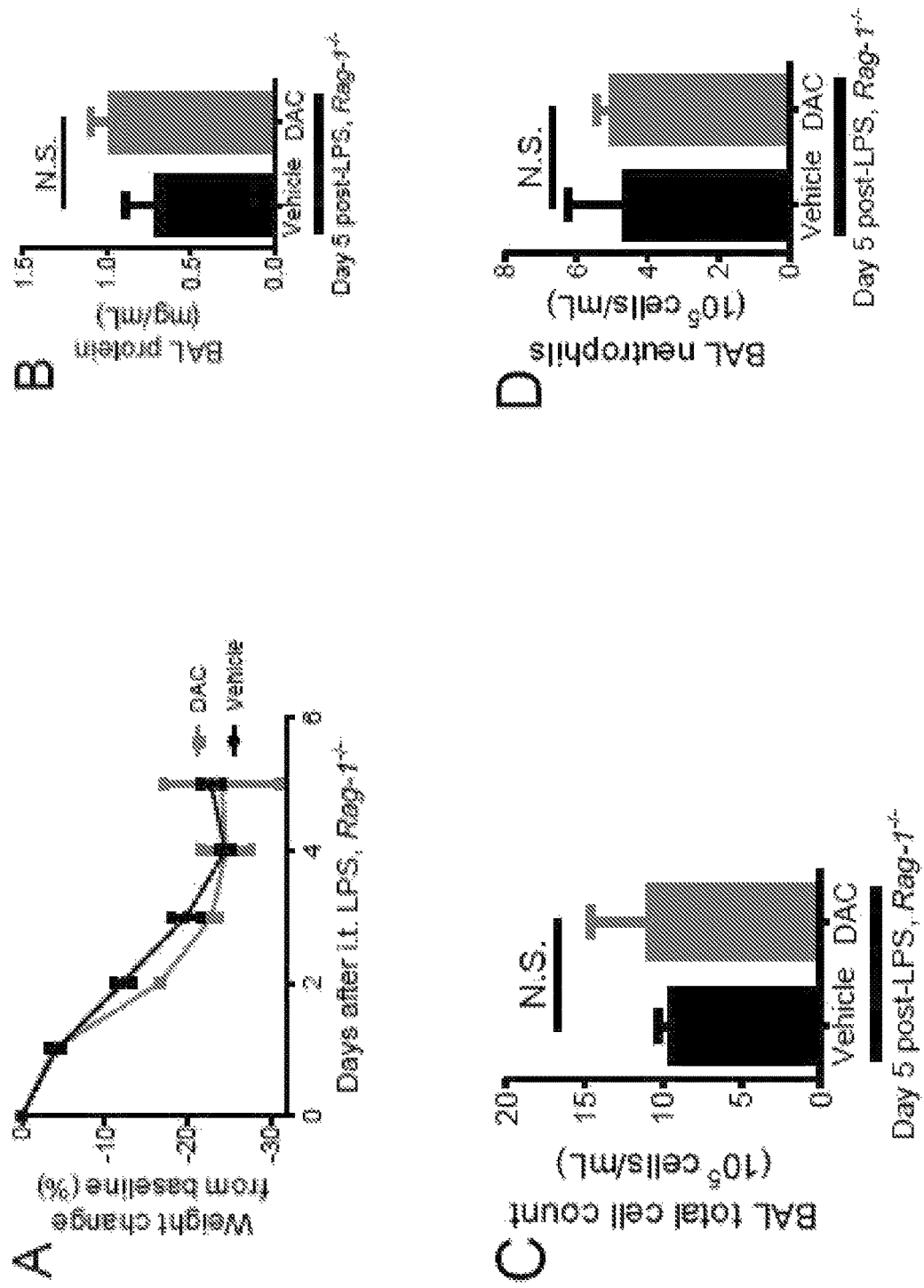
FIGS. 4A to 4E show that lymphocyte-deficient (Rag-1$^{-/-}$) mice did not resolve lung injury in response to DAC treatment.
Figure 4:
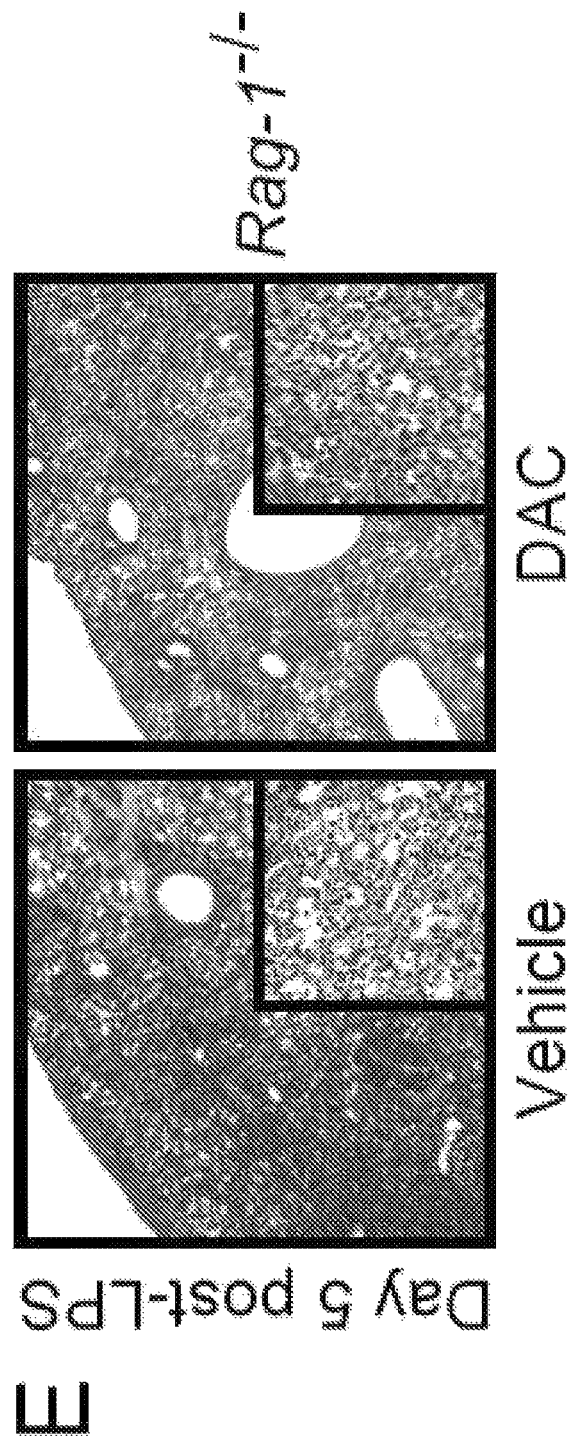
Figure 5:
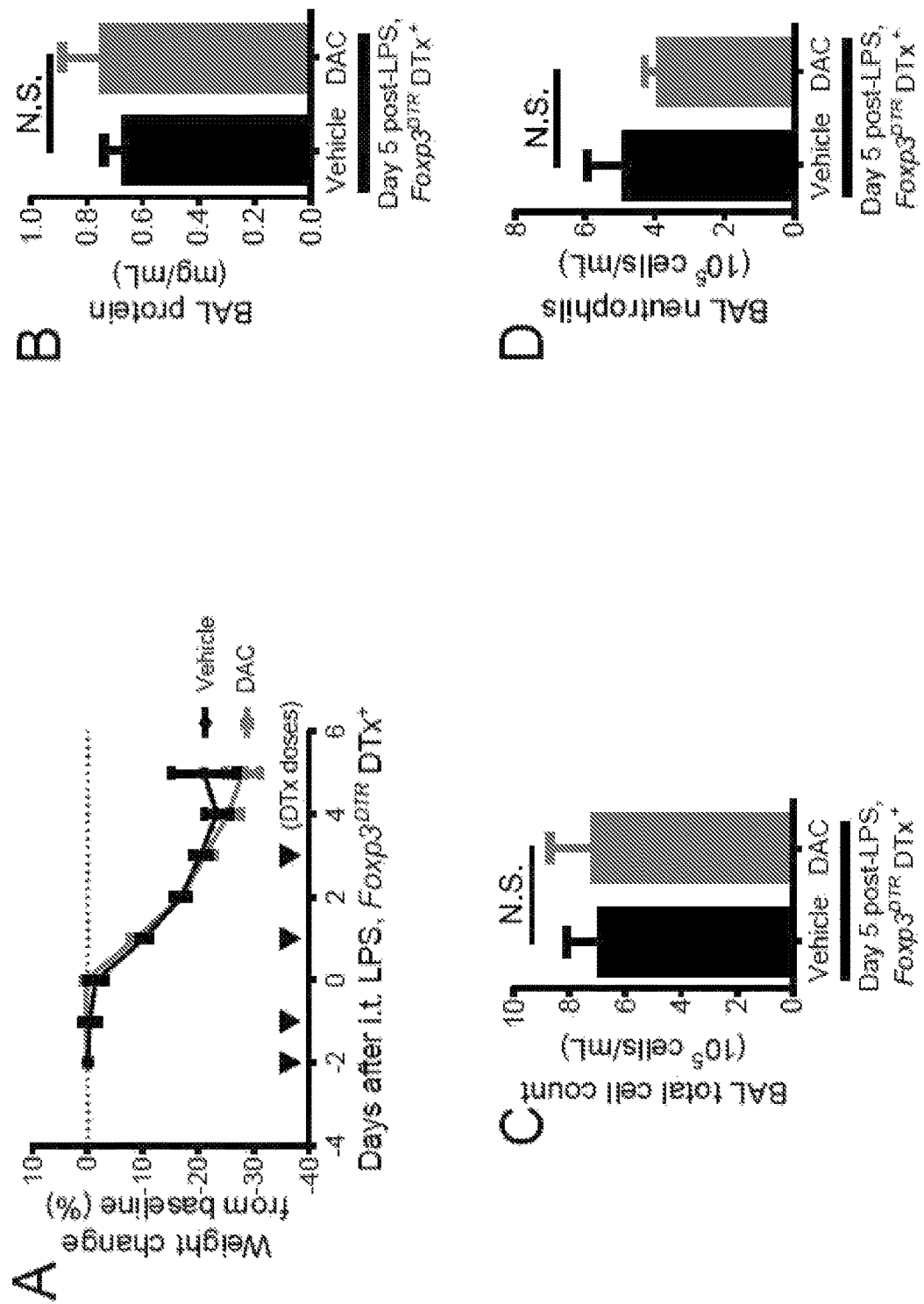
FIGS. 5A to 5E show that DAC did not promote resolution of lung injury in Treg-depleted mice.
Figure 5:
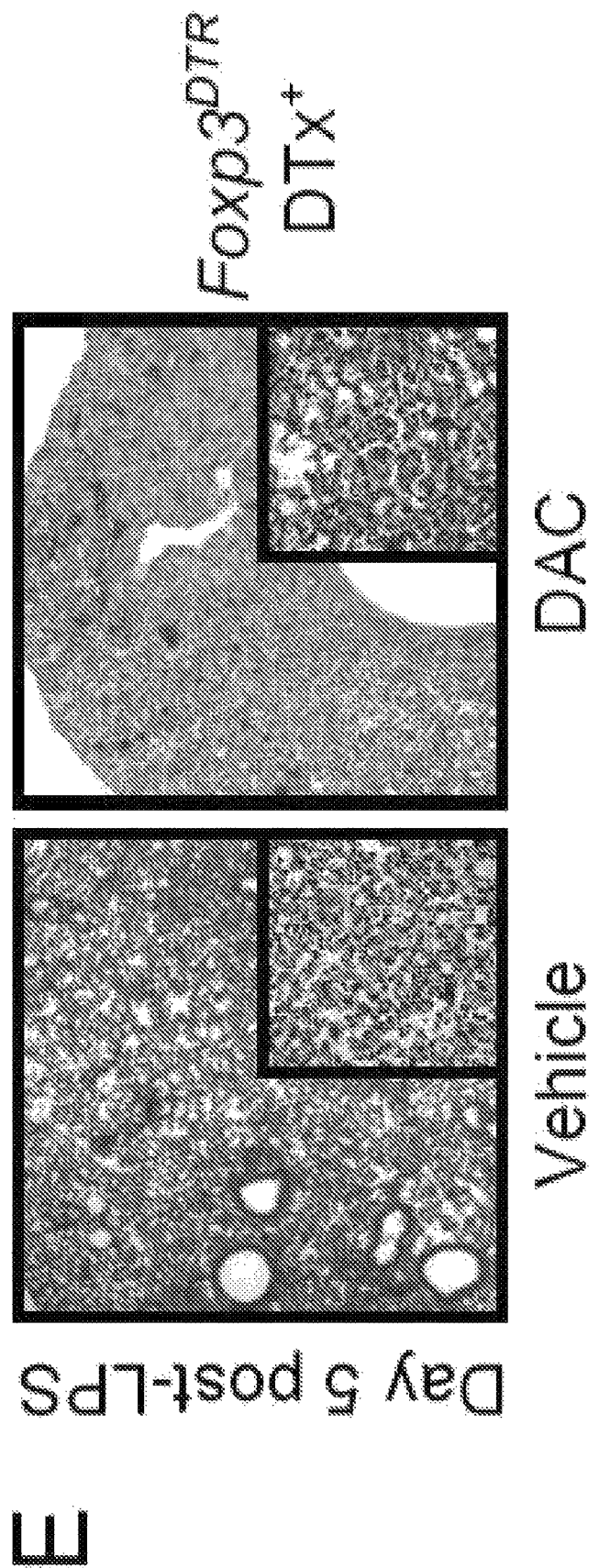

Flow Cytometry. After flushing the pulmonary circulation, right lungs were enzymatically digested and a single cell suspension was created. Lung and BAL cells were prepared for FACS analysis (D'Alessio et al. *J Clin Invest* 119: 2898-2913) with a live-dead discriminator and fluorochrome-conjugated antibodies. FIG. 3 shows the Treg gating strategy. Mean fluorescence intensity was calculated as the geometric mean of the positive population fluorescence.

On days 4, 5, or 6, cells were isolated from the BAL fluid or lung tissue. To isolate cells, lung tissue was minced with scissors into fine pieces, and digested for 30 minutes in a 1 mL solution containing 1 mg/mL collagenase Type II (Invitrogen), 1 mg/mL DNase I (Roche Applied Science), and RPMI 1640 medium (Invitrogen). Lung tissue was ground through a 100 µm cell strainer (BD Biosciences) to form a single-cell suspension, washed, and suspended in ACK buffer (Invitrogen) to lyse red blood cells. The remaining leukocytes were passed through a 100 µm cell strainer (BD Biosciences), washed, and suspended in 1 mL of PBS. For surface staining, 1×10$^6$ cells were stained with the LIVE/DEAD Fixable Blue viability kit according to manufacturer's instructions (Life Technologies), washed, and then incubated in FACS buffer with Fc Block-2.4G2 (BD Pharmingen) antibody to block FcγIII/II receptors for 10 minutes prior to the addition of fluorochrome-conjugated anti-mouse antibodies.

To identify macrophages and monocytes, cells were stained with anti-CD11b PE-Texas Red (Invitrogen), anti- F4/80-PE-Cy7 (Biolegend), anti-mouse mannose receptor (MMR, CD206)-Alexa Fluor 647 (Biolegend), anti-Dectin-1-Alexa Fluor 700 (R&D systems), anti-Ly6c-BV605 (Biolegend), anti-CD64-PE (Biolegend), and anti-Siglec-F-BV421 (BD Biosciences). For intracellular staining of monocytes/macrophages, isolated cells were first cultured in 1 mL of complete RPMI media containing 5% mouse serum (Jackson Immuno Research) for 4 hours at 37° C. with Brefeldin A (eBioscience) and washed twice prior to surface staining. $1 \times 10^6$ surface-stained cells were washed, fixed, and permeabilized with a Cytofix/Cytoperm kit (BD Biosciences) prior to intracellular staining for 30 minutes with rabbit anti-mouse primary antibodies to FIZZ1 (1:100, Peprotech). Intracellular-stained cells were washed once, stained for an additional 30 minutes with a donkey anti-rabbit-BV510 secondary antibody (1:100, Biolegend) for anti-FIZZ1, and washed again prior to analysis. Regulatory T cell (Treg) number and activation were assessed by surface staining with anti-CD4-Ax700 (Biolegend) prior to fixation/permeabilization with a FoxP3 Staining Buffer Set (eBioscience) and intracellular staining with anti-Foxp3-APC (eBioscience) antibody. A FACSAria instrument equipped with FACSDiva software (BD Biosciences) was used for data acquisition and FlowJo software was utilized for analysis (Tree Star Inc, San Carlos, Calif.). Instrument compensation was performed prior to data acquisition using UltraComp eBeads (eBioscience). Positive staining of live cells was determined against fluorescence-minus-one (FMO) controls after first gating away from debris and dead cells.

Statistical Analyses. All values are reported as mean±SEM. Parametric or nonparametric testing was performed as indicated. Changes in body weight between groups were compared using a repeated measure one-way analysis of variance (RM-ANOVA) with Fisher's protected least significant difference test. Kaplan-Meier survival curves were assessed by a log-rank Mantel-Cox test. All other analyses use a student's t-test when comparing two groups at one time point or a one-way analysis of variance (ANOVA) with Tukey's post-hoc test when comparing multiple groups at one time point. A p-value of <0.05 was used as the cut-off point for significance, with p<0.05 indicated by *, p<0.01 by , and p<0.001 by *.

Example 12

IL-4 Treatment Improved Mortality and Accelerated Resolution of Experimental Lung Injury WT C57BL/6 mice were treated with high-dose intratracheal (i.t.) LPS (4 mg/kg) on day 0, followed by delayed IL-4 treatment on days 2-4. When compared to PBS-treated (sham) mice, IL-4-treated mice exhibited significantly improved survival (92% vs. 57%, FIG. 14A), improved weight gain (FIG. 14B), and reduced histopathologic evidence of lung injury (FIG. 14C) by day 6 after i.t. LPS. Measurement of ALI parameters revealed as much as a three-fold reduction in BAL protein (FIG. 14D), a two-fold reduction in BAL albumin (FIG. 14E), and a five-fold reduction in BAL neutrophils (FIG. 14F) at latter time points (days 5-6) in mice treated with IL-4. IL-4 treatment following i.t. H2O did not alter day 4 BAL protein, albumin, or neutrophil numbers when compared to i.t. H2O plus sham treatment, and both groups had much less lung inflammation compared to LPS-exposed mice. Lung collagen, a marker of fibroproliferation, was also significantly reduced in IL-4-treated mice compared to sham at day 6 following i.t. LPS (FIG. 14G).

To assess whether differences in ALI resolution correlated with physiologic lung recovery and repair, select lung mechanics at day 6 following either i.t. H2O or i.t. LPS (FIG. 14H) were measured. There were no marked differences observed in dynamic respiratory system compliance (Crs) or diffusing capacity (DFCO) between i.t. H2O-exposed groups. However, mice exposed to i.t. LPS demonstrated a significant, approximately 25% reduction in Crs and DFCO, as compared to i.t. H20-exposed mice, and approached a DFCO of 0.45, which has been associated with extremely poor gas exchange (similar values were obtained from deceased and exsanguinated mice) (62). With IL-4 treatment in i.t. LPS-exposed mice, Crs recovered to the level observed in i.t. H2O groups, and the DFCO was also significantly improved. Therefore, the beneficial effects of IL-4 therapy on lung function following experimental ALI strongly supported its positive impact on resolution of lung inflammation and enhanced repair.

Example 13

IL-4 Blockade Impaired Endogenous ALI Resolution

Figure 15:
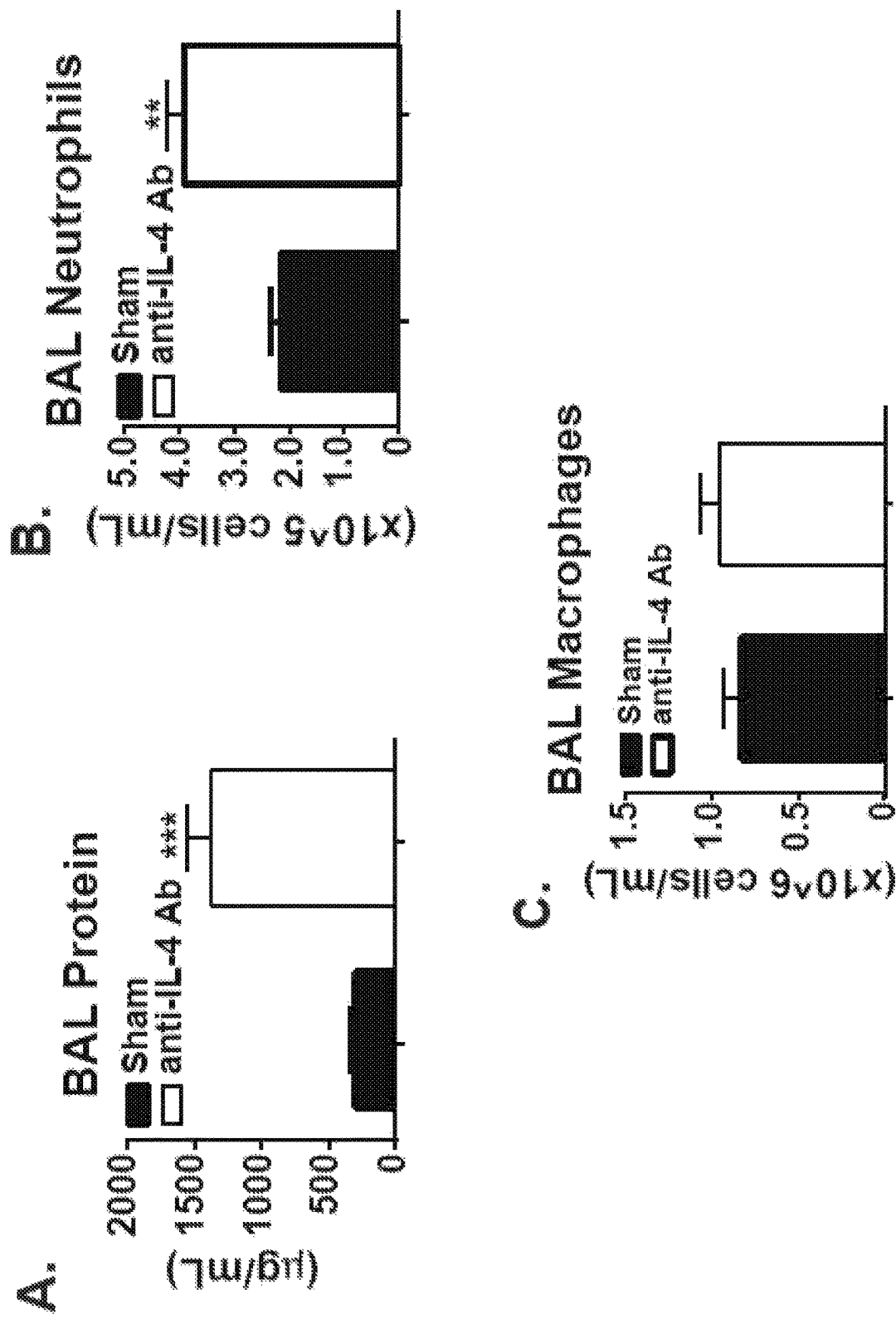
Figure 15:
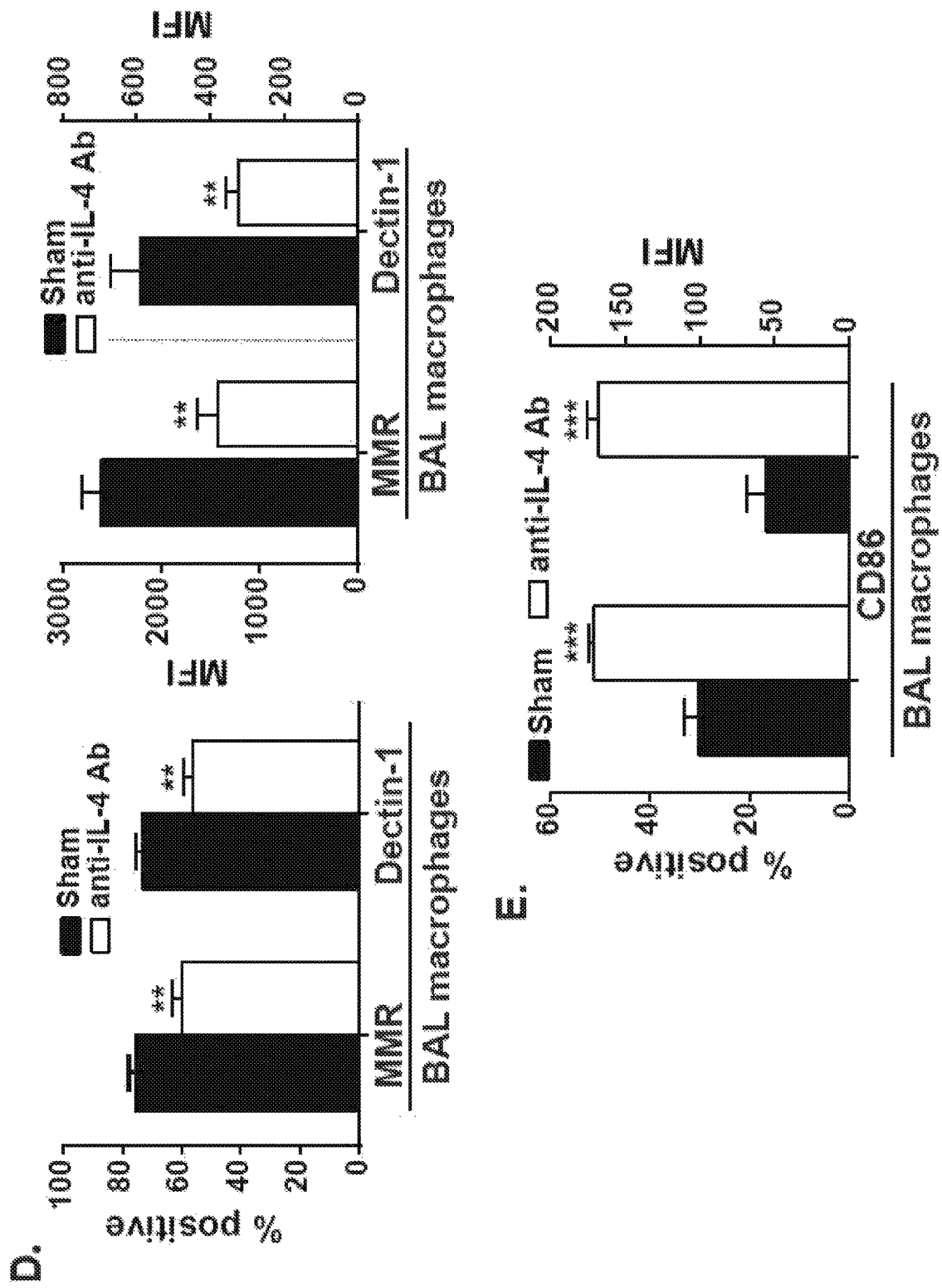

To determine whether endogenous IL-4 was necessary for ALI resolution in the i.t LPS ALI model, a once daily antibody-mediated blockade of IL-4 starting on day 1 after i.t. LPS (5 mg/kg) exposure to BALB/c mice, which were reported to produce more IL-4 at baseline (77), was used. Furthermore, a higher LPS dose was used to ensure that a difference in ALI resolution could be seen with IL-4 blockade. Mice treated with anti-IL-4 antibody (200 µg) exhibited significantly impaired resolution of ALI with a three-fold increase in BAL protein (FIG. 15A), and a two-fold increase in alveolar neutrophils (FIG. 15B), as compared to sham. Although the number of alveolar macrophages recovered at day 6 was similar (FIG. 15C), blocking IL-4 reduced the percent and MFI of $MMR^+$ or Dectin-$1^+$ (M2 markers) macrophages (FIG. 15D), yet increased $CD86^+$ (M1 marker) macrophages (FIG. 15E). Therefore, blocking endogenous IL-4 blunted ALI resolution with impaired M1 to M2 macrophage transition.

Example 14

Macrophages Robustly Expressed M2 Markers in Response to IL-4 and were Required to Accelerate ALI Resolution Having demonstrated the benefits of IL-4 therapy, whether IL-4 directly mediated M2 reprogramming of lung macrophages and whether this could be a mechanism to accelerate ALI resolution and lung repair was examined Mice treated with IL-4 after i.t. LPS exhibited significantly increased levels of M2 markers Arginase 1 (Arg1), Fizz1 (Retn1a), and Ym1 (Chil3), (FIG. 16A), which were validated at the protein level utilizing lung immunoblots (FIG. 16B). In contrast, IL-4 therapy reduced whole lung mRNA levels of inducible nitric oxide synthase (Nos2), a classical M1 marker, at day 4 (FIG. 16C). Furthermore, mice exposed to i.t. LPS plus IL-4 possessed significantly more FIZZ1-expressing monocytes or macrophages within the lung (FIG. 16D). To determine how IL-4 induced M2 programming in resident and recruited macrophage sub-populations, intracellular FIZZ1 expression among alveolar macrophages (AM), interstitial macrophages (IM), and monocytes (Mo) (FIG. 16E) was quantified. In i.t. LPS-exposed mice, IL-4 treatment resulted in a significant two-fold increase in the number FIZZ1-expressing interstitial macrophages, and a smaller, yet significant increase in FIZZ1-expressing alveolar macrophages, as compared to sham. The MFI of FIZZ1 expression among FIZZ1-positive cells was similar. Although a similar number of BAL macrophages were present in sham- and IL-4-treated mice (FIG. 16F), M2 and M1 surface marker expression among alveolar macrophages (F4/80$^+$) at day 6 in i.t. LPS-treated mice was also quantified to determine whether IL-4 could sustain macrophage reprogramming 2 days after the last exposure (FIG. 16G). In fact, alveolar macrophages from IL-4-treated mice expressed four-fold higher levels of MMR and Dectin-1, and three-fold lower levels of CD86, as compared to sham treated mice.

To address the importance of IL-4-stimulated macrophages to accelerate ALI resolution, intravenous liposomal clodronate was used to deplete macrophages on days 0 and 3, so as to not disrupt the onset of acute lung injury in mice exposed to i.t. LPS. Along with a 40-50% reduction in lung macrophages, significantly fewer macrophages were recovered by BAL in the macrophage-depleted group, which led to a two-fold increase in BAL neutrophils (FIG. 17A), BAL protein (FIG. 17B), and BAL albumin despite IL-4 treatment. In IL-4-treated mice, liposomal clodronate exposure did not markedly change the percentage of alveolar macrophages (F4/80$^+$CD11c$^+$CD11b$^-$) or their MMR expression (FIG. 17C). In contrast, liposomal clodronate exposure significantly reduced the percentage of interstitial macrophages (F4/80$^+$CD11b$^+$CD11c$^{+/-}$) and their MMR expression compared to control mice exposed to PBS liposomes (sham-depleted). Collectively, these data supported the importance of the interstitial macrophage subpopulation for the beneficial effects of IL-4 therapy.

Example 15

IL-4 Therapeutic Effects were Negated in Mice Possessing Impaired M2 Macrophage Activation Whether the success of IL-4 therapy required M2-specific macrophage activation was also examined To test this hypothesis, the response to i.t. LPS was compared between WT mice and Stat6$^{-/-}$ mice, which were deficient in a master transcriptional regulator of M2 differentiation and activation (75). Following i.t. LPS, IL-4-treated WT mice exhibited significant weight gain, as compared to all other groups at days 4 and 5 (FIG. 18A), as well as a greater than two-fold reduction in BAL protein (FIG. 18B) and BAL neutrophils (FIG. 18C) at day 5. Compared to IL-4-treated WT mice, Stat6$^{-/-}$ mice demonstrated impaired resolution with persistently elevated BAL protein and neutrophils, and a blunted response to IL-4. Furthermore, despite a similar number of macrophages recovered by BAL, as compared to WT mice (FIG. 18D), alveolar macrophages from Stat6$^{-/-}$ mice expressed significantly lower levels of MMR and Dectin-1 (FIG. 18E). In contrast to reduced M2 marker expression in Stat6$^{-/-}$ mice, similar CD86 expression between groups (FIG. 18E) was also observed. Overall, these data supported the importance of macrophage STAT6-dependent M2 protein upregulation as necessary for IL-4 to accelerate resolution following experimental ALI.

Example 16

Tregs were not Necessary for IL-4 to Accelerate ALI Resolution

The critical importance of CD4$^+$CD25$^+$Foxp3$^+$ regulatory T cells (Tregs) for experimental ALI resolution and lung repair was previously identified (59). As compared to sham-treated mice, IL-4-treated mice demonstrated a significant three-fold increase in Tregs recovered by BAL at day 6 after i.t. LPS (FIG. 19A). Because IL-4 were identified to induce proliferation and maintain full suppressive function of Tregs (87), whether Tregs contributed to the beneficial effects of IL-4 therapy on ALI resolution was examined Foxp3$^{DTR}$ mice were treated with i.p. diphtheria toxin to selectively deplete Tregs (FIG. 19B). A lower LPS dose was used because diphtheria toxin-treated Foxp3$^{DTR}$ mice have increased susceptibility to i.t. LPS, and achieved similar depletion in sham- and IL-4-treated groups (less than 0.2% of all CD4$^+$ cells in spleen, lung, BAL) as before (97). Despite Treg absence, IL-4 therapy in Foxp3$^{DTR}$ mice significantly increased weights (FIG. 19C), and significantly reduced parameters of ALI including BAL protein (FIG. 19D), BAL total cell count (FIG. 19E), and BAL neutrophils (FIG. 19F) compared to sham therapy in Foxp3$^{DTR}$ mice when assessed at day 6 after i.t. LPS. A significant increase in BAL macrophages in IL-4-treated Foxp3$^{DTR}$ mice compared to sham-treated mice (FIG. 19G), as well as higher M2 macrophage surface marker expression (FIG. 19H) was also observed. Collectively, these data demonstrated that Tregs were not required for IL-4 to accelerate ALI resolution and to reprogram lung macrophages.

Example 17

IL-4 Therapy also Accelerated Resolution Following Infection-Induced ALI

As is the case with any experimental ALI model, i.t. LPS could not recapitulate all of the pathologic features of human ARDS (83). Furthermore, there were previous reports that IL-4 programming of M2 macrophages might detrimentally effect macrophage-derived bacterial clearance (76). Therefore, whether IL-4 would be beneficial in experimental ALI in a live bacteria model induced by intratracheal administration of *Pseudomonas aeruginosa* O1 strain (i.t. PAO1) was tested. Reproducible lung injury and resolution patterns by days 4-5 following i.t. PAO1, with significantly reduced lung CFUs by day 2, was previously demonstrated (57). Mice were exposed to i.t. PAO1 on day 0, followed 2 and 3 days later with IL-4 or sham treatment. At day 4, with similar lung CFU counts between groups, IL-4-treated mice exhibited significant, two-fold reductions in BAL protein (FIG. 20A) and BAL albumin (FIG. 20B). In addition, a four-fold reduction in BAL neutrophils (FIG. 20C) was observed. Despite similar numbers of BAL macrophages (FIG. 20D), IL-4 treatment more than doubled the percentage of alveolar macrophages (F4/80+) that expressed the M2 surface markers MMR and Dectin-1, and also significantly increased the MFI for each marker compared to macrophages from sham-treated mice (FIG. 20E).

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for treating an acute inflammatory disease or disorder in a human subject, the method comprising:
   identifying a human subject having an acute inflammatory disease or disorder, and
   administering a pharmaceutical composition consisting essentially of a DNA methyltransferase inhibitor in an amount of 50-300 mg/day to the subject,
   thereby treating the acute inflammatory disease or disorder in the subject.

2. A method for treating a lung injury in a human subject, the method comprising:
   identifying a human subject having a lung injury, and
   administering a pharmaceutical composition consisting essentially of a DNA methyltransferase inhibitor in an amount of 50-300 mg/day to the subject, thereby treating the lung injury in the subject.

3. The method of claim 1, wherein the acute inflammatory disease or disorder or lung injury is an acute lung injury.

4. The method claim 1, wherein the acute inflammatory disease or disorder or lung injury is acute respiratory distress syndrome (ARDS).

5. The method of claim 1 wherein the pharmaceutical composition consists of a therapeutically effective amount of a DNA methyltransferase inhibitor.

6. The method of claim 2 wherein the pharmaceutical composition consists of a therapeutically effective amount of a DNA methyltransferase inhibitor.

* * * * *

SEQUENCE LISTING

<160> NUMBER OF SEQ ID NOS: 4

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met His Ile His Gly Cys Asp Lys Asn His Leu Arg Glu Ile Ile Gly
1               5                   10                  15

Ile Leu Asn Glu Val Thr Gly Glu Gly Thr Pro Cys Thr Glu Met Asp
            20                  25                  30

Val Pro Asn Val Leu Thr Ala Thr Lys Asn Thr Thr Glu Ser Glu Leu
        35                  40                  45

Val Cys Arg Ala Ser Lys Val Leu Arg Ile Phe Tyr Leu Lys His Gly
    50                  55                  60

Lys Thr Pro Cys Leu Lys Lys Asn Ser Ser Val Leu Met Glu Leu Gln
65                  70                  75                  80

Arg Leu Phe Arg Ala Phe Arg Cys Leu Asp Ser Ser Ile Ser Cys Thr
                85                  90                  95

Met Asn Glu Ser Lys Ser Thr Ser Leu Lys Asp Phe Leu Glu Ser Leu
                100                 105                 110

Lys Ser Ile Met Gln Met Asp Tyr Ser
        115                 120

<210> SEQ ID NO 2
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgcacatac acggatgcga caaaaatcat cttcgggaga ttattgggat cctgaacgag      60
gtgacgggag aaggaacccc atgcaccgag atggacgtcc ccaacgttct gactgccact     120
aagaacacaa ctgaaagtga actcgtatgc cgcgcatcga aggttttgcg aatattttac     180
cttaagcacg ggaagactcc gtgcttgaaa aagaactcat cggttctcat ggaattgcaa     240 agactttttcc gcgccttccg gtgcctcgac tcgtctattt cttgcactat gaacgagtca     300
aaaagtacca gtcttaaaga tttcctcgaa agccttaaga gtataatgca gatggattat     360
agc                                                                    363

<210> SEQ ID NO 3
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

```
Ile Phe Ala Ala Ser Lys Asn Thr Thr Glu Lys Glu Thr Phe Cys Arg
    35                  40                  45

Ala Ala Thr Val Leu Arg Gln Phe Tyr Ser His His Glu Lys Asp Thr
 50                  55                  60

Arg Cys Leu Gly Ala Thr Ala Gln Gln Phe His Arg His Lys Gln Leu
 65                  70                  75                  80

Ile Arg Phe Leu Lys Arg Leu Asp Arg Asn Leu Trp Gly Leu Ala Gly
                 85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
    130

<210> SEQ ID NO 4
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgcacatac acggatgcga caaaaatcat cttcgggaga ttattgggat cctgaacgag      60
gtgacgggag aaggaacccc atgcaccgag atggacgtcc ccaacgttct gactgccact     120
aagaacacaa ctgaaagtga actcgtatgc cgcgcatcga aggttttgcg aatattttac     180
cttaagcacg ggaagactcc gtgcttgaaa aagaactcat cggttctcat ggaattgcaa     240 agactttttcc gcgccttccg gtgcctcgac tcgtctattt cttgcactat gaacgagtca     300
aaaagtacca gtcttaaaga tttcctcgaa agccttaaga gtataatgca gatggattat     360
agc                                                                   363
```